(12) United States Patent
Sun et al.

(10) Patent No.: US 8,383,662 B2
(45) Date of Patent: Feb. 26, 2013

(54) BICYCLIC HETEROARYL COMPOUNDS

(75) Inventors: Chung-Ming Sun, Rancho Cucamonga, CA (US); Min-Liang Kuo, Taipei (TW); Yufeng Jane Tseng, Taipei (TW)

(73) Assignees: National Chiao Tung University, Hsinchu (TW); National Taiwan University, Taipei (TW)

( * ) Notice: Subject to any disclaimer, the term of this patent is extended or adjusted under 35 U.S.C. 154(b) by 0 days.

(21) Appl. No.: 12/896,244

(22) Filed: Oct. 1, 2010

(65) Prior Publication Data
US 2011/0082143 A1  Apr. 7, 2011

Related U.S. Application Data

(63) Continuation-in-part of application No. 11/949,070, filed on Dec. 3, 2007, now Pat. No. 7,825,261.

(60) Provisional application No. 60/873,041, filed on Dec. 5, 2006.

(51) Int. Cl.
*A61K 31/416* (2006.01)
*A61K 31/4184* (2006.01)
*C07D 235/04* (2006.01)
*C07D 209/02* (2006.01)

(52) U.S. Cl. ............ 514/394; 514/405; 548/305.1; 548/361.1

(58) Field of Classification Search .......... 514/394, 514/405; 548/305, 361.1
See application file for complete search history.

(56) References Cited

U.S. PATENT DOCUMENTS
7,511,145 B2 * 3/2009 Schmitz et al. ............ 546/167
2005/0187390 A1 * 8/2005 Schmitz et al. ............ 544/310

OTHER PUBLICATIONS

STN-12896244-preliminary-02202012 (2012).*
Chang et al., Journal of Combinatorial Chemistry, (2008), vol. 10, p. 466-474.*
Yeh et al., Combinatorial Chemistry and High Throughput Screening (2004), 7(3), p. 251-255.*

* cited by examiner

*Primary Examiner* — Yong Chu
(74) *Attorney, Agent, or Firm* — Birch, Stewart, Kolasch & Birch, LLP

(57) ABSTRACT

Bicyclic heteroaryl compounds of formula (I) shown below are disclosed. Each variable in formula (I) is defined in the specification. Also disclosed is treatment of cancer with these compounds.

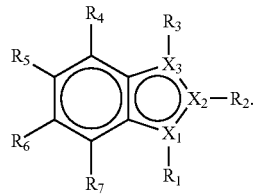

(I)

8 Claims, 5 Drawing Sheets

BICYCLIC HETEROARYL COMPOUNDS

CROSS REFERENCE TO RELATED APPLICATION

This application is a continuation-in-part and claims priority to U.S. patent application Ser. No. 11/949,070, filed Dec. 3, 2007 now U.S. Pat. No. 7,825,261, which in turn claims priority to U.S. Provisional Application Ser. No. 60/873,041, filed Dec. 5, 2006. The contents of these two applications are incorporated herein in its entirety.

BACKGROUND

Lymphangiogenesis is the formation of lymphatic vessels from pre-existing lymphatic vessels. It plays an important role in promoting neoplasm metastasis. It has been found that vascular endothelial growth factor receptor-3 (VEGFR-3) mediates lymphangiogenesis in response to its two ligands, VEGF-C and VEGF-D. Thus, it is desirable to develop novel drugs that inhibit the VEGFR-3/ligand signaling pathway for cancer treatment.

SUMMARY

This invention is based on the discovery that certain bicyclic heteroaryl compounds are effective in reducing metastasis and treating cancer by inhibiting VEGFR-3 activities.

In one aspect, this invention features bicyclic heteroaryl compounds of formula (I):

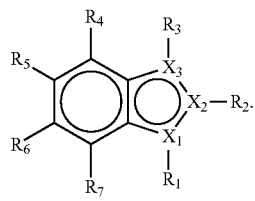

In this formula, each of $X_1$, $X_2$, and $X_3$, independently, is C or N, and at least two of $X_1$, $X_2$, and $X_3$ are each N; each of $R_1$ and $R_3$, independently, is deleted, H, alkyl, alkenyl, alkynyl, cycloalkyl, cycloalkenyl, heterocycloalkyl, heterocycloalkenyl, aryl, heteroaryl, halo, CN, $NO_2$, $OR_a$, $COOR_a$, $OC(O)R_a$, $C(O)R_a$, $C(O)NR_aR_b$, $C(O)N(R_a)N(R_b)C(O)R_e$, $NR_aR_b$, $N(R_e)SO_2NR_aR_b$, $SO_2NR_aR_b$, or $SR_a$, in which each of $R_a$, $R_b$, and $R_e$, independently, is H, alkyl, cycloalkyl, heterocycloalkyl, aryl, or heteroaryl, or $R_a$ and $R_b$ together with the nitrogen atom to which they are attached form heterocycloalkyl or heteroaryl; $R_2$ is heterocycloalkenyl, aryl, or heteroaryl; each of $R_4$, $R_5$, $R_6$, and $R_7$, independently, is H, alkyl, alkenyl, alkynyl, cycloalkyl, cycloalkenyl, heterocycloalkyl, heterocycloalkenyl, aryl, heteroaryl, halo, CN, $NO_2$, $OR_d$, $COOR_d$, $OC(O)R_d$, $C(O)R_d$, $C(O)NR_dR_e$, $C(O)N(R_d)N(R_e)C(O)R_f$, $NR_dR_e$, $N(R_f)SO_2NR_dR_e$, $SO_2NR_dR_e$, or $SR_d$, in which each of $R_d$, $R_e$, and $R_f$, independently, is H, alkyl, cycloalkyl, heterocycloalkyl, aryl, or heteroaryl, or $R_d$ and $R_e$ together with the nitrogen atom to which they are attached form heterocycloalkyl or heteroaryl.

Referring to formula (I), a subset of the bicyclic heteroaryl compounds described above are those in which each of $X_1$ and $X_3$ is N and $X_2$ is C. In these compounds, $R_2$ can be heterocycloalkenyl or heteroaryl; $R_1$ can be alkyl or cycloalkyl; each of $R_4$, $R_5$, $R_6$, and $R_7$, independently, can be H, $C_1$-$C_{10}$ alkyl, $NR_dR_e$, $COOR_d$, $C(O)NR_dR_e$, $C(O)N(R_d)N(R_e)C(O)R_f$, or heteroaryl; or $R_5$ can be $COOR_d$ and each of $R_4$, $R_6$, and $R_7$, independently, can be H.

Another subset of the bicyclic heteroaryl compounds of formula (I) described above are those in which each of $X_1$ and $X_3$ is N, $X_2$ is C, and $R_2$ is benzimidazol-4-yl, dihydrobenzimidazol-4-yl, indazol-6-yl, or phenyl (e.g., phenyl substituted with amino, amido, or thioureido). In these compounds, $R_1$ can be alkyl or cycloalkyl; each of $R_4$, $R_5$, $R_6$, and $R_7$, independently, can be H, $C_1$-$C_{10}$ alkyl, $NR_dR_e$, $COOR_d$, $C(O)NR_dR_e$, $C(O)N(R_d)N(R_e)C(O)R_f$, or heteroaryl; or $R_5$ can be $COOR_d$ and each of $R_4$, $R_6$, and $R_7$, independently can be H.

Still another subset of the bicyclic heteroaryl compounds of formula (I) described above are those in which each of $X_1$ and $X_3$ is N, $X_2$ is C, and $R_2$ is

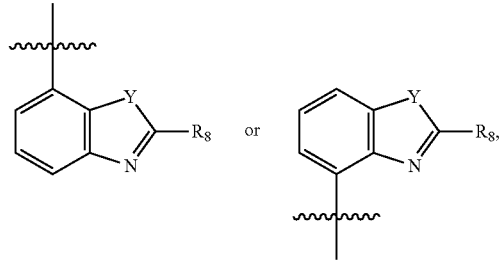

in which Y is O, S, Se, or $NR_g$, $R_g$ being H, alkyl, alkenyl, alkynyl, cycloalkyl, heterocycloalkyl, aryl, or heteroaryl, $R_8$ is H, alkyl, alkenyl, alkynyl, cycloalkyl, heterocycloalkyl, aryl, heteroaryl, $SR_h$, $SeR_h$, or $NR_hR_i$, each of $R_h$ and $R_i$ independently being H, alkyl, alkenyl, alkynyl, cycloalkyl, heterocycloalkyl, aryl, or heteroaryl. In these compounds, Y can be $NR_g$ and $R_8$ can be $SR_h$, or $SeR_h$; or $R_8$ can be $NR_g$ and Y can be $SR_h$, or $SeR_h$; $R_1$ can be alkyl or cycloalkyl; each of $R_4$, $R_5$, $R_6$, and $R_7$, independently, can be H, $C_1$-$C_{10}$ alkyl, $NR_dR_e$, $COOR_d$, $C(O)NR_dR_e$, $C(O)N(R_d)N(R_e)C(O)R_f$, or heteroaryl; or $R_5$ can be $COOR_d$ and each of $R_4$, $R_6$, and $R_7$, independently can be H.

The term "alkyl" refers to a straight or branched monovalent hydrocarbon containing, unless otherwise stated, 1-20 carbon atoms (e.g., $C_1$-$C_{10}$ or $C_1$-$C_4$). Examples of alkyl include, but are not limited to, methyl, ethyl, n-propyl, i-propyl, n-butyl, i-butyl, and t-butyl. The term "alkenyl" refers to a straight or branched monovalent hydrocarbon containing 2-20 carbon atoms (e.g., $C_2$-$C_{10}$ or $C_2$-$C_4$) and one or more double bonds. Examples of alkenyl include, but are not limited to, ethenyl, propenyl, propenylene, allyl, and 1,4-butadienyl. The term "alkynyl" refers to a straight or branched monovalent hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. The term "alkoxy" refers to an —O-alkyl radical. Examples of alkoxy include, but are not limited to, methoxy, ethoxy, n-propoxy, isopropoxy, n-butoxy, iso-butoxy, sec-butoxy, and tert-butoxy. The term "acyloxy" refers to an —O—C(O)—R radical in which R can be H, alkyl, alkenyl, alkynyl, cycloalkyl, cycloalkenyl, heterocycloalkyl, heterocycloalkenyl, aryl, or heteroaryl. The term "amino" refers to $NH_2$, alkylamino, or arylamino. The term "alkylamino" refers to an —N(R)-alkyl radical in which R can be H, alkyl, alkenyl, alkynyl, cycloalkyl, cycloalkenyl, heterocycloalkyl, heterocycloalkenyl, aryl, or heteroaryl. The terms "amido" and "carbamido" refer to —NRC(O)R' and —C(O)NRR' radicals respectively, in which each of R and R', independently, can be H, alkyl, alkenyl, alkynyl, cycloalkyl, cycloalkenyl, heterocycloalkyl, heterocycloalkenyl, aryl, or heteroaryl.

The term "cycloalkyl" refers to a monovalent saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, 1,4-cyclohexylene, cycloheptyl, cyclooctyl, and adamantyl. The term "cycloalkenyl" refers to a monovalent non-aromatic hydrocarbon ring system having 3 to 30 carbons (e.g., $C_3$-$C_{12}$) and one or more double bonds. Examples include cyclopentenyl, cyclohexenyl, fluorenyl, and cycloheptenyl. The term "heterocycloalkyl" refers to a monovalent nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, 4-tetrahydropyranyl, and tetrahydrofuranyl. The term "heterocycloalkenyl" refers to a monovalent nonaromatic 5-8 membered monocyclic, 8-12 membered bicyclic, or 11-14 membered tricyclic ring system having one or more heteroatoms (such as O, N, S, or Se) and one or more double bonds. Examples of heterocycloalkenyl groups include, but are not limited to, pyranyl, dihydrobenzimidazolyl and 1,3-dihydrospiro[benzo[d]imidazol-2,1'-cyclopentane]-4-yl.

The term "aryl" refers to a monovalent 6-carbon monocyclic, 10-carbon bicyclic, 14-carbon tricyclic aromatic ring system. Examples of aryl groups include, but are not limited to, phenyl ("ph"), naphthyl, pyrenyl, anthryl, and phenanthryl. The term "aryloxyl" refers to an —O-aryl. The term "arylamino" refers to an —N(R)-aryl in which R can be H, alkyl, alkenyl, alkynyl, cycloalkyl, cycloalkenyl, heterocycloalkyl, heterocycloalkenyl, aryl, or heteroaryl. The term "heteroaryl" refers to a monvalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, pyrrolyl, furyl, imidazolyl, indazolyl, benzimidazolyl, pyrimidinyl, thienyl, oxazolyl, quinolyl, isoquinolyl, quinazolinyl, indolyl, and thiazolyl.

Alkyl, alkenyl, alkynyl, cycloalkyl, heterocycloalkyl, cycloalkenyl, heterocycloalkenyl, amino, aryl, and heteroaryl mentioned above include both substituted and unsubstituted moieties. Possible substituents on amino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, $C_1$-$C_{10}$ alkylimino, arylimino, $C_1$-$C_{10}$ alkylsulfonimino, arylsulfonimino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, nitroso, azido, acyl, thioacyl, acyloxy, carbamido, carbamyl (—C(O)NH$_2$), carboxyl (—COOH), and carboxylic ester. On the other hand, possible substituents on alkyl, alkenyl, alkylene, alkenylene, heteroalkylene, heteroalkenylene, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other by sharing one or more atoms (e.g., to form a spiro compound).

In another aspect, this invention features a method for treating cancer. The method includes administering to a subject in need thereof an effective amount of one or more bicyclic heteroaryl compounds of formula (I) shown above. An example of cancer that can be treated by the bicyclic heteroaryl compounds of this invention is lung cancer. The term "treating" or "treatment" refers to administering one or more bicyclic heteroaryl compounds to a subject, who has an above-described disease, a symptom of such a disease, or a predisposition toward such a disease, with the purpose to confer a therapeutic effect, e.g., to cure, relieve, alter, affect, ameliorate, or prevent the above-described disease, the symptom of it, or the predisposition toward it.

In addition, this invention encompasses a pharmaceutical composition that contains at least one of the above-mentioned bicyclic heteroaryl compounds and a pharmaceutically acceptable carrier.

The bicyclic heteroaryl compounds described above include the compounds themselves, as well as their salts, prodrugs, and solvates, if applicable. A salt, for example, can be formed between an anion and a positively charged group (e.g., amino) on a bicyclic heteroaryl compound. Suitable anions include chloride, bromide, iodide, sulfate, bisulfate, sulfamate, nitrate, phosphate, citrate, methanesulfonate, trifluoroacetate, acetate, malate, tosylate, tartrate, fumurate, salicylate, naphthalenesulfonate, glutamate, glucuronate, lactate, glutarate succinate, and maleate. Likewise, a salt can also be formed between a cation and a negatively charged group (e.g., carboxylate) on a bicyclic heteroaryl compound. Suitable cations include sodium ion, potassium ion, magnesium ion, calcium ion, and an ammonium cation such as tetramethylammonium ion. The bicyclic heteroaryl compounds also include those salts containing quaternary nitrogen atoms. Examples of prodrugs include esters and other pharmaceutically acceptable derivatives, which, upon administration to a subject, are capable of providing active bicyclic heteroaryl compounds. A solvate refers to a complex formed between an active bicyclic heteroaryl compound and a pharmaceutically acceptable solvent. Examples of pharmaceutically acceptable solvents include water, ethanol, isopropanol, ethyl acetate, acetic acid, and ethanolamine.

Also within the scope of this invention is a composition containing one or more of the bicyclic heteroaryl compounds described above for use in treating cancer, and the use of such a composition for the manufacture of a medicament for the just-mentioned treatment.

The details of one or more embodiments of the invention are set forth in the description below. Other features, objects, and advantages of the invention will be apparent from the following drawing, detailed description of embodiments, and also from the appending claims.

DETAILED DESCRIPTION

Figure 1:
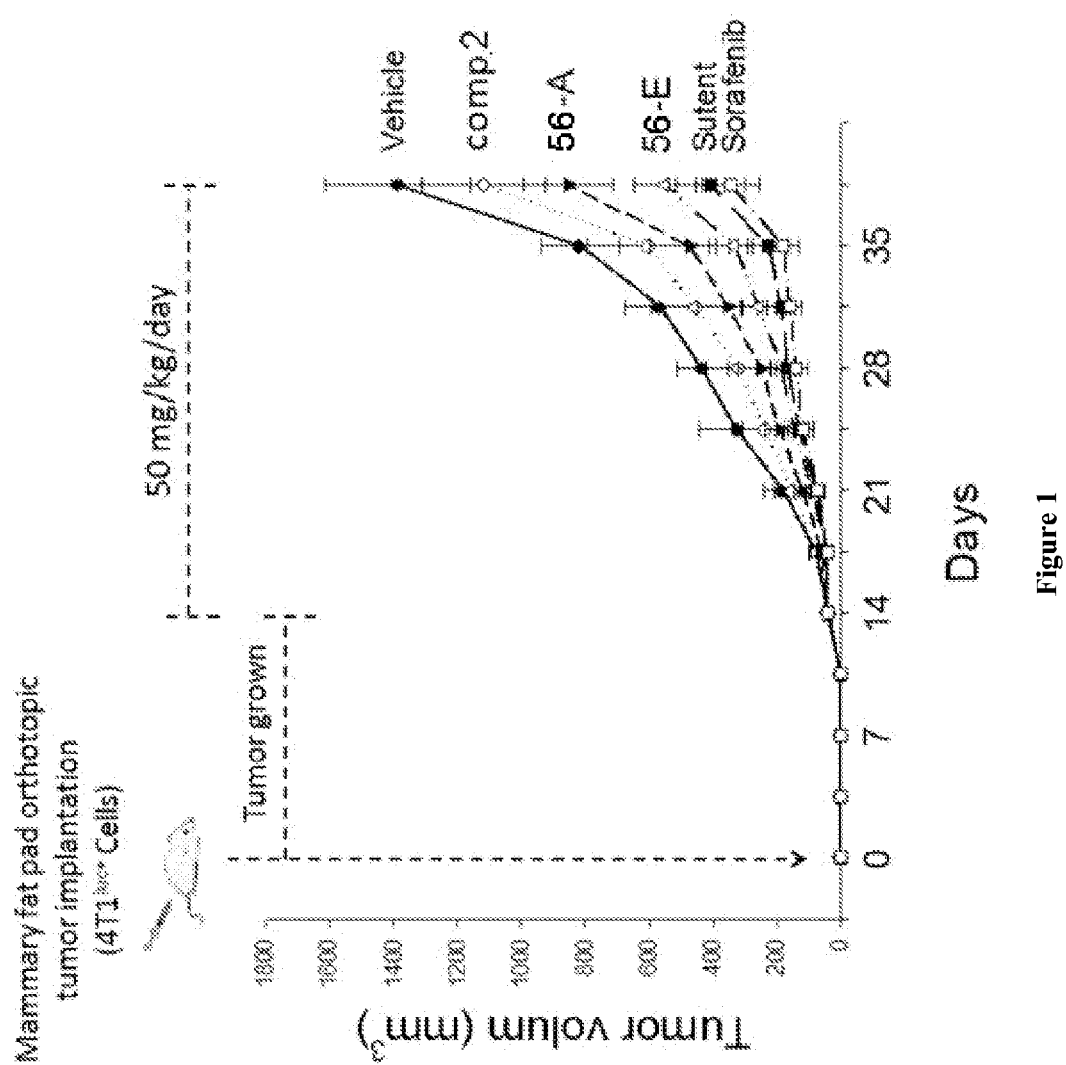
FIG. 1 illustrates the efficacy of certain compounds of this invention in inhibiting tumor growth in mice.

Shown below are 185 exemplary compounds of this invention:

Compound 1 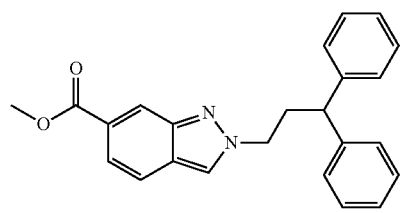
Compound 2 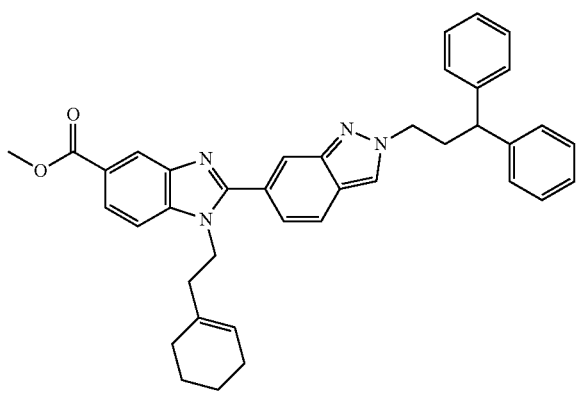
Compound 3 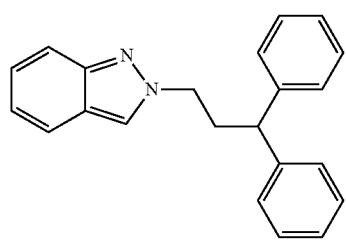
Compound 4 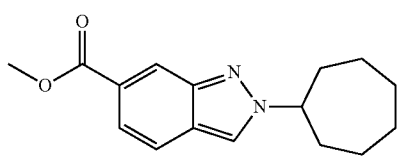
Compound 5 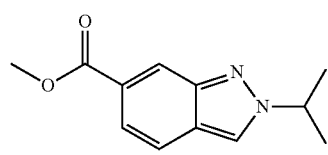
Compound 6 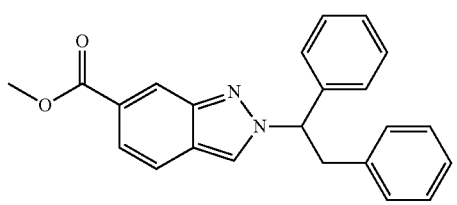
Compound 7 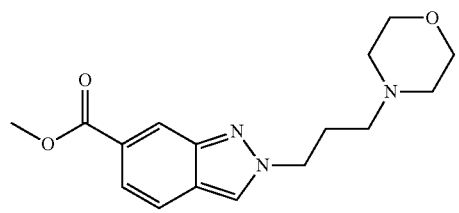
Compound 8 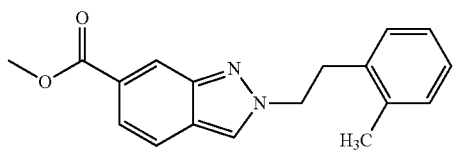
Compound 9 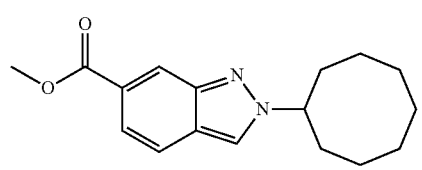
Compound 10 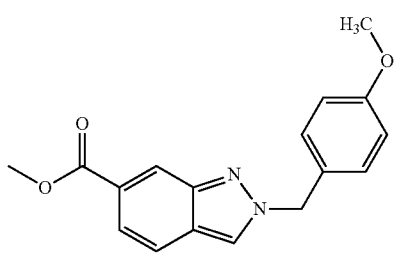
Compound 11 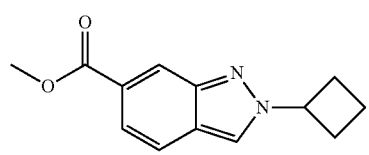
Compound 12 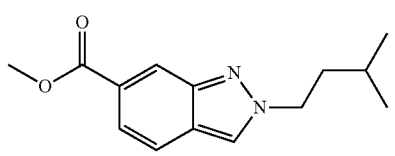

-continued
Compound 13
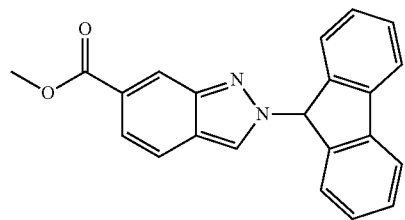
Compound 14
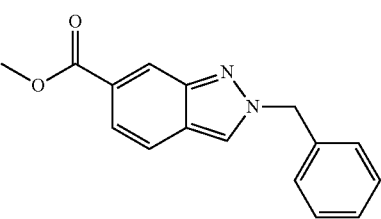
Compound 15
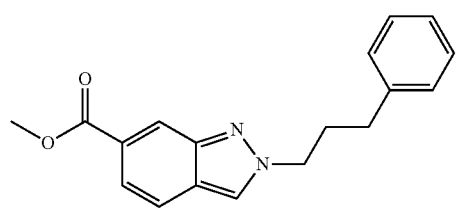
Compound 16
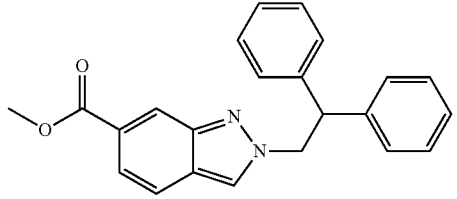
Compound 17
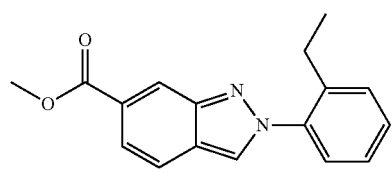
Compound 18
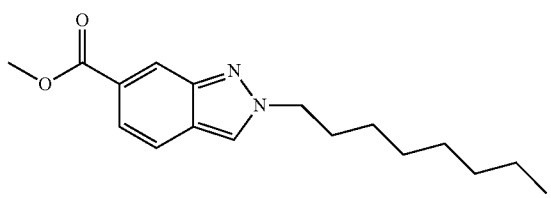
Compound 19
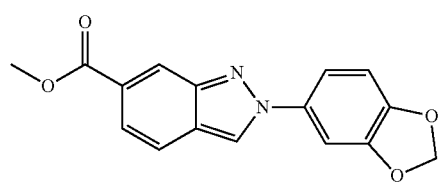
Compound 20
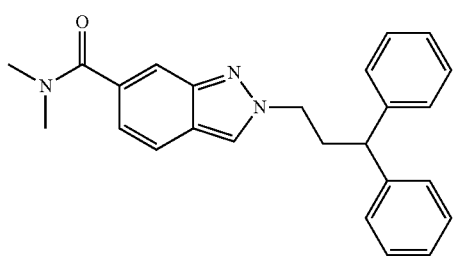
Compound 21
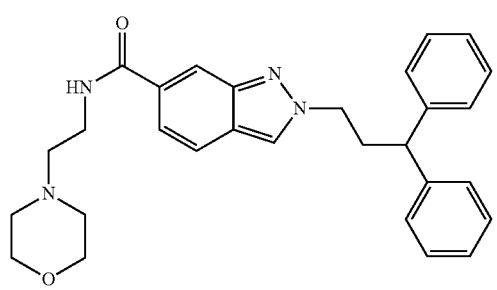
Compound 22
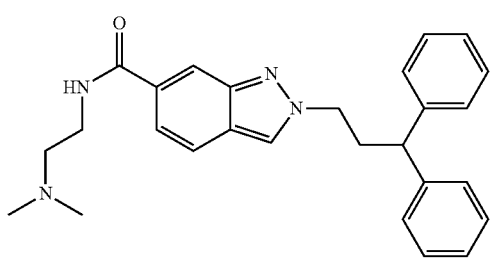
Compound 23
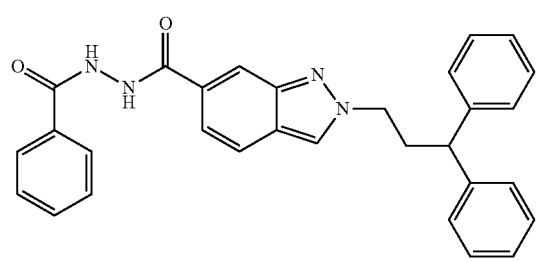
Compound 24
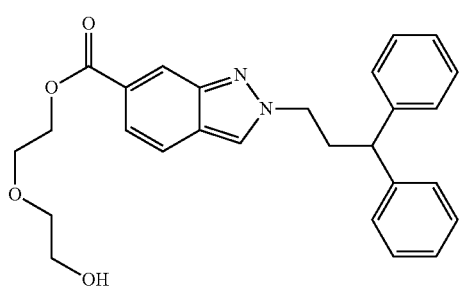

-continued
Compound 25
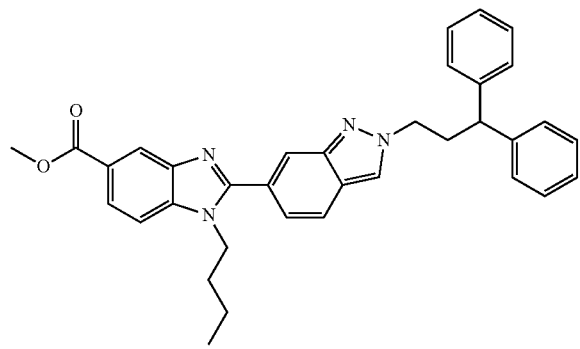
Compound 26
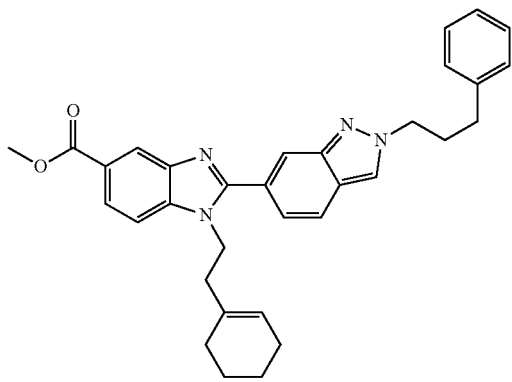
Compound 27
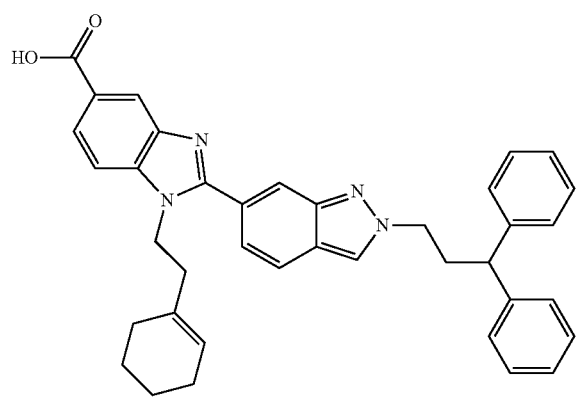
Compound 28
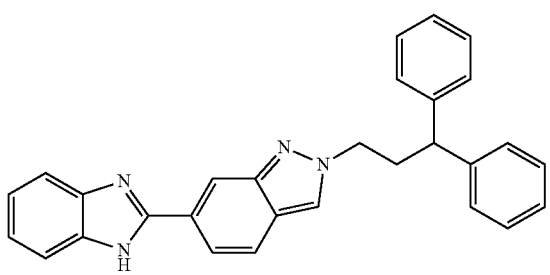
Compound 29
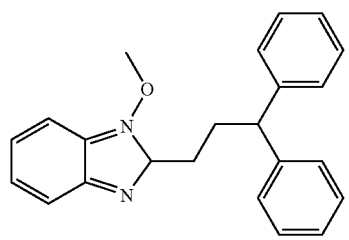
Compound 30
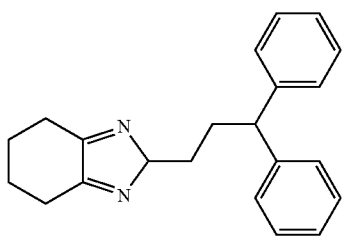
Compound 31
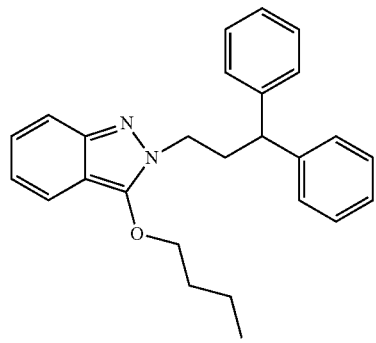
Compound 32
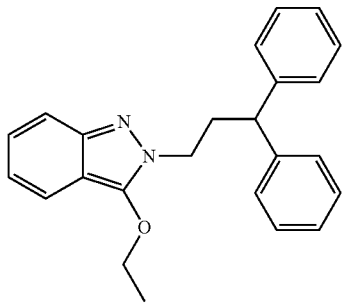
Compound 33
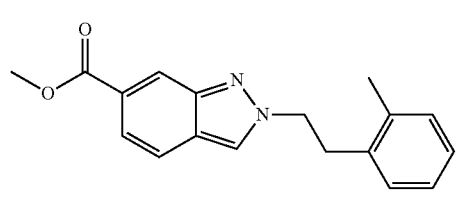
Compound 34
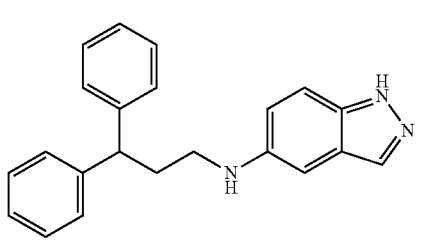

-continued
Compound 35
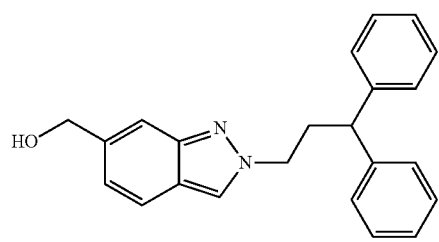
Compound 36
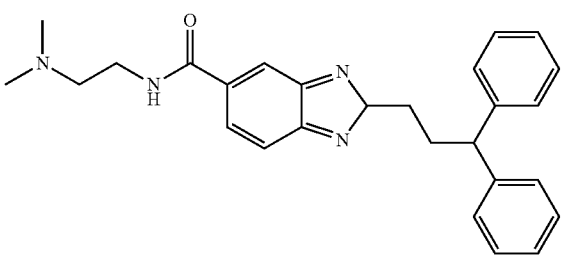
Compound 37
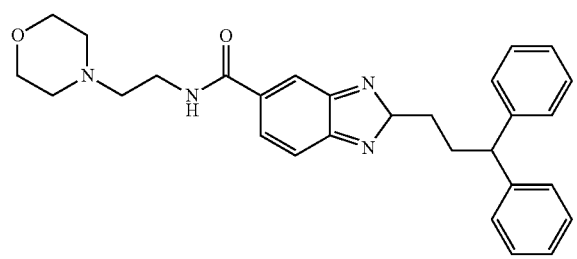
Compound 38
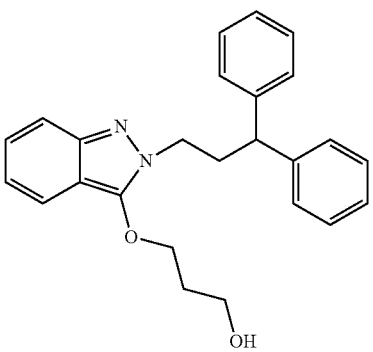
Compound 39
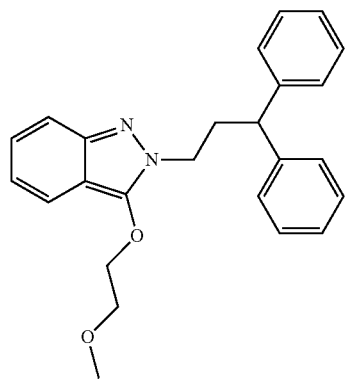
Compound 40
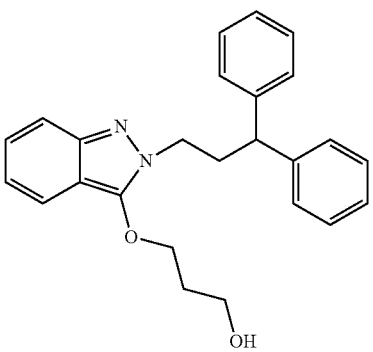
Compound 41
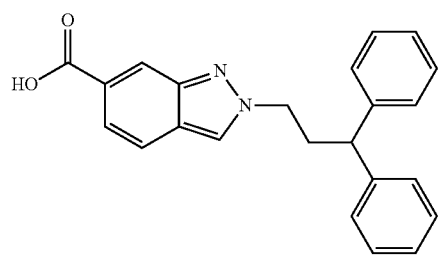
Compound 42
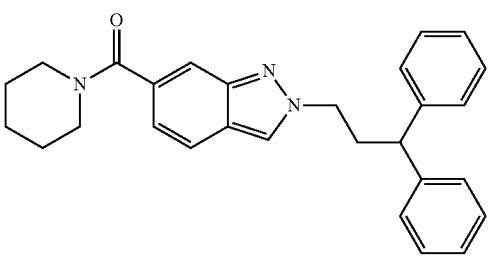
Compound 43
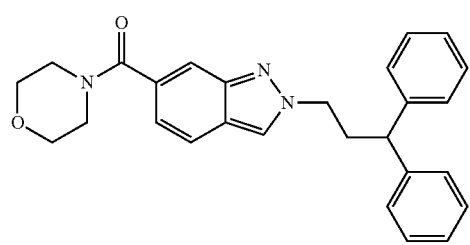
Compound 44
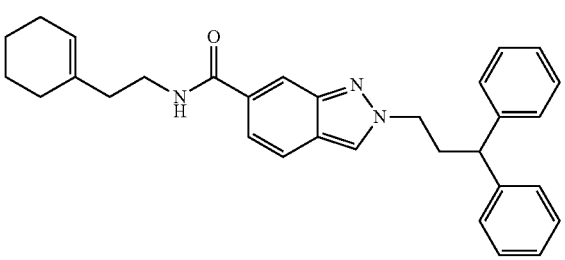

-continued
Compound 45
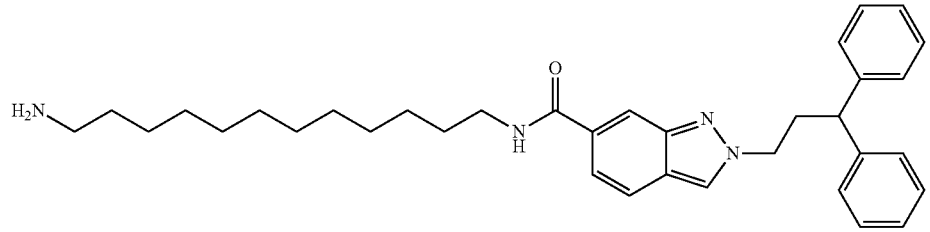
Compound 46
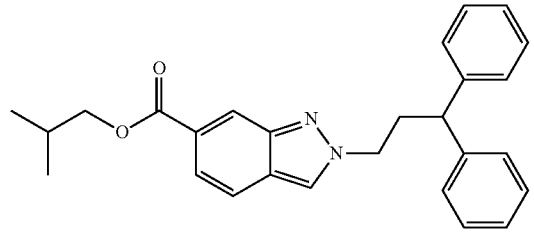
Compound 47
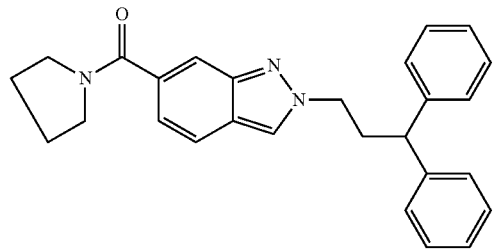
Compound 48
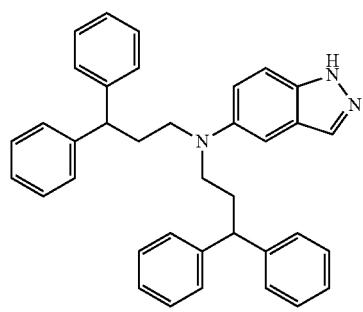
Compound 49
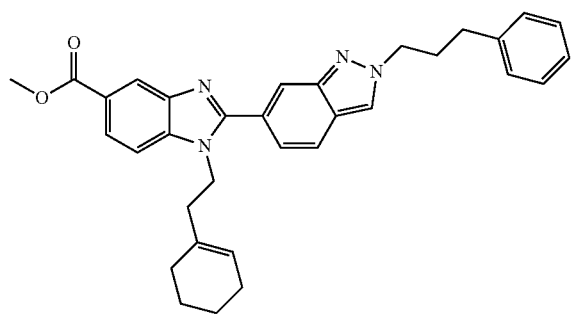
Compound 50
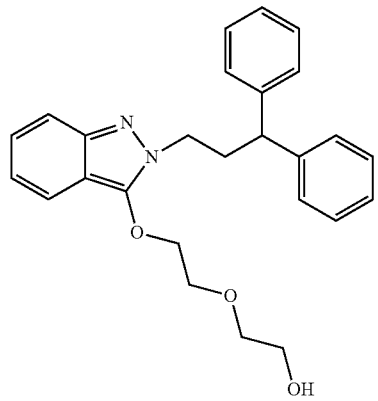
Compound 51
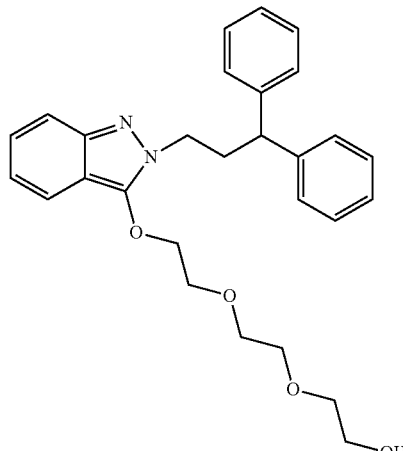
Compound 52
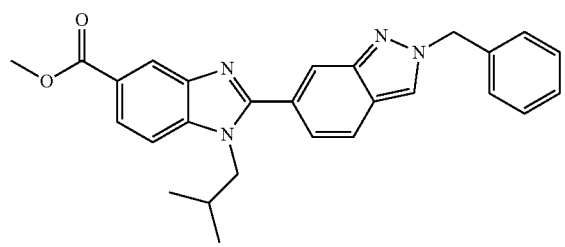
Compound 53
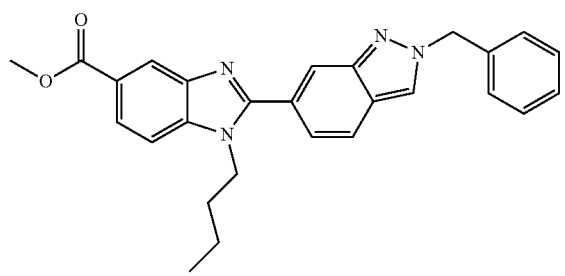

-continued
Compound 54
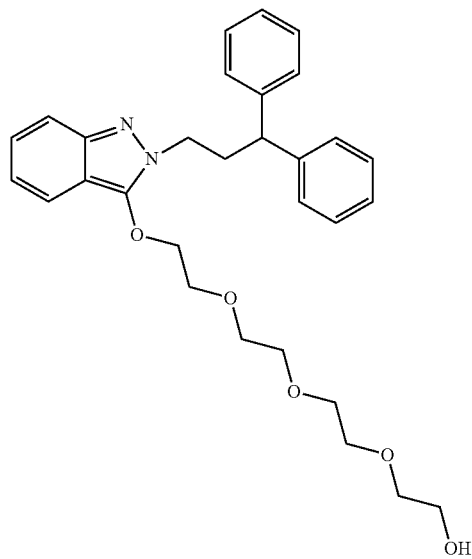
Compound 55
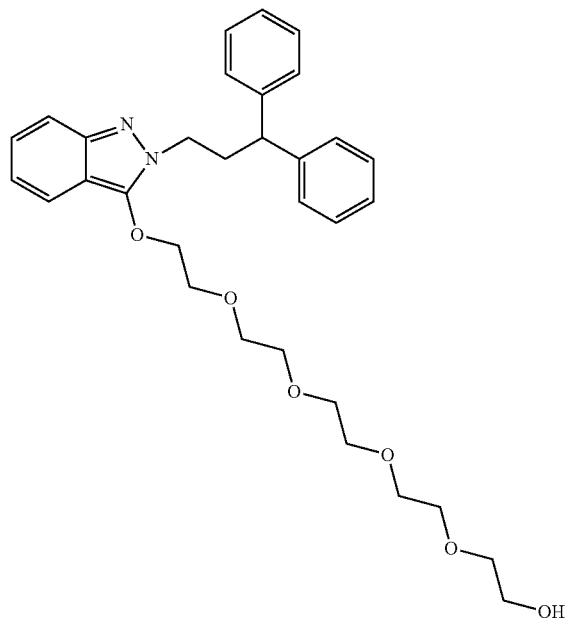
Compound 56
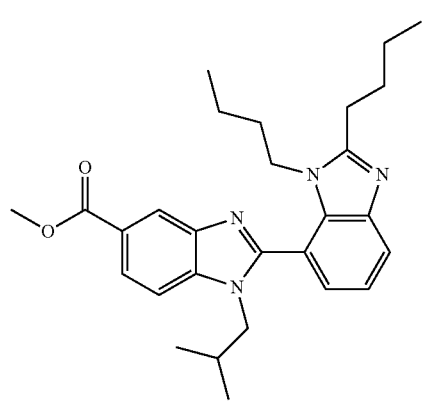
Compound 57
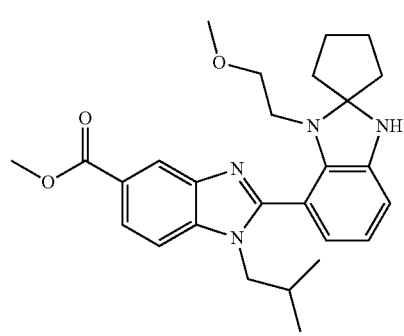
Compound 58
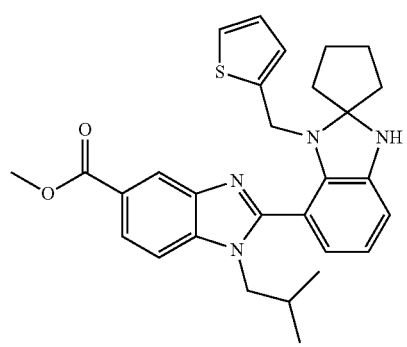
Compound 59
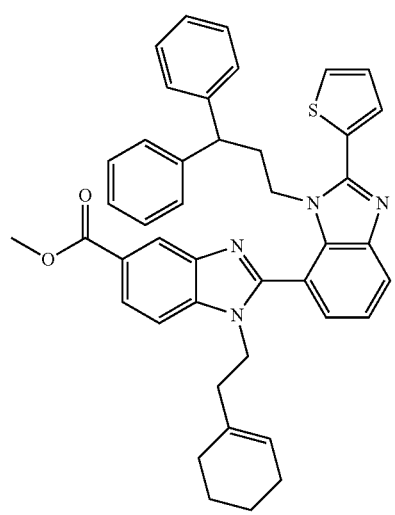

-continued
Compound 60
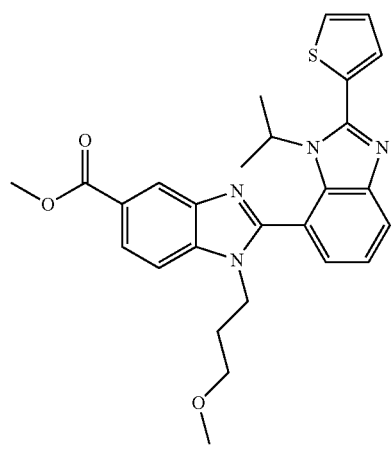
Compound 61
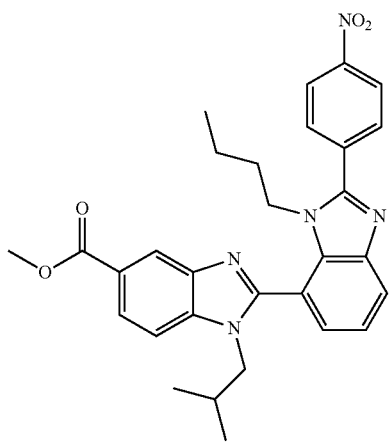
Compound 62
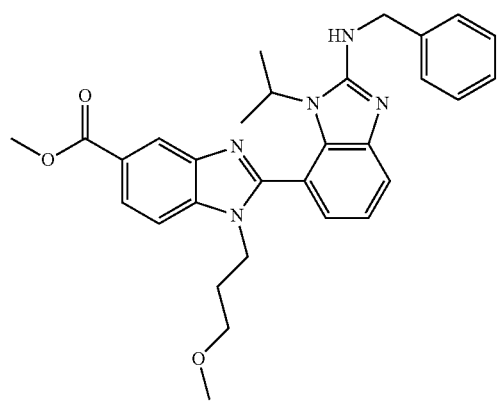
Compound 63
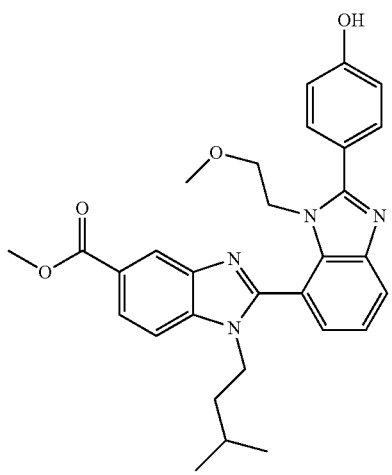
Compound 64
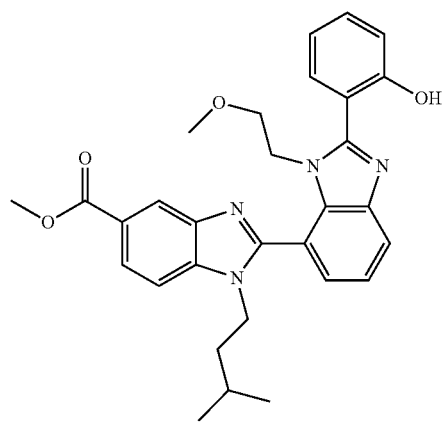
Compound 65
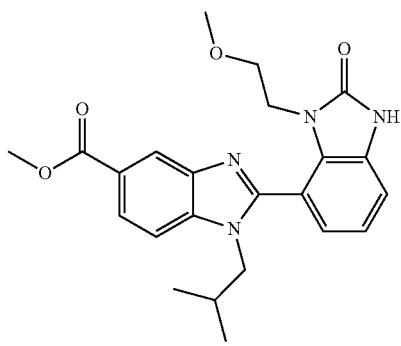

-continued
Compound 66
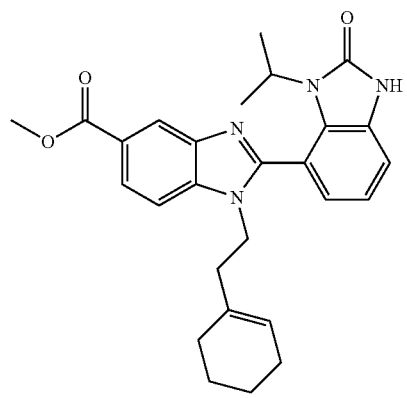
Compound 67
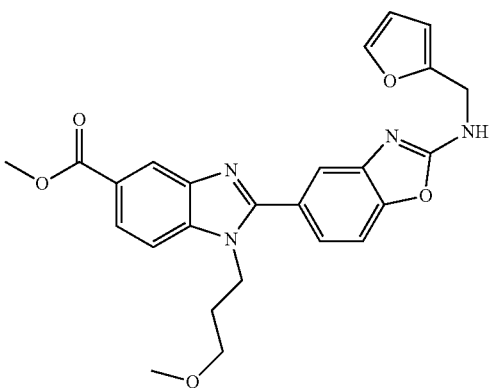
Compound 68
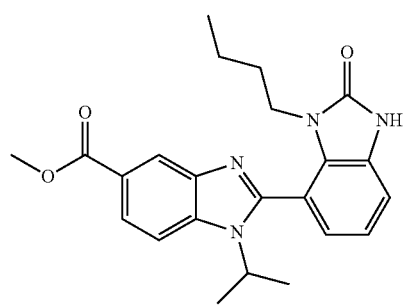
Compound 69
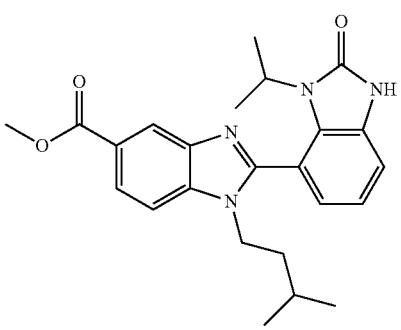
Compound 70
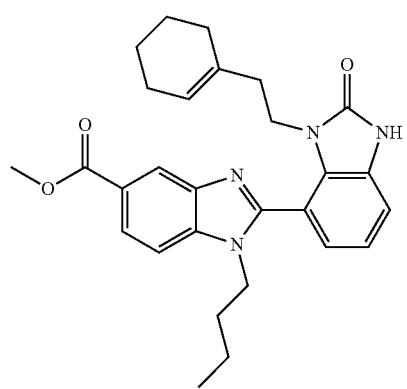
Compound 71
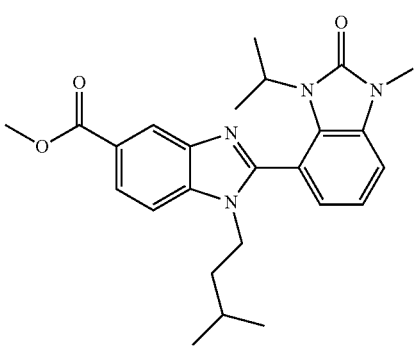
Compound 72
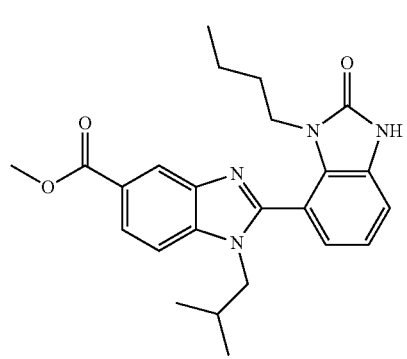
Compound 73
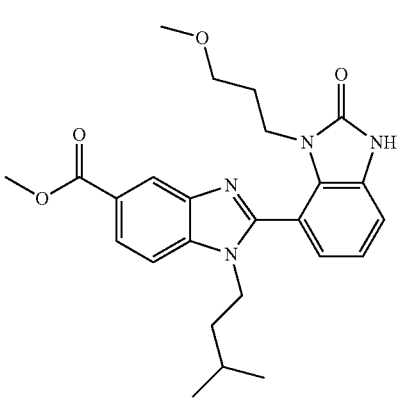

-continued
Compound 74
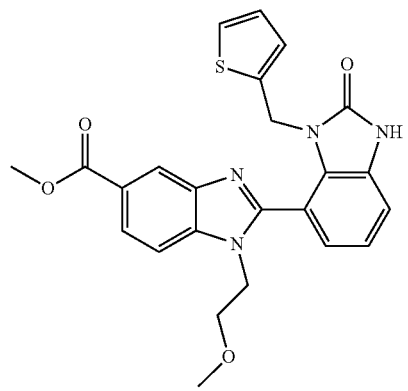
Compound 75
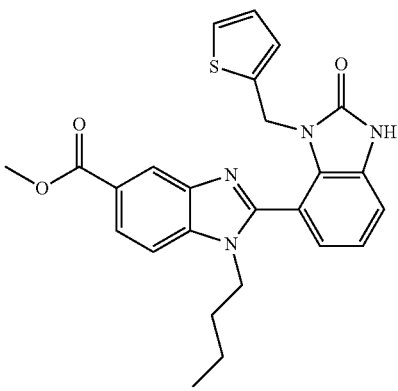
Compound 76
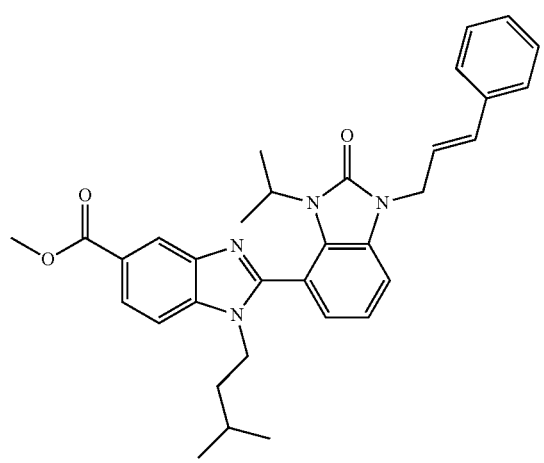
Compound 77
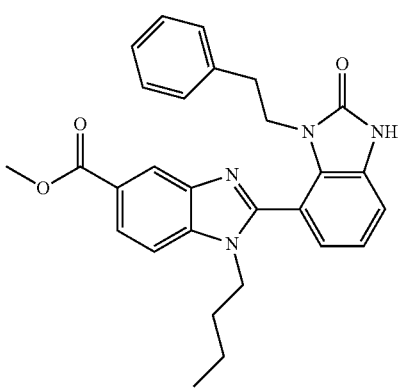
Compound 78
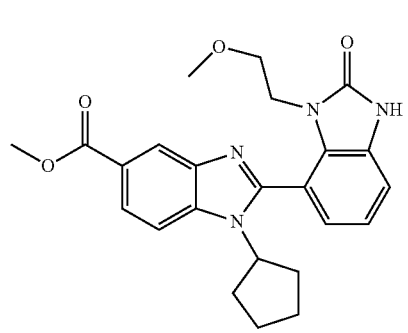
Compound 79
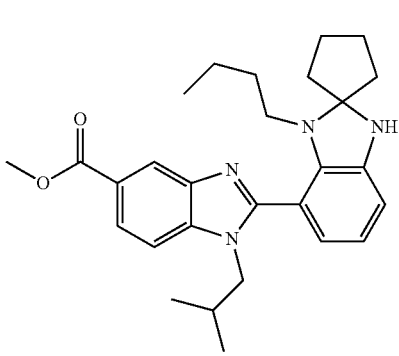
Compound 80
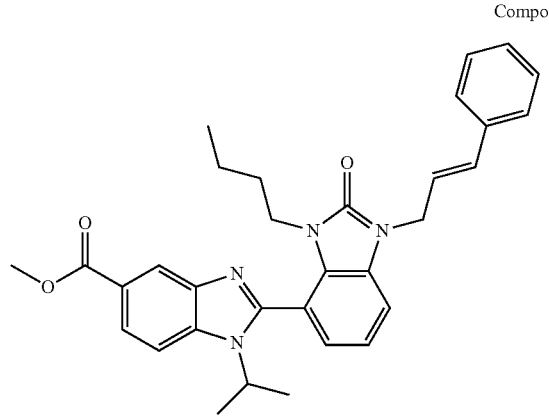
Compound 81
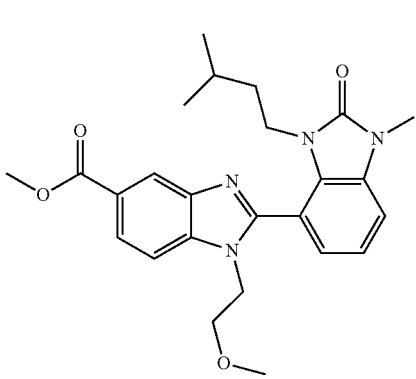

-continued
Compound 82
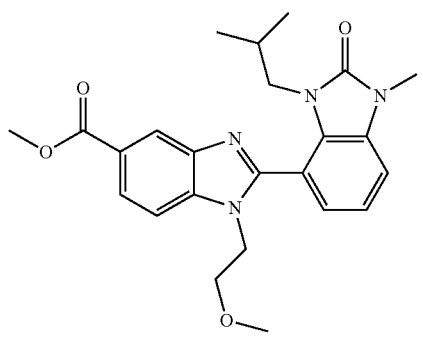
Compound 83
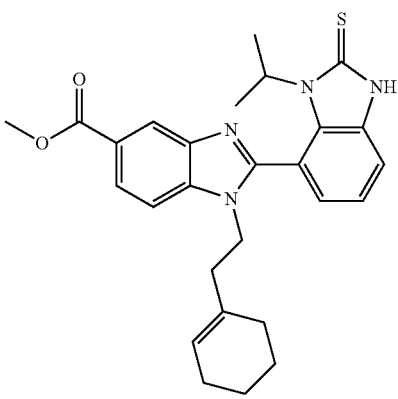
Compound 84
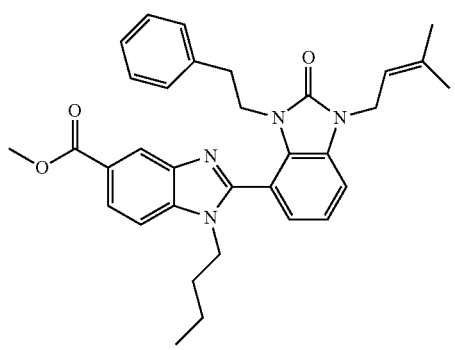
Compound 85
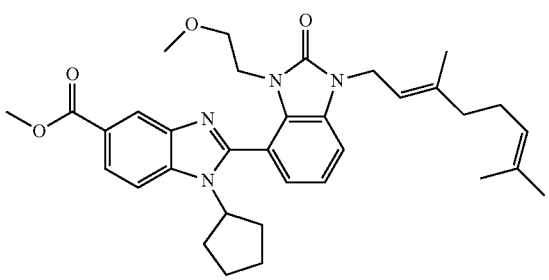
Compound 86
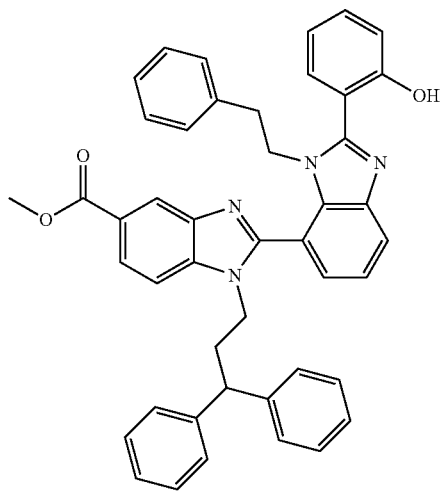
Compound 87
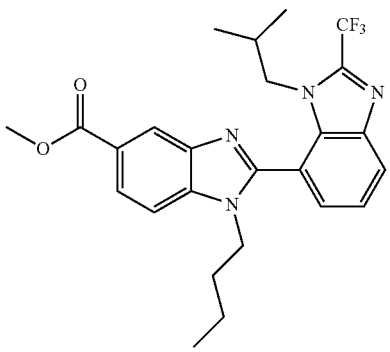
Compound 88
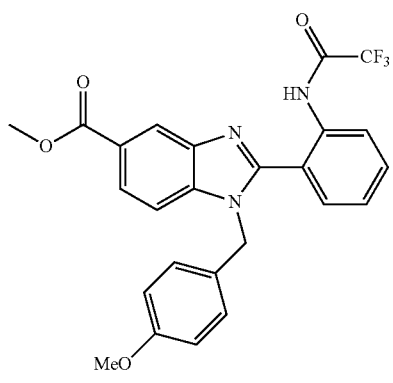
Compound 89
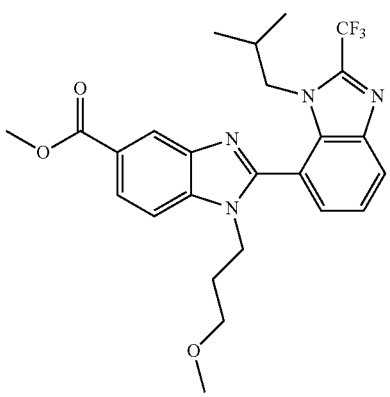

-continued
Compound 90
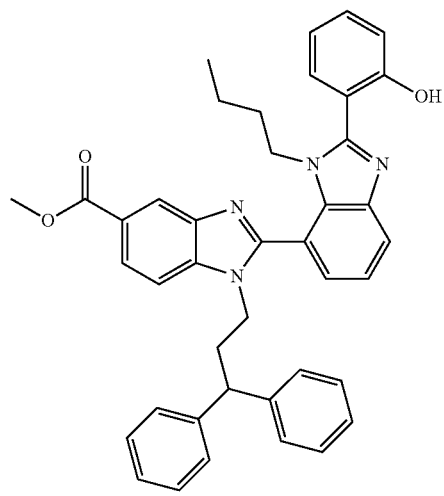
Compound 91
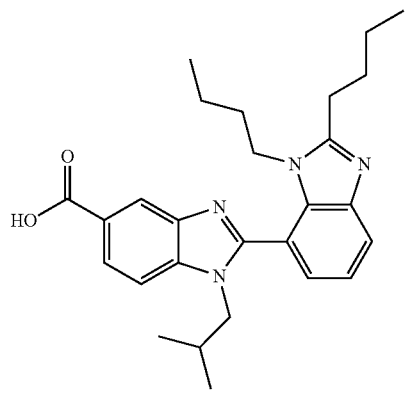
Compound 92
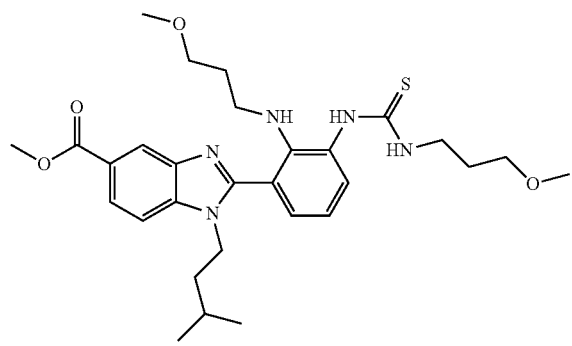
Compound 93
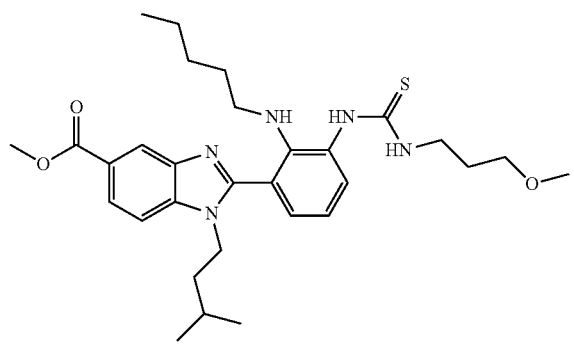
Compound 94
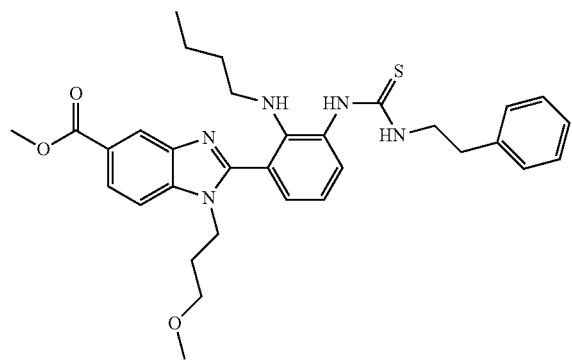
Compound 95
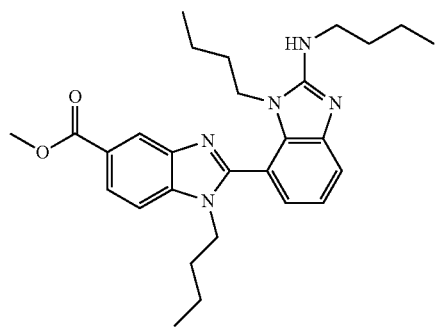

-continued
Compound 96
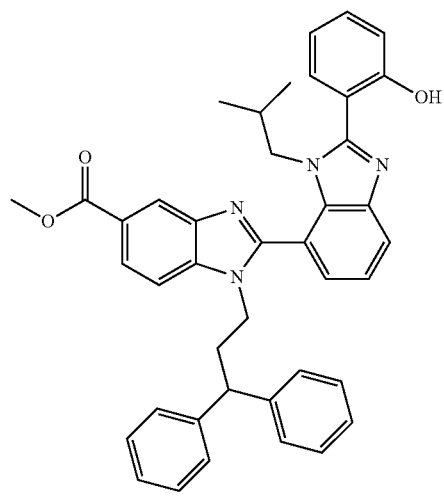
Compound 97
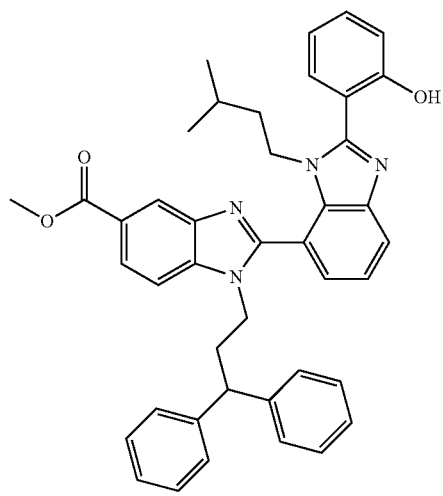
Compound 98
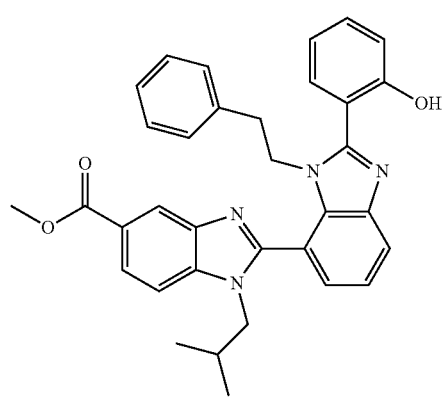
Compound 99
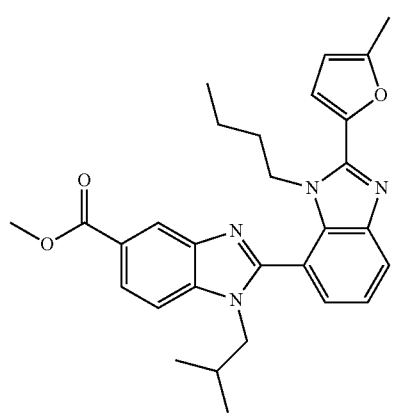
Compound 100
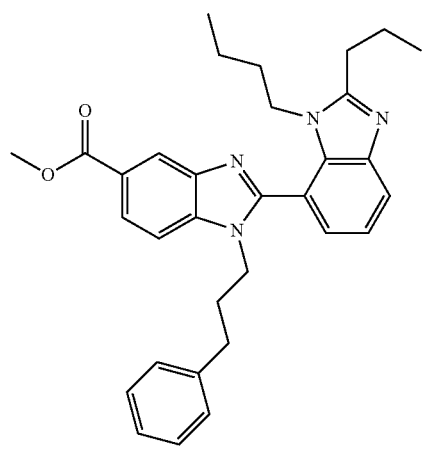
Compound 101
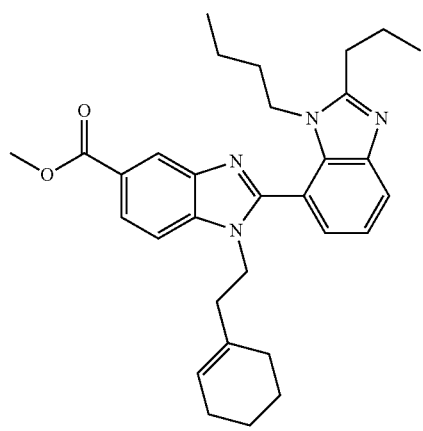

-continued
Compound 102
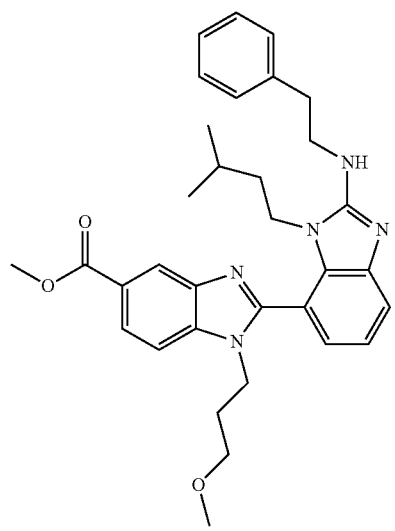
Compound 103
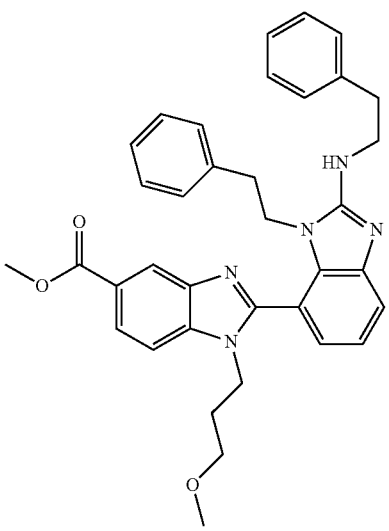
Compound 104
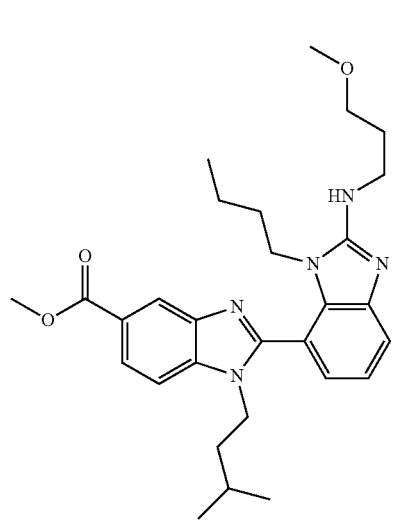
Compound 105
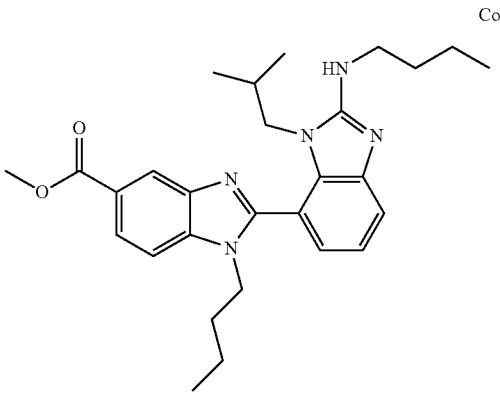
Compound 106
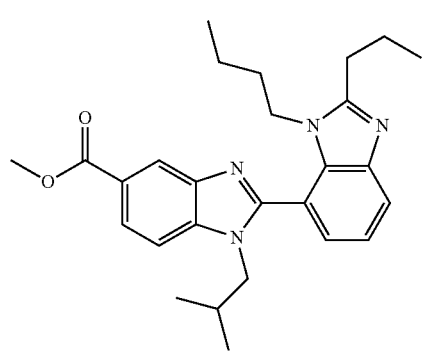
Compound 107
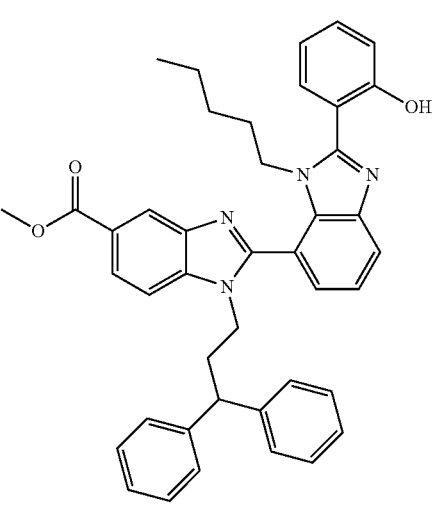

-continued
Compound 108
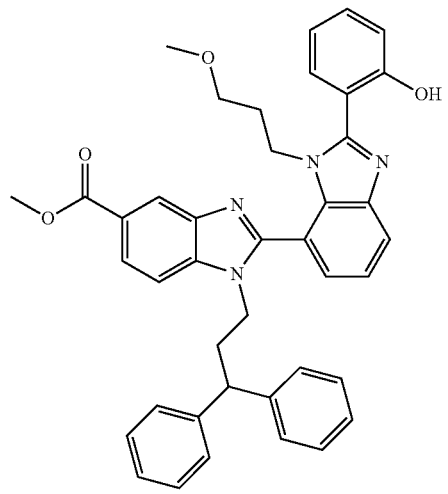
Compound 109
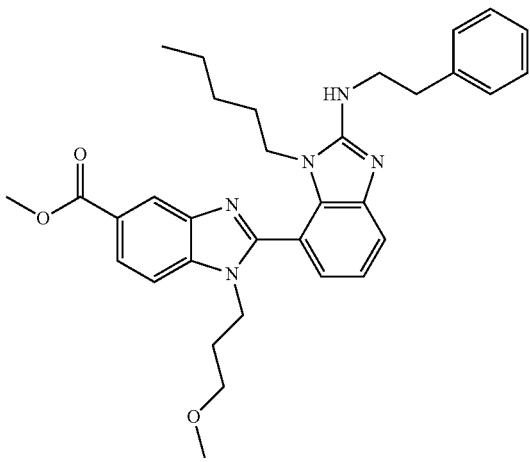
Compound 110
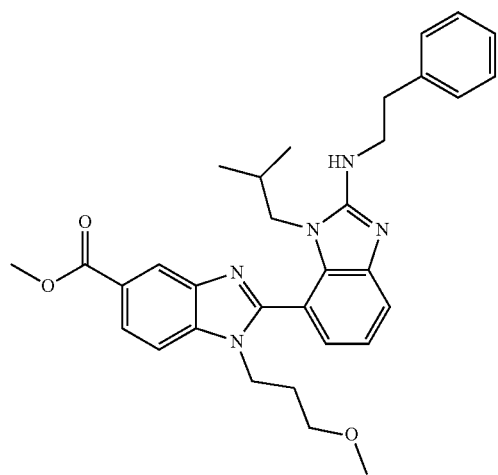
Compound 111
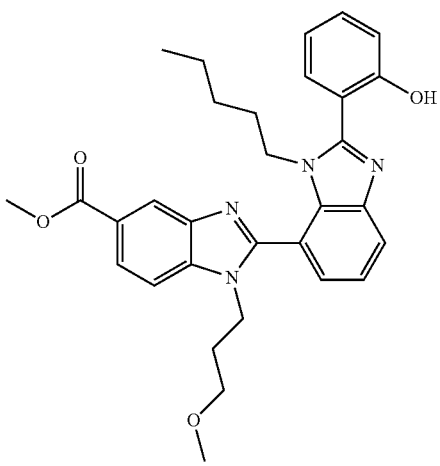
Compound 112
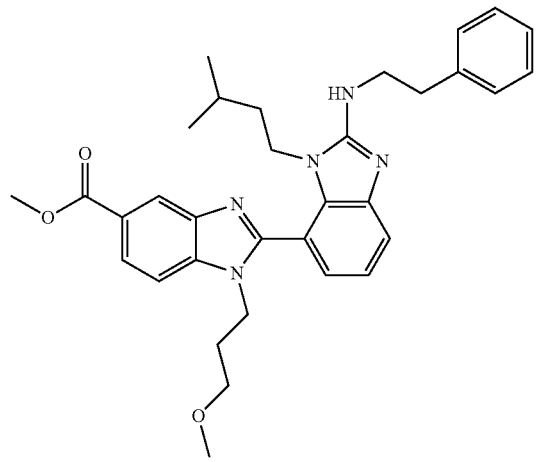
Compound 113
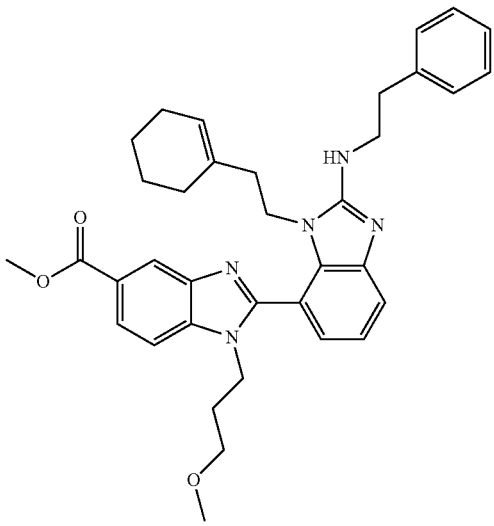

-continued
Compound 114
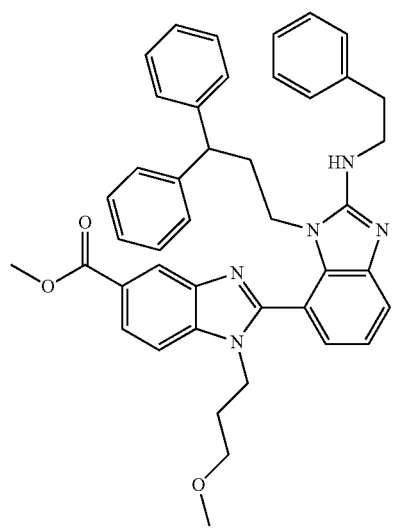
Compound 115
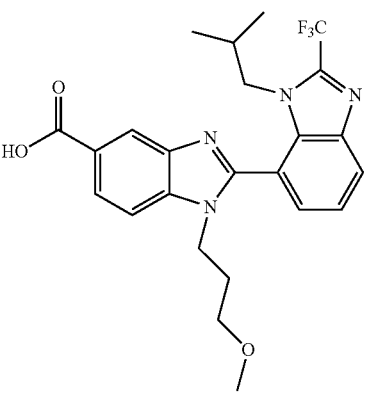
Compound 116
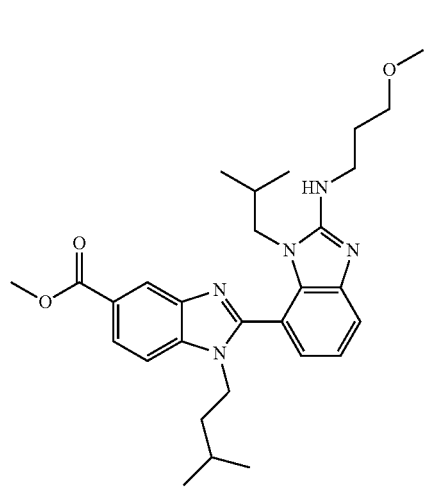
Compound 117
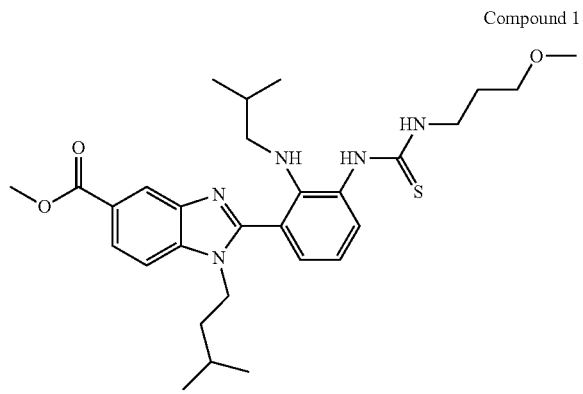
Compound 118
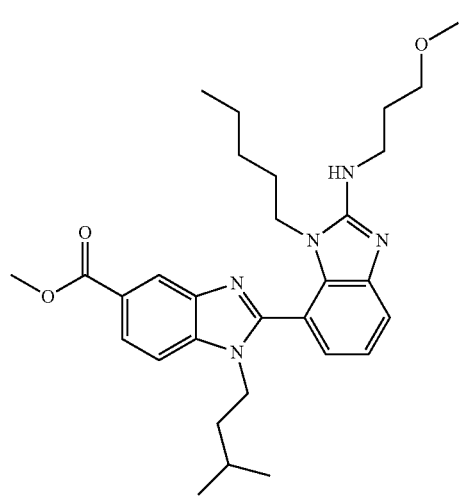
Compound 119
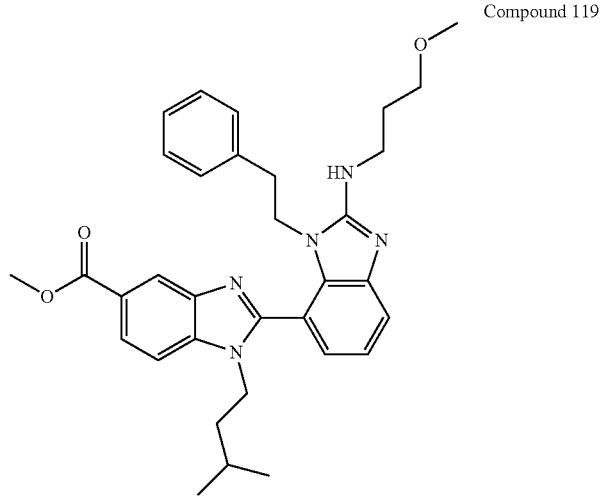

-continued
Compound 120
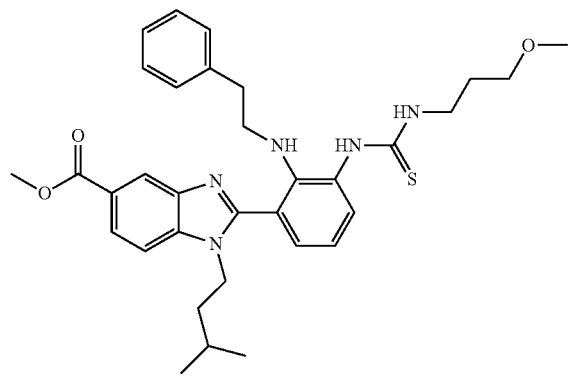
Compound 121
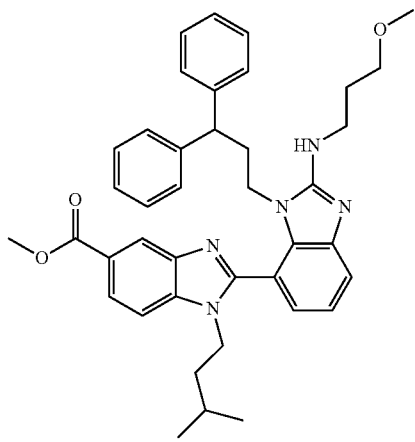
Compound 122
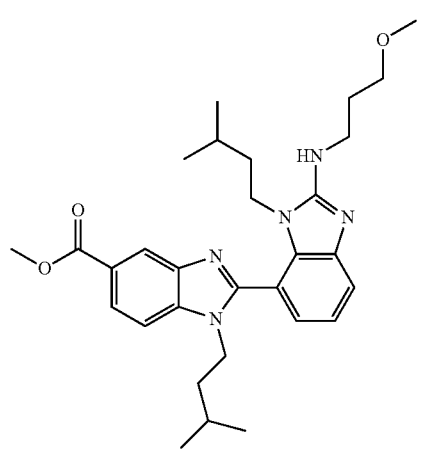
Compound 123
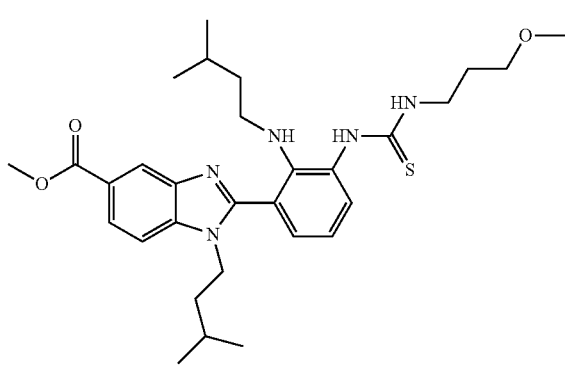
Compound 124
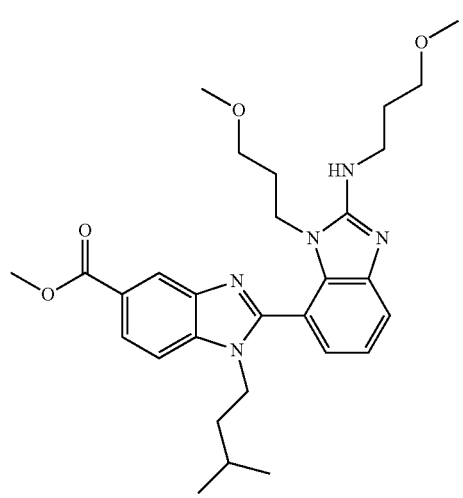
Compound 125
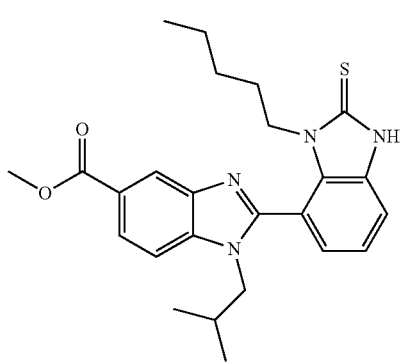

-continued
Compound 126
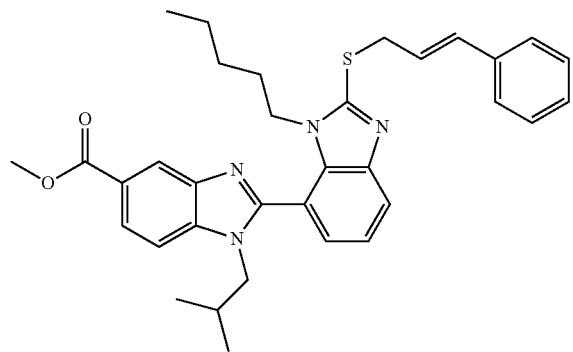
Compound 127
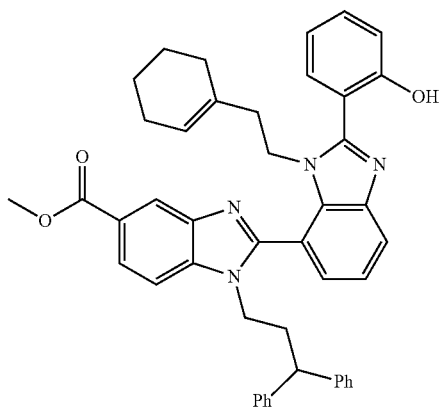
Compound 128
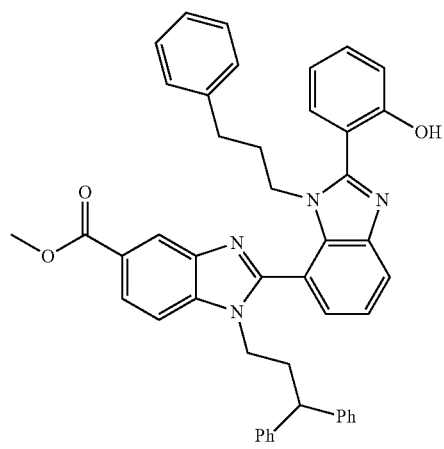
Compound 129
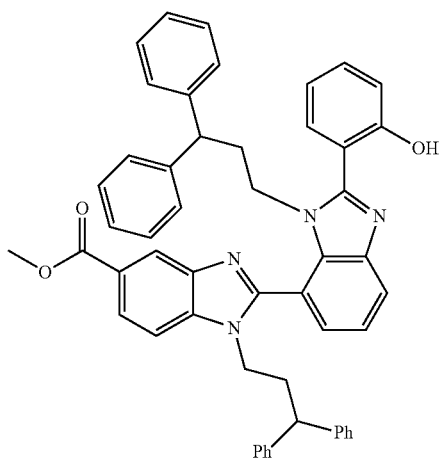
Compound 130
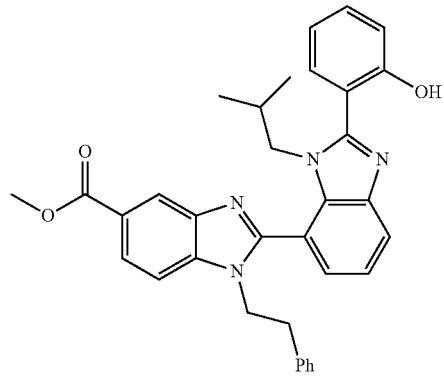
Compound 131
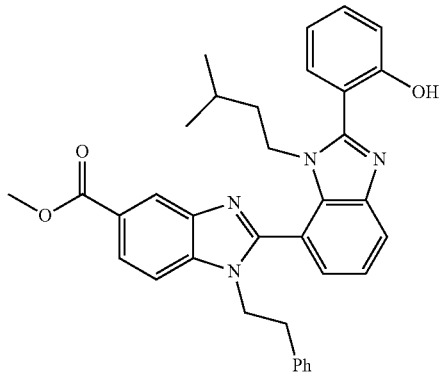
Compound 132
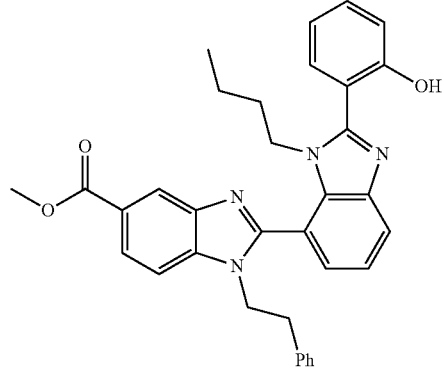
Compound 133
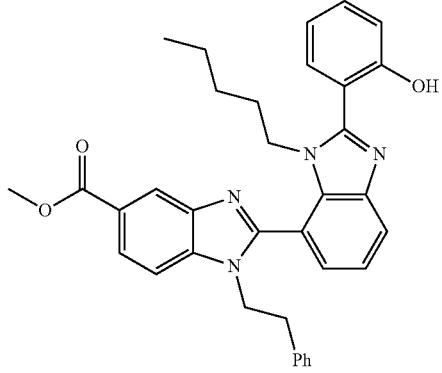

-continued
Compound 134
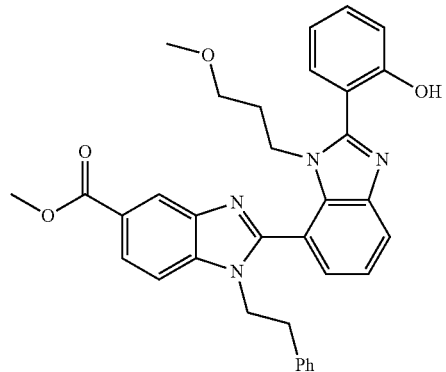
Compound 135
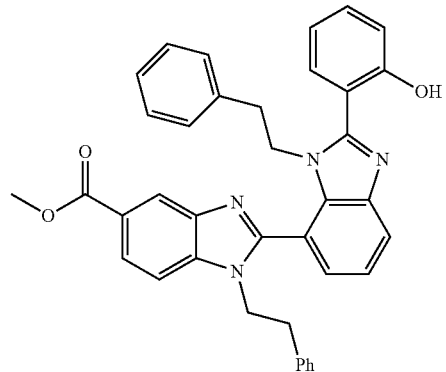
Compound 136
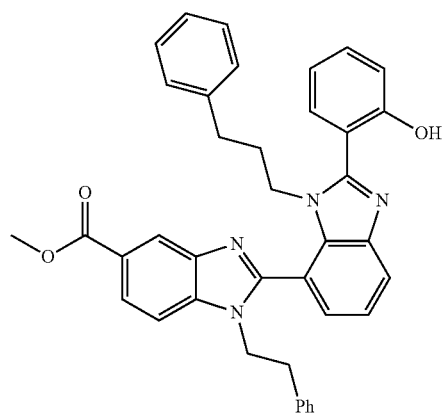
Compound 137
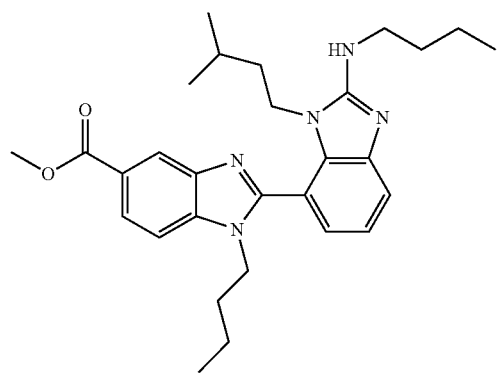
Compound 138
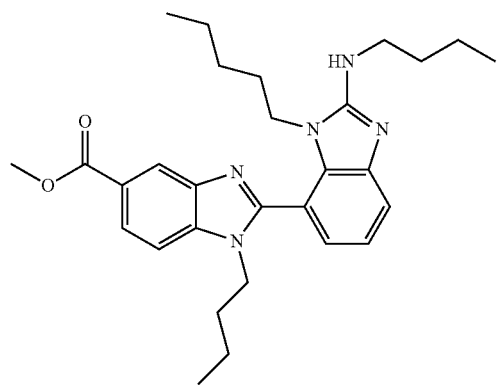
Compound 139
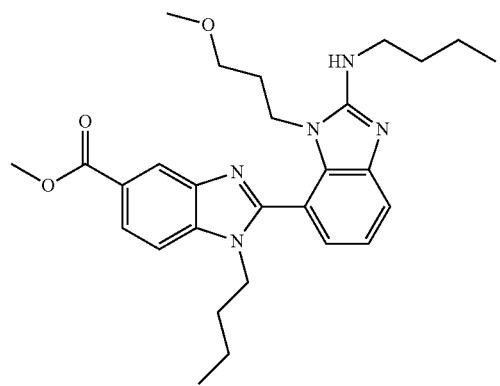
Compound 140
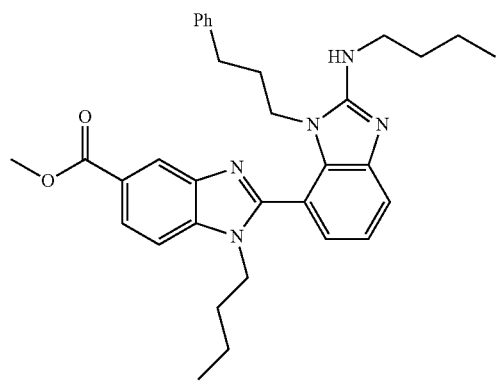
Compound 141
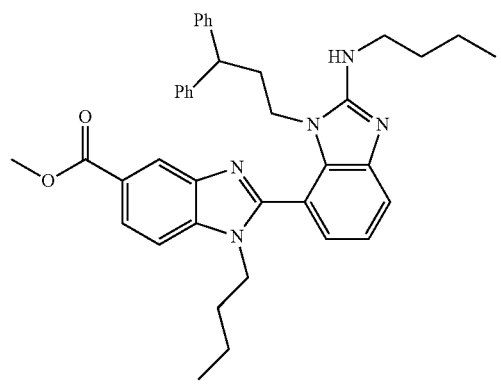

-continued
Compound 142
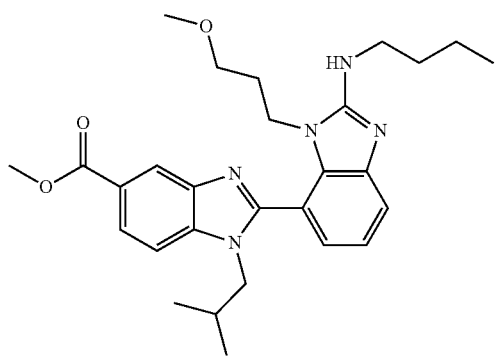
Compound 143
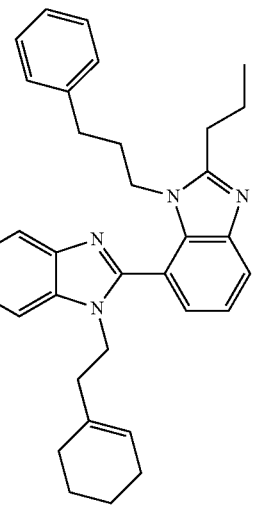
Compound 144
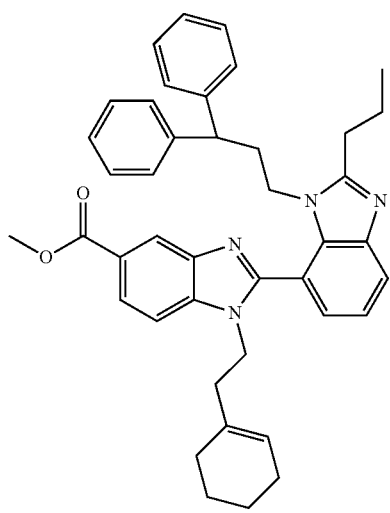
Compound 145
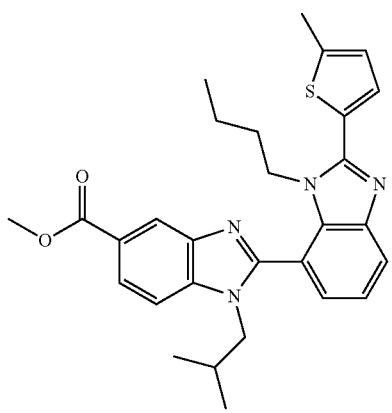
Compound 146
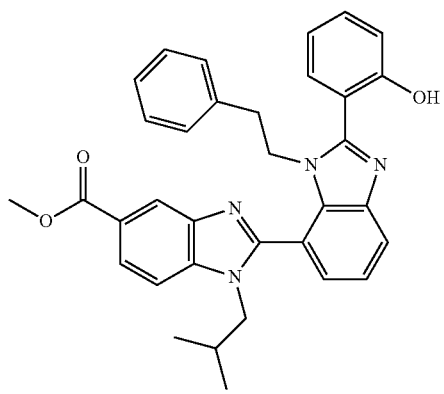
Compound 147
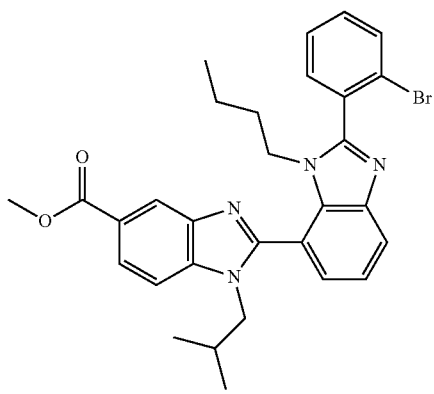

-continued
Compound 148
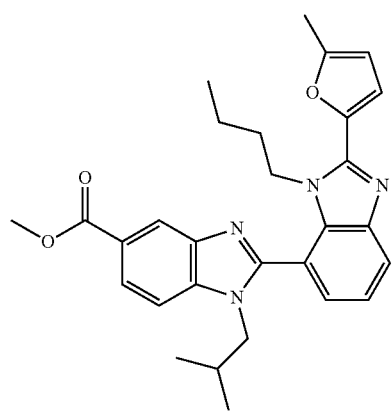
Compound 149
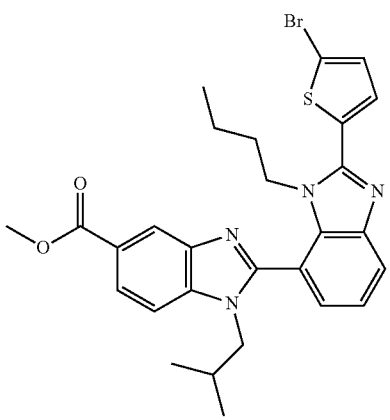
Compound 150
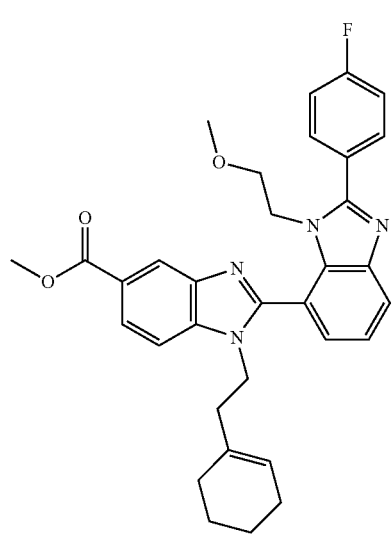
Compound 151
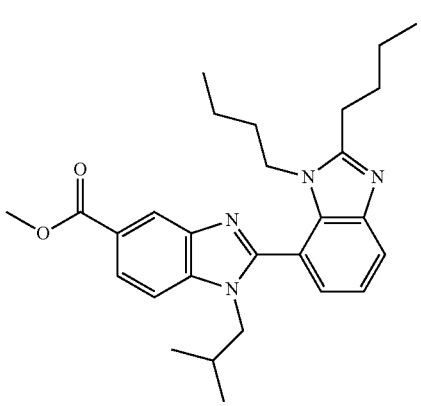
Compound 152
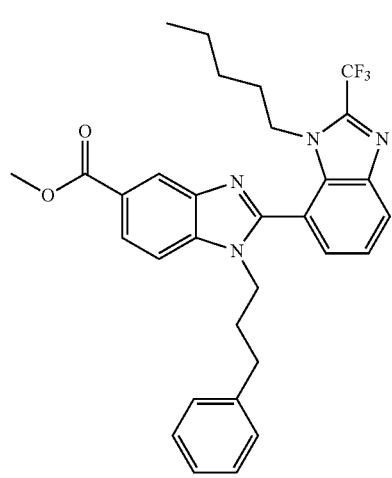
Compound 153
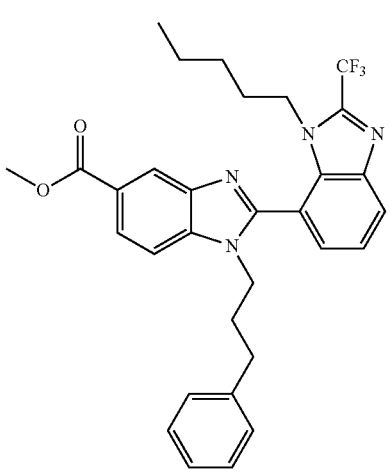

-continued
Compound 154
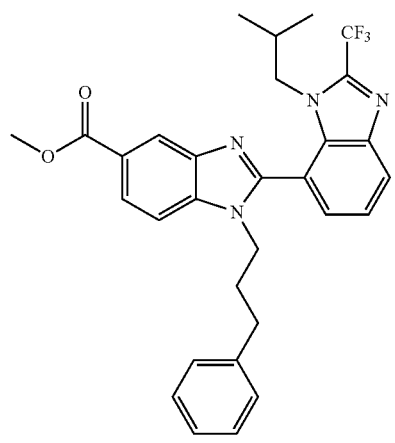
Compound 155
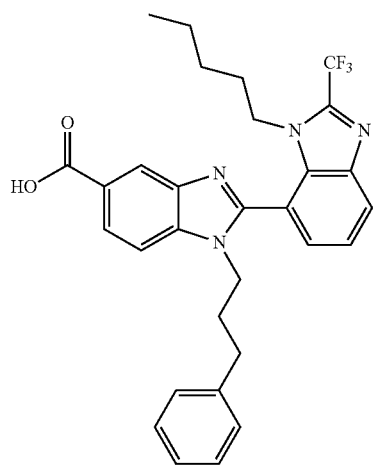
Compound 156
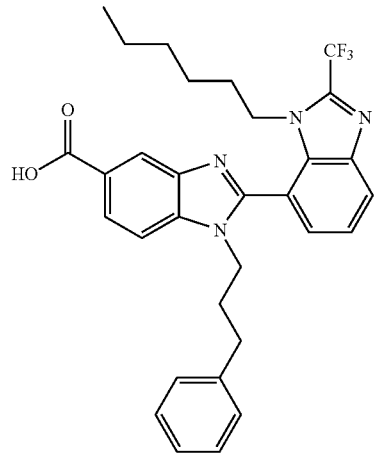
Compound 157
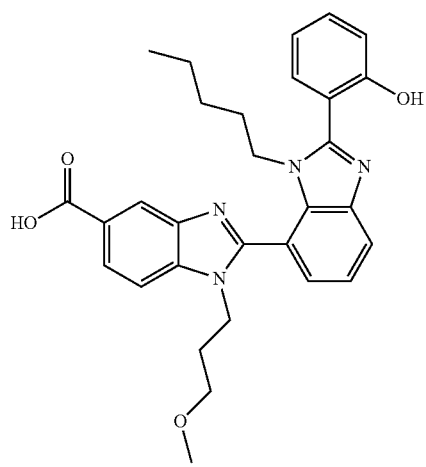
Compound 158
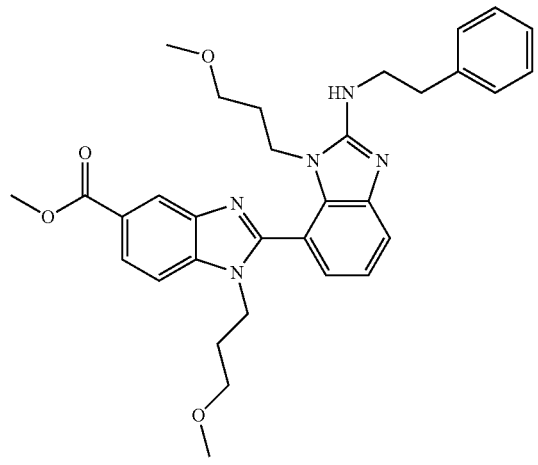
Compound 159
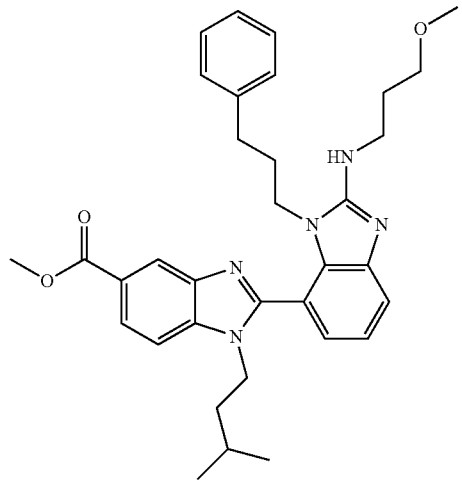

-continued
Compound 160
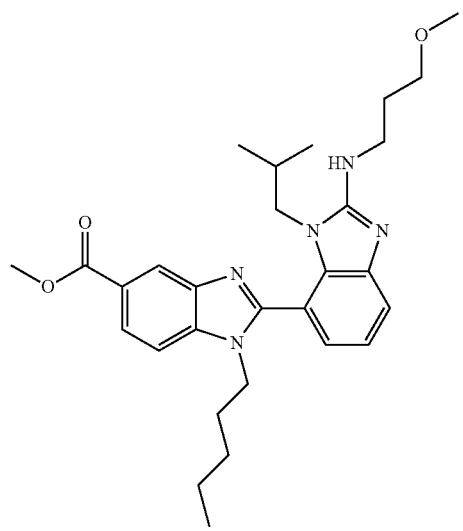
Compound 161
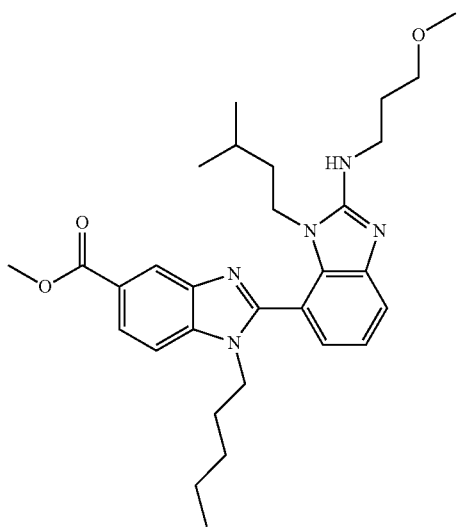
Compound 162
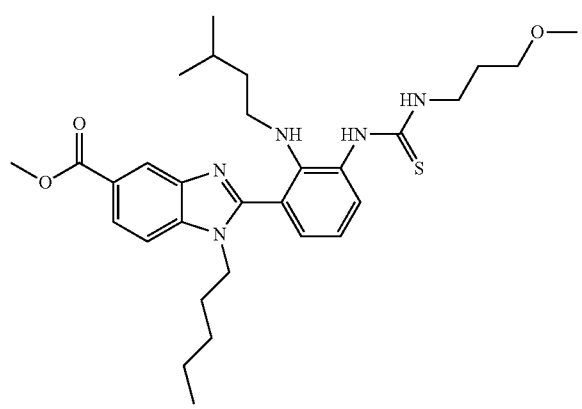
Compound 163
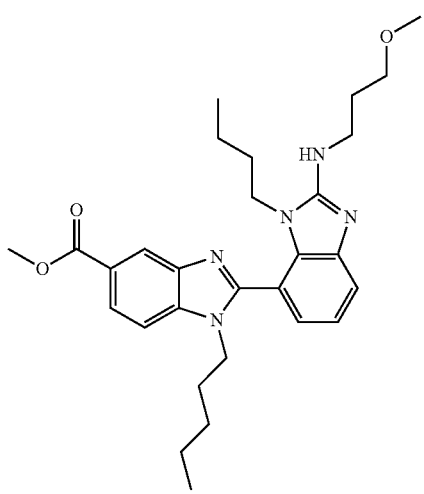
Compound 164
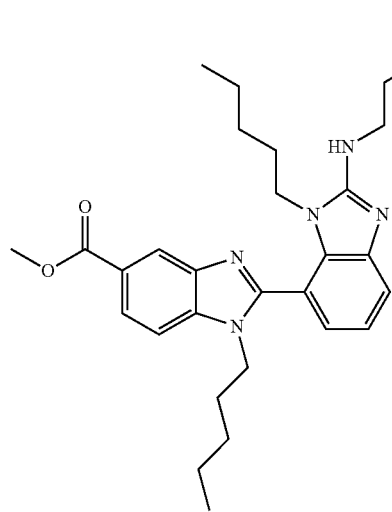
Compound 165
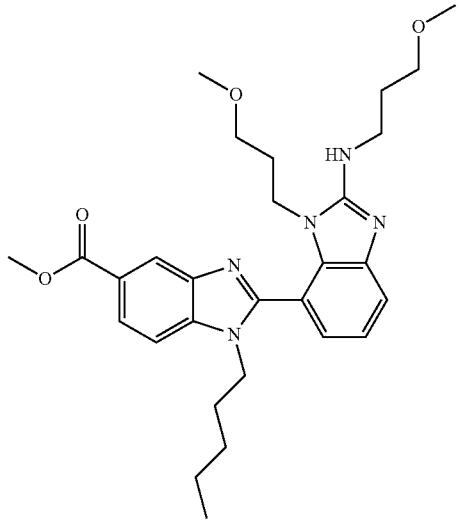

-continued
Compound 166
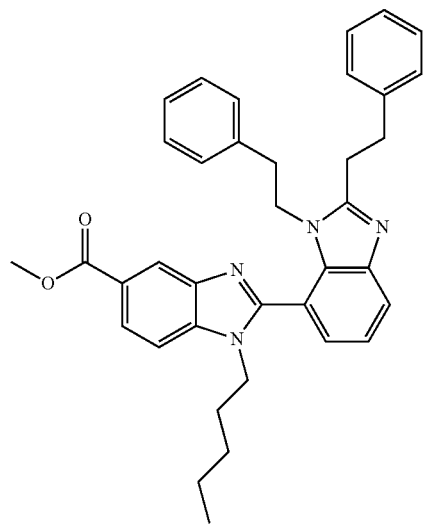
Compound 167
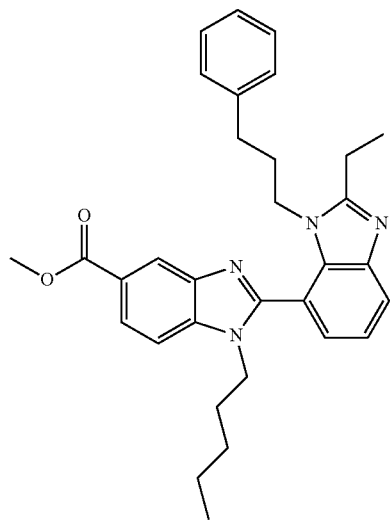
Compound 168
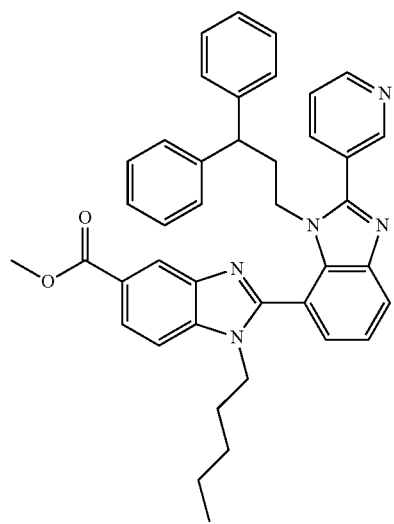
Compound 169
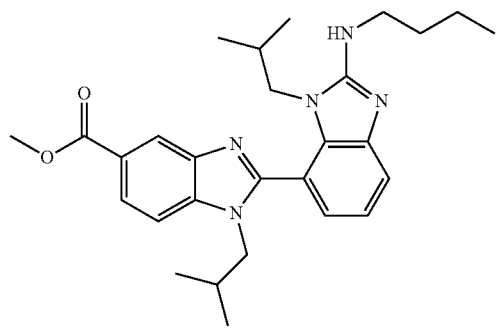
Compound 170
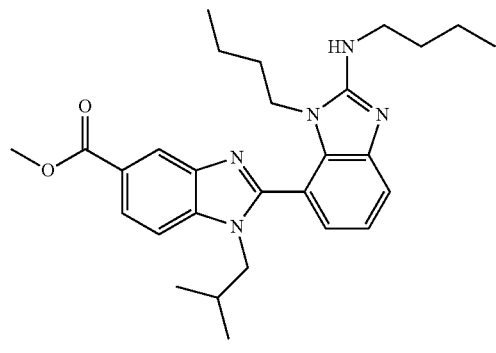
Compound 171
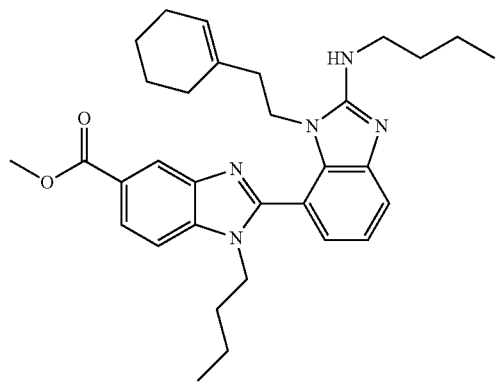

-continued
Compound 172
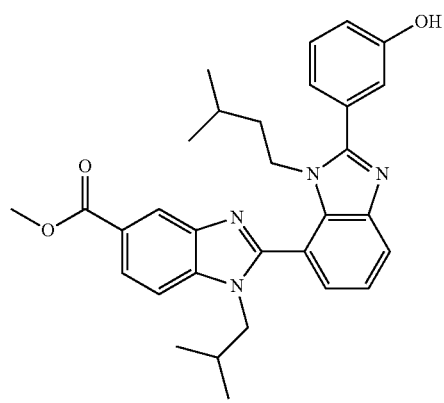
Compound 173
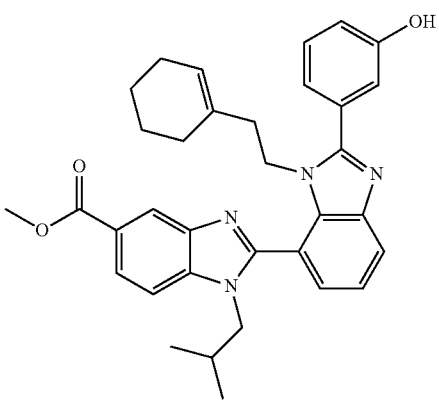
Compound 174
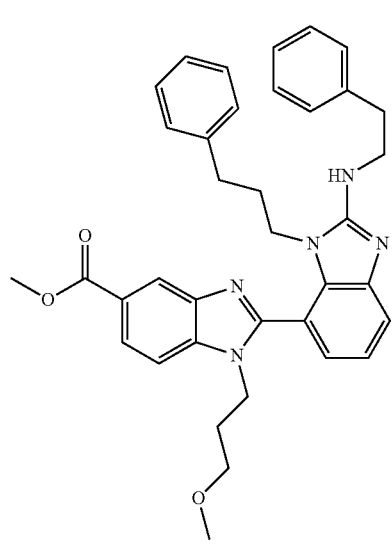
Compound 175
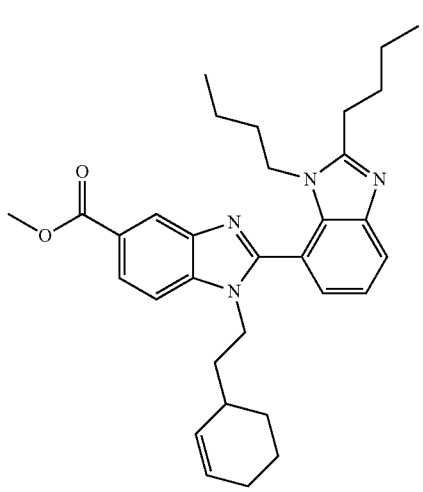
Compound 176
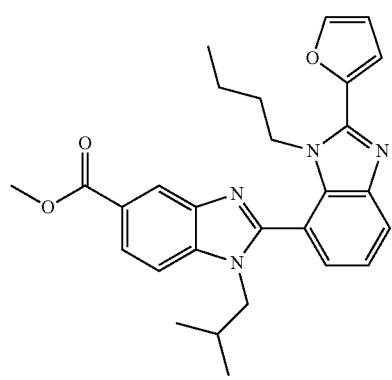
Compound 177
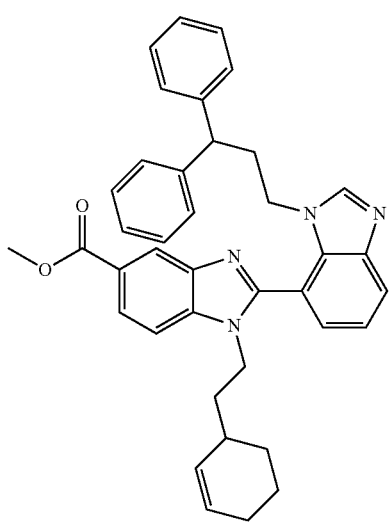

-continued
Compound 178
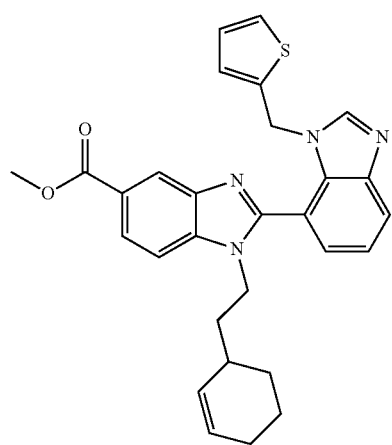
Compound 179
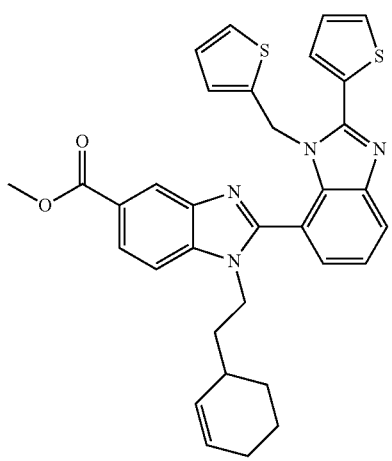
Compound 180
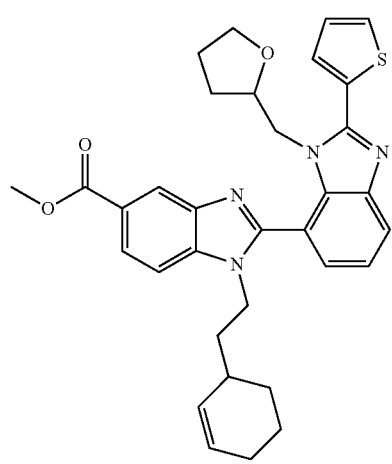
Compound 181
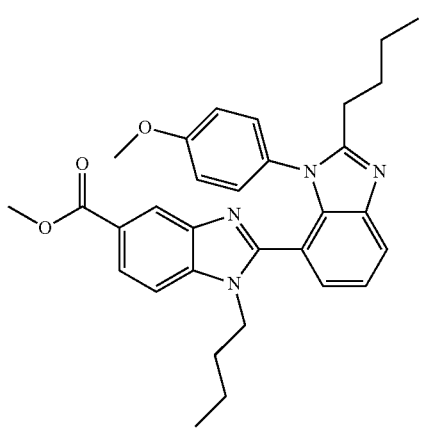
Compound 182
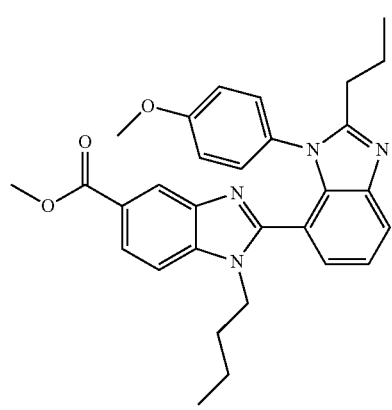
Compound 183
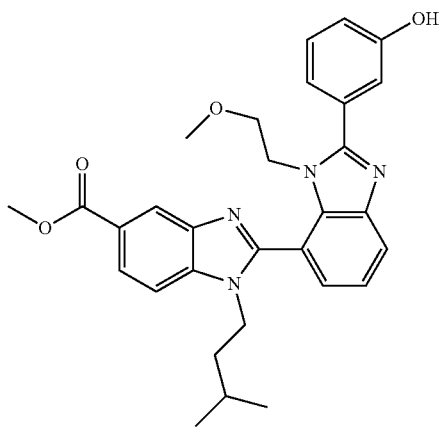

-continued
Compound 184
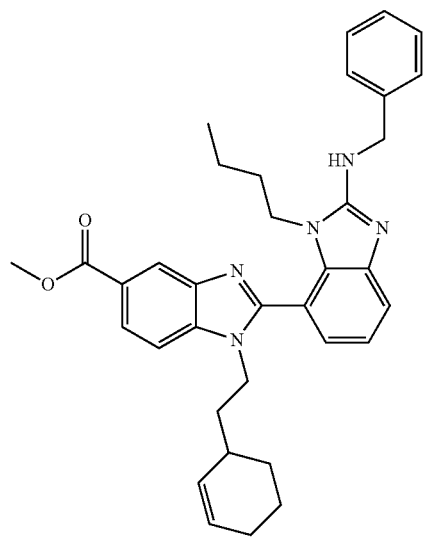
Compound 185
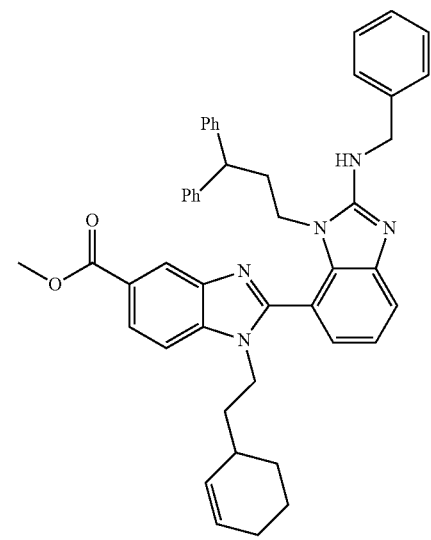
Compound 186
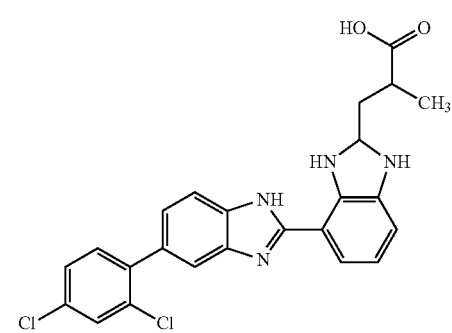
Compound 187
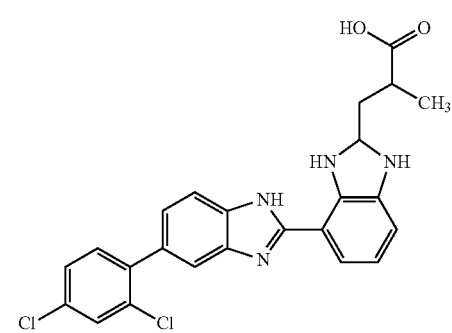
Compound 188
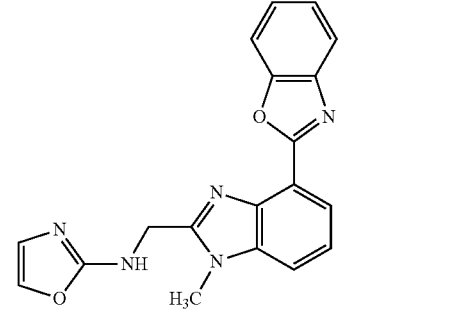
Compound 189
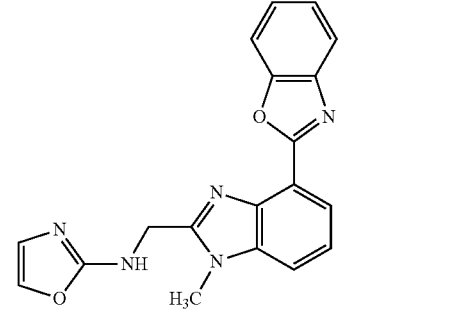
Compound 190
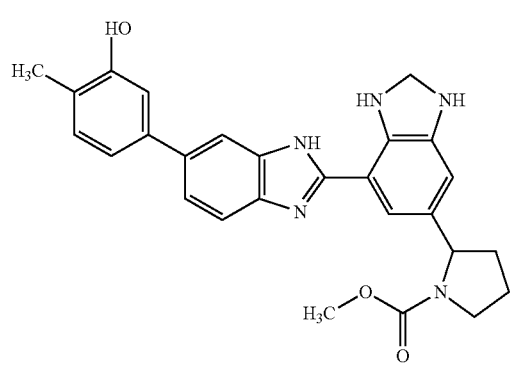
Compound 191
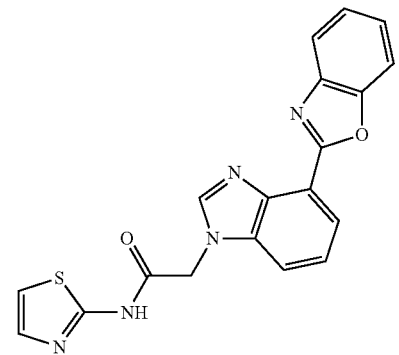

-continued
Compound 192
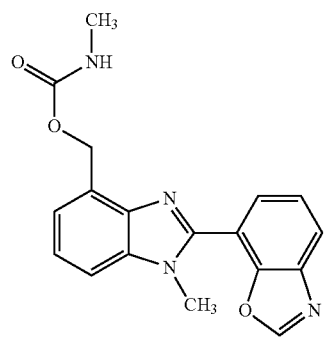
Compound 193
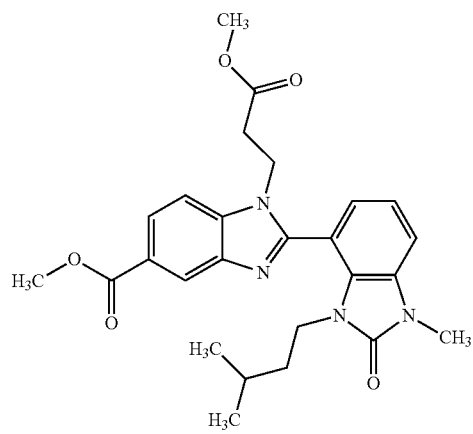
Compound 194
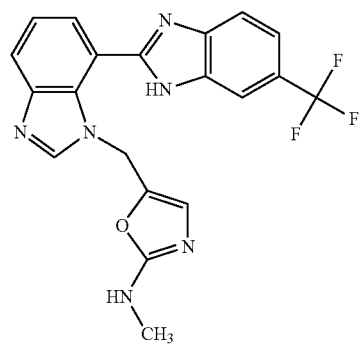
Compound 195
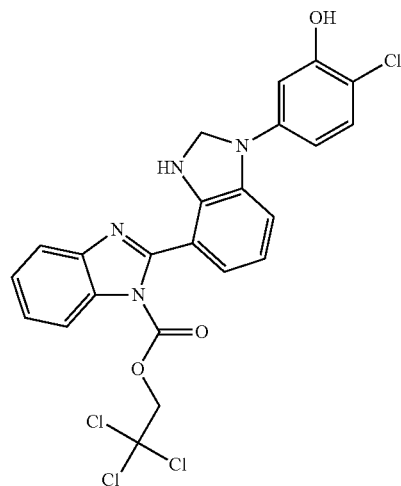
Compound 196
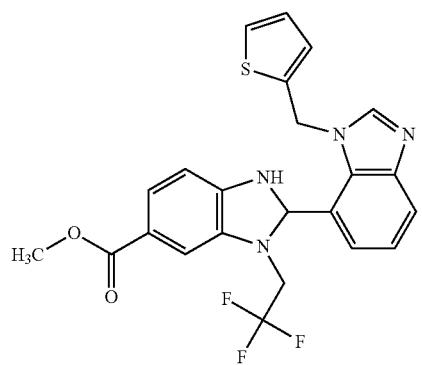
Compound 197
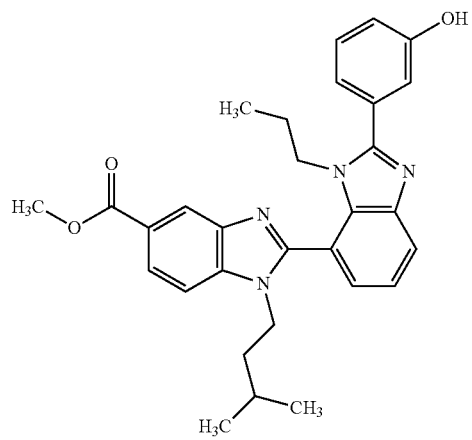

-continued
Compound 198
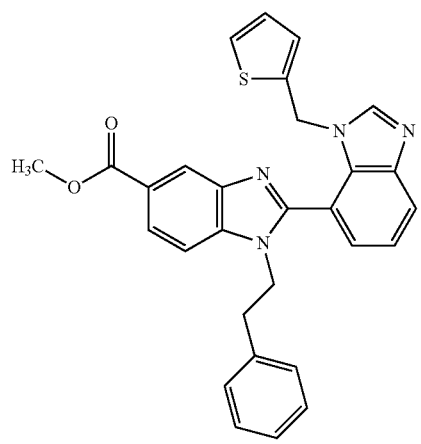
Compound 199
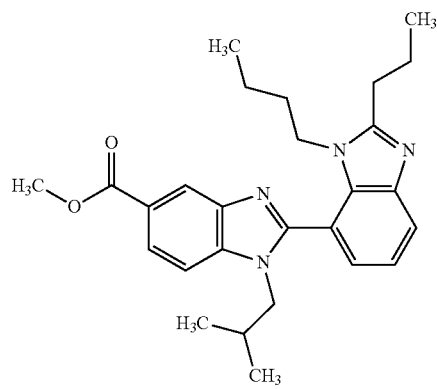
Compound 200
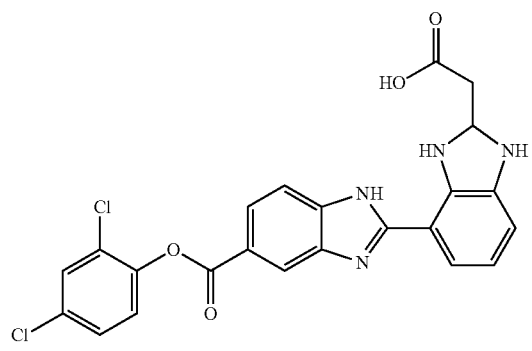
Compound 201
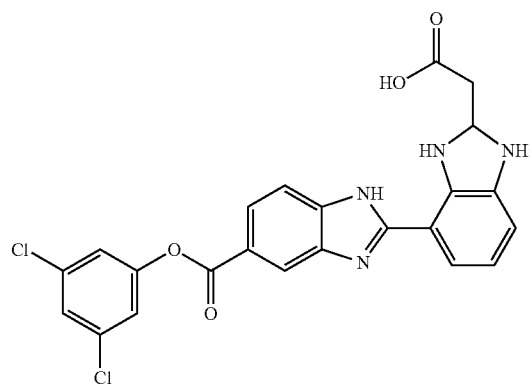
Compound 202
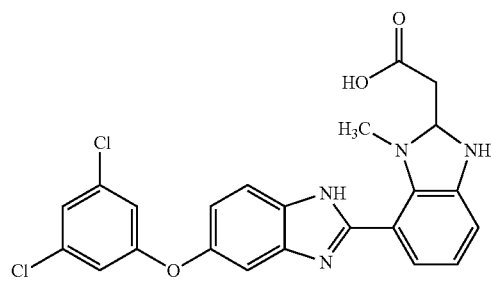
Compound 203
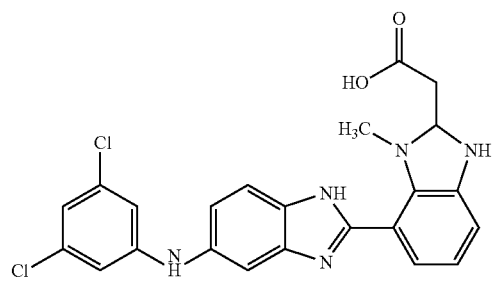
Compound 204
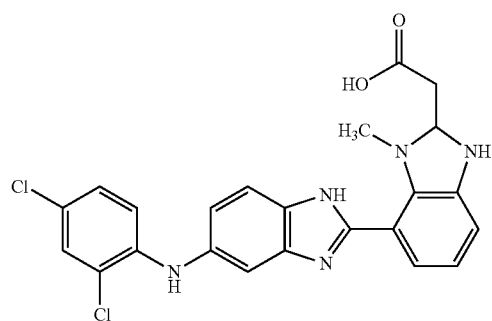
Compound 205
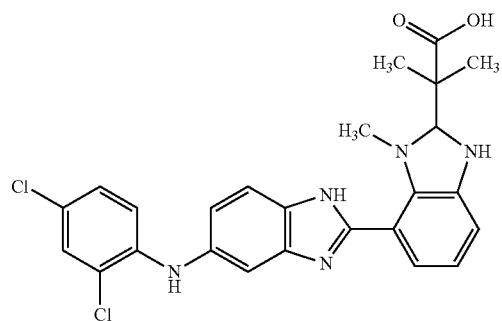

Compound 206
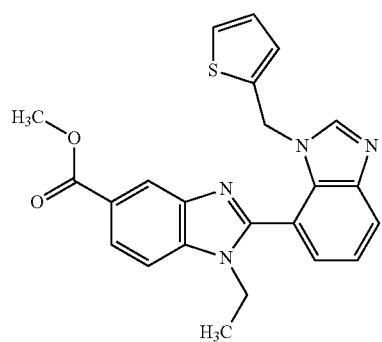
Compound 207
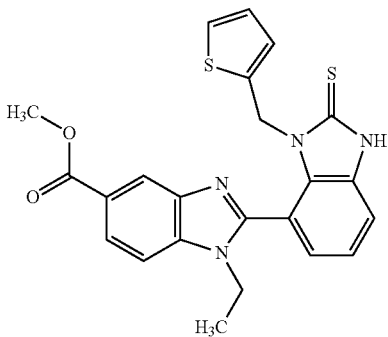
Compound 208
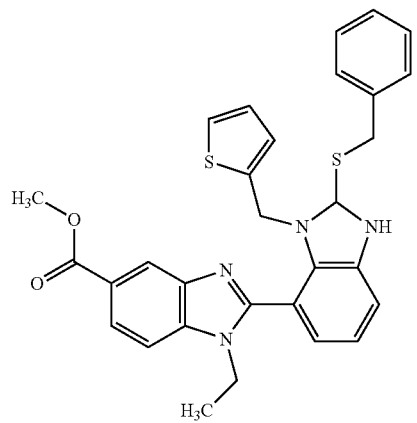
Compound 209
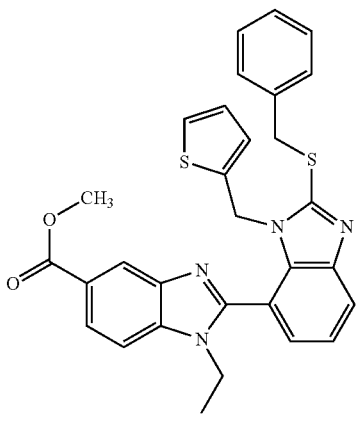
Compound 210
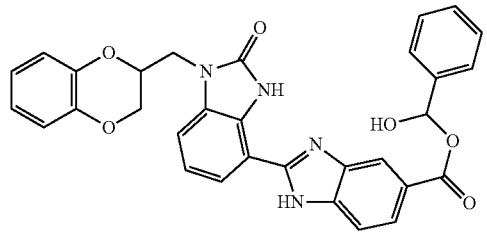
Compound 211
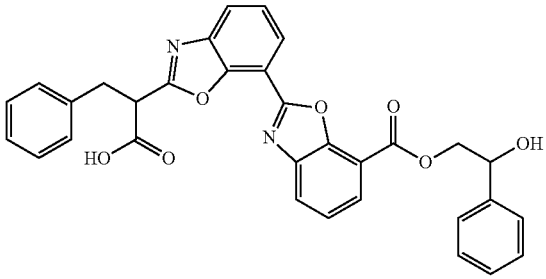
Compound 212
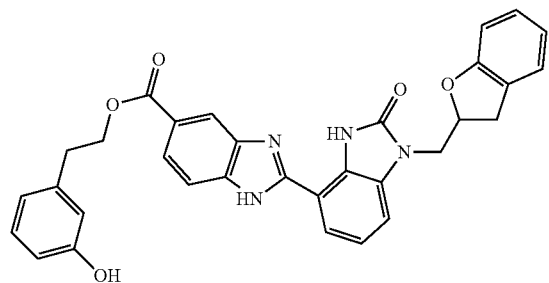
Compound 213
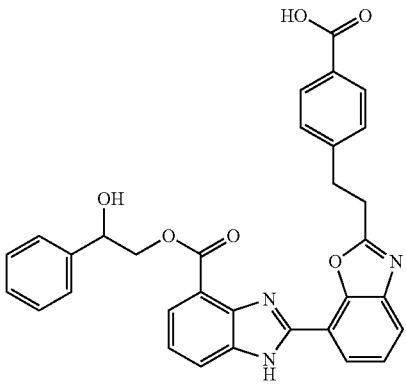

Compound 214
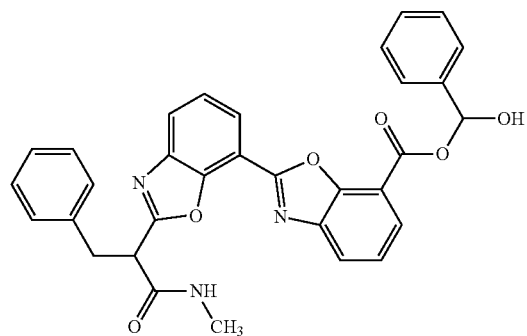
Compound 215
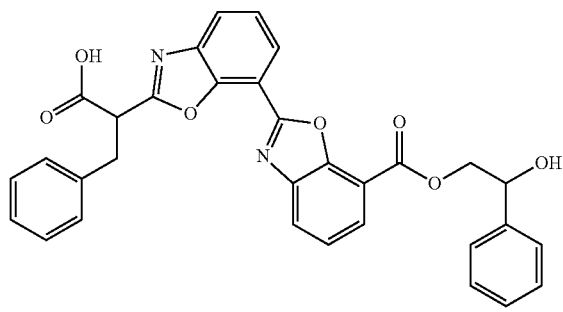
Compound 216
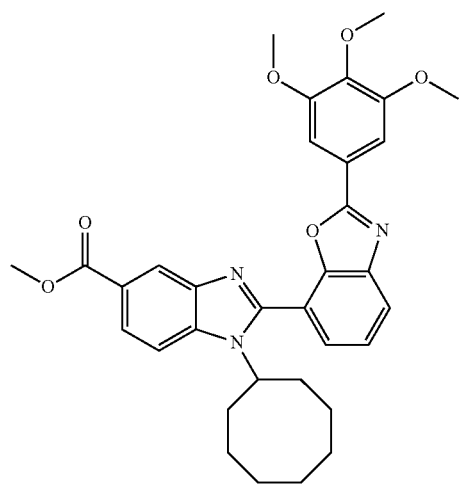
Compound 217
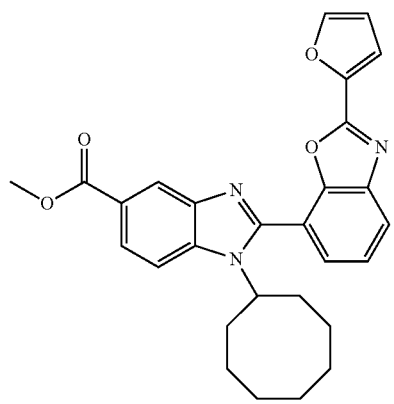
Compound 218
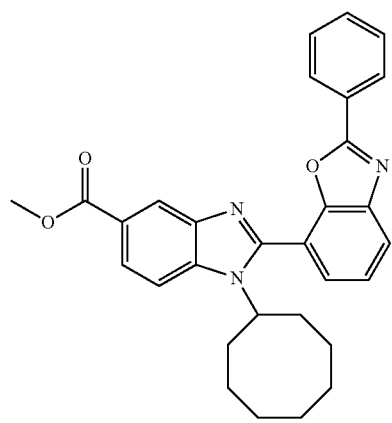
Compound 219
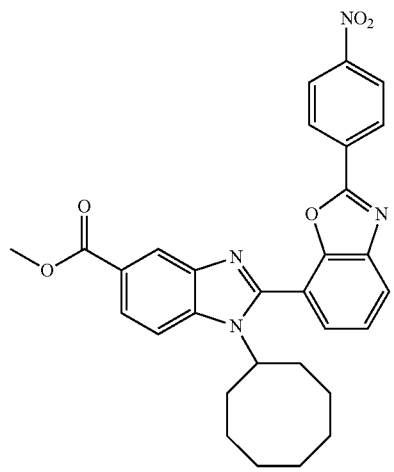

-continued
Compound 220
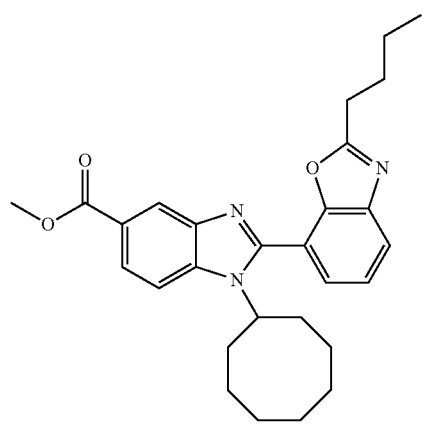
Compound 221
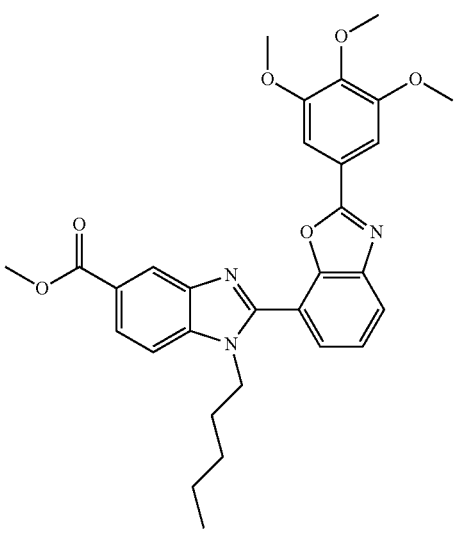
Compound 222
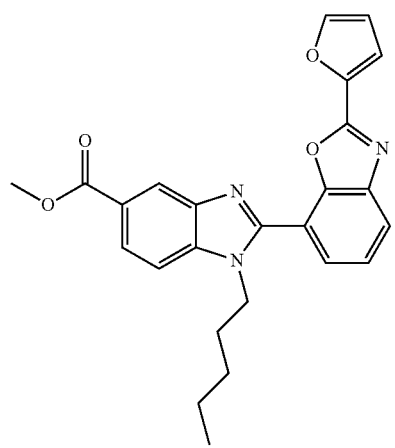
Compound 223
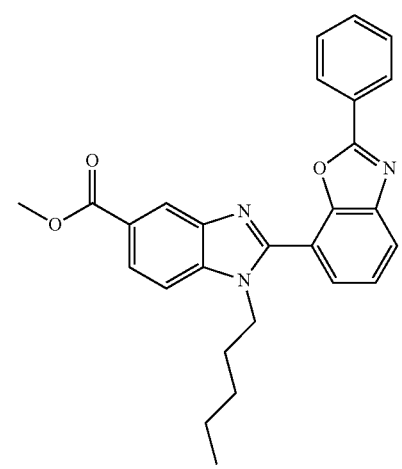
Compound 224
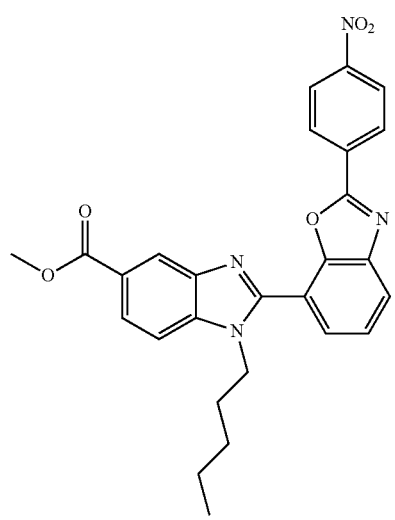
Compound 225
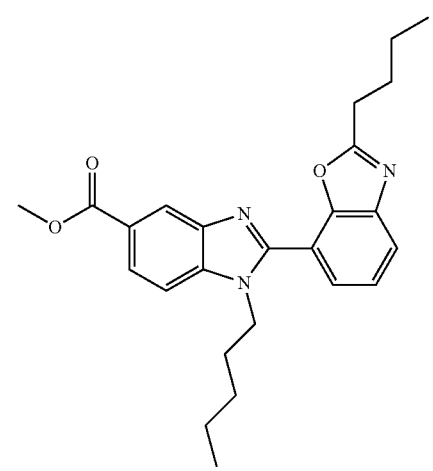

-continued
Compound 226
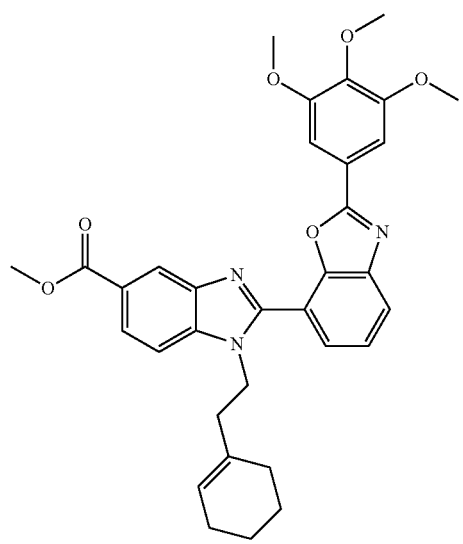
Compound 227
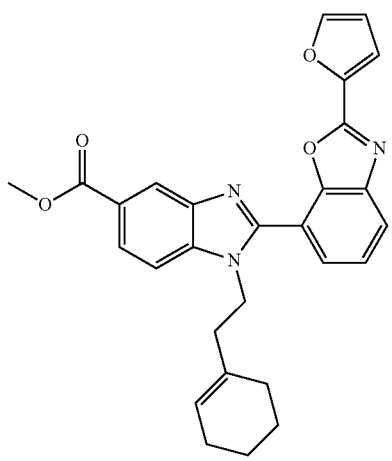
Compound 228
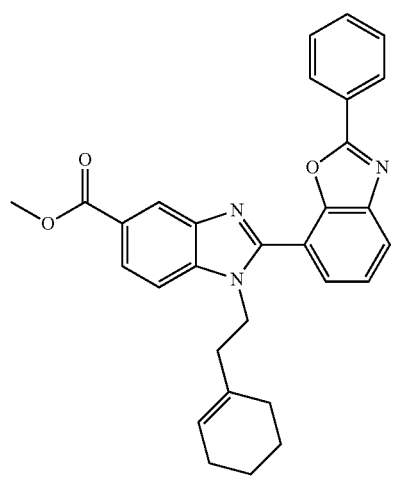
Compound 229
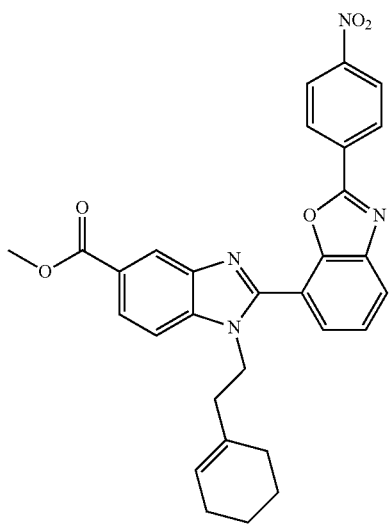
Compound 230
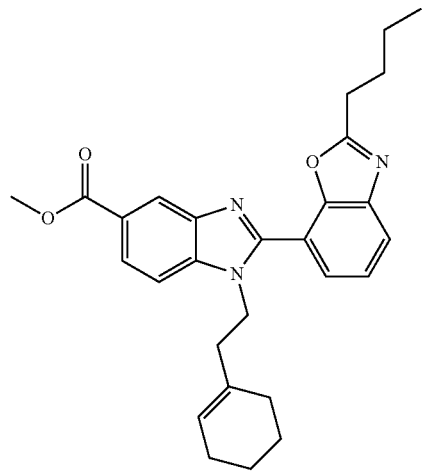
Compound 231
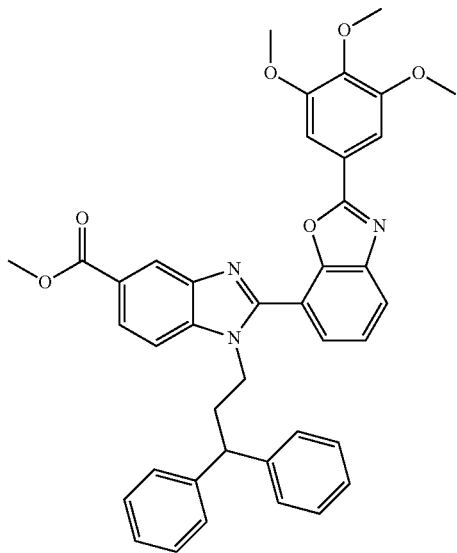

-continued
Compound 232
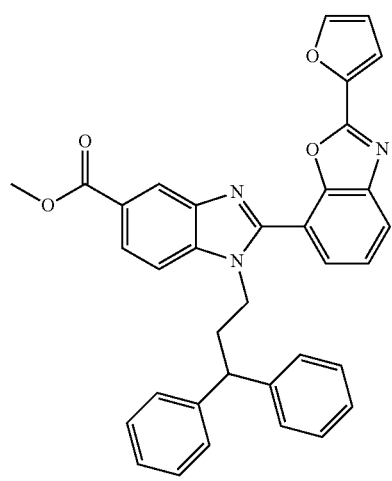
Compound 233
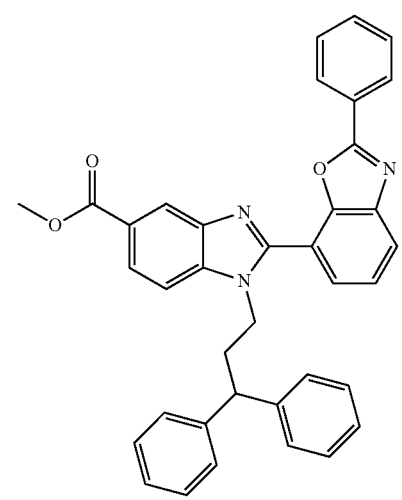
Compound 234
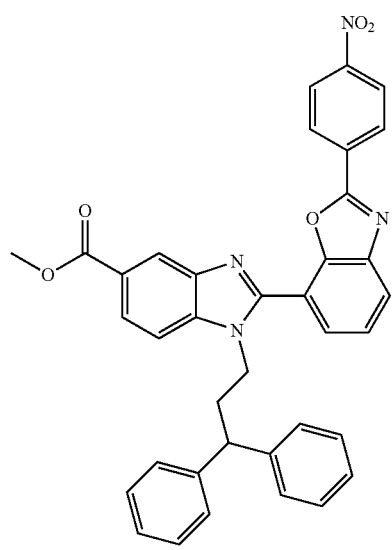
Compound 235
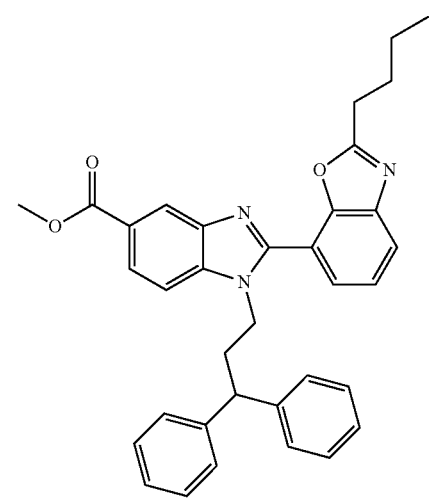
Compound 236
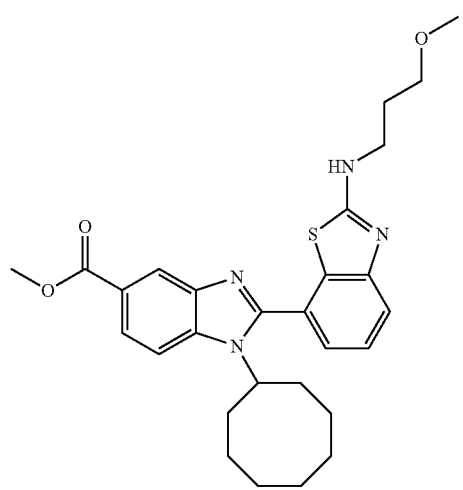
Compound 237
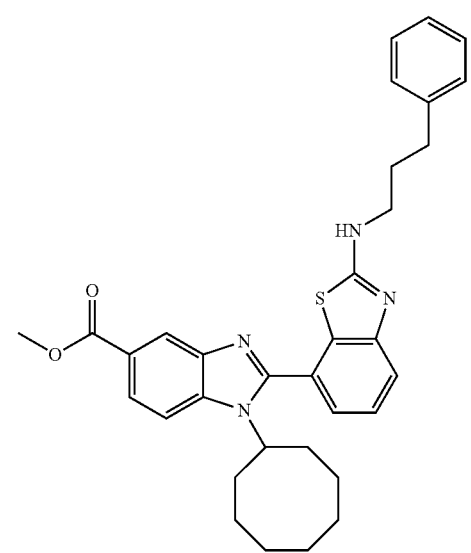

-continued
Compound 238
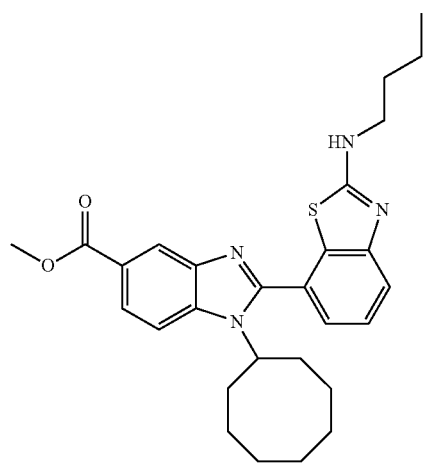
Compound 239
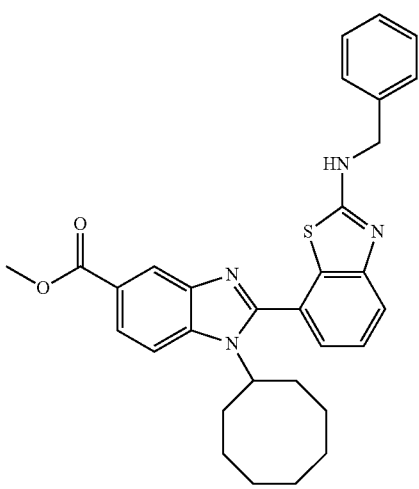
Compound 240
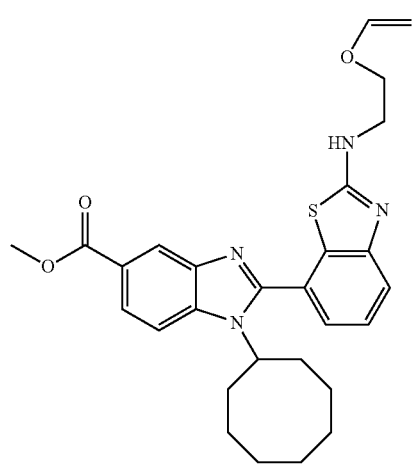
Compound 241
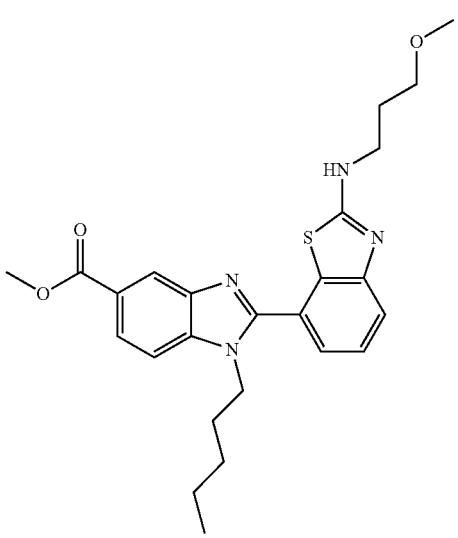
Compound 242
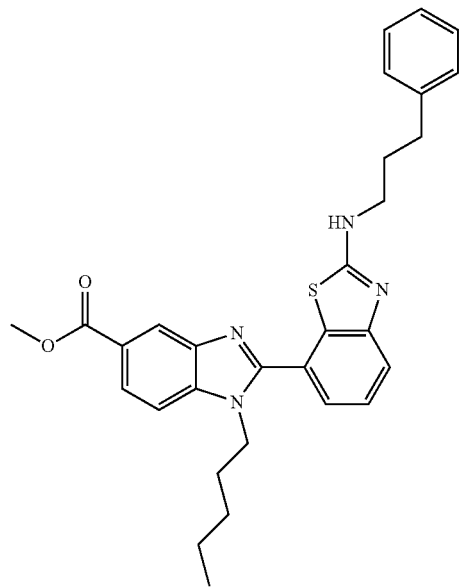
Compound 243
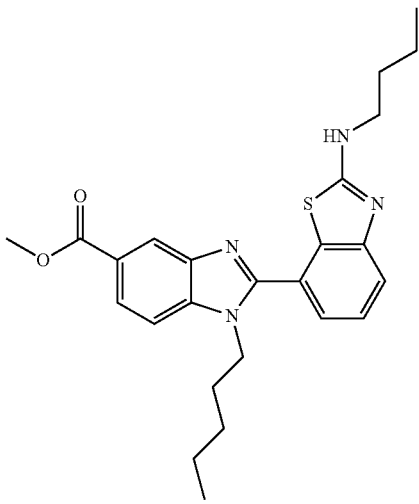

Compound 244
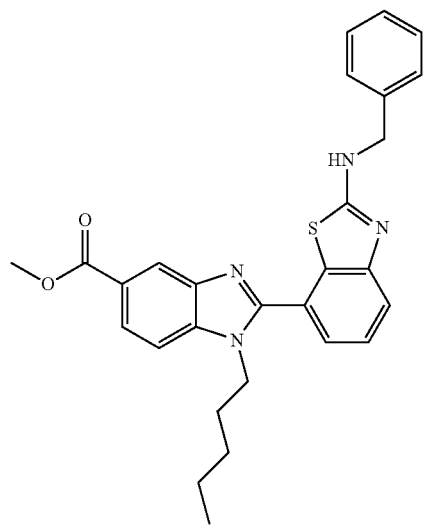
Compound 245
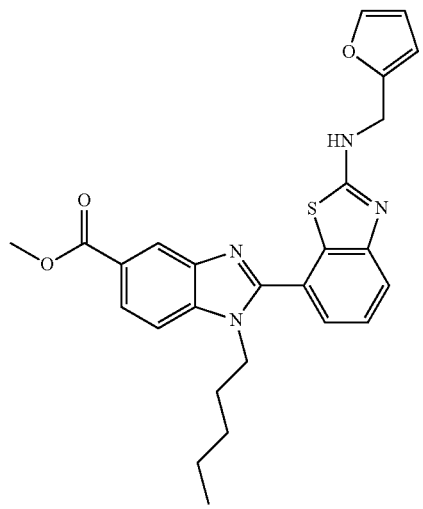
Compound 246
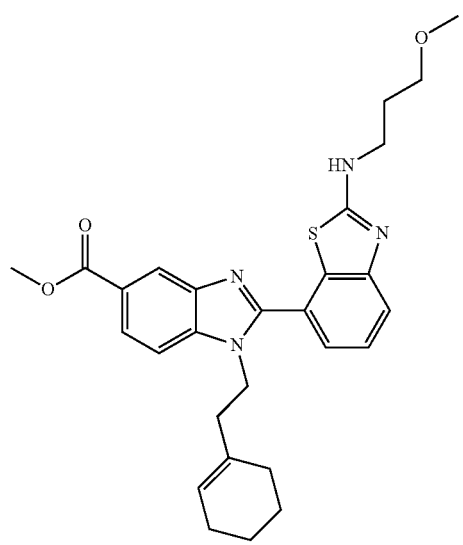
Compound 247
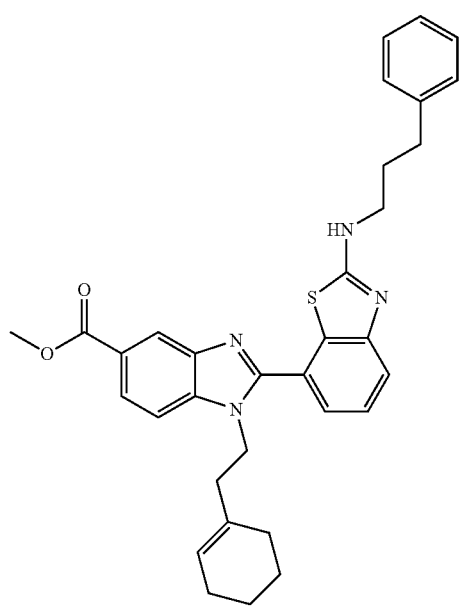
Compound 248
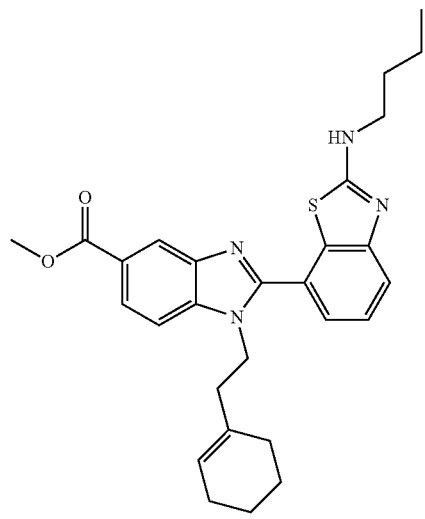
Compound 249
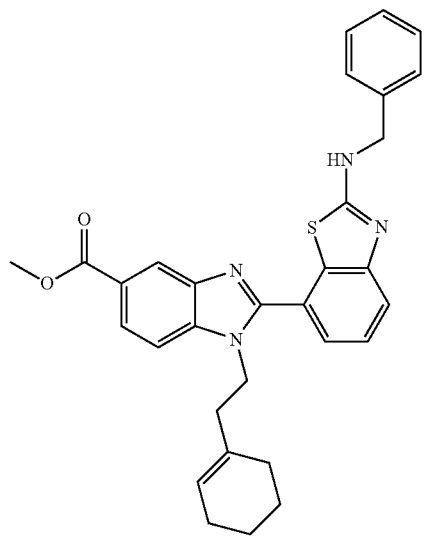

-continued
Compound 250
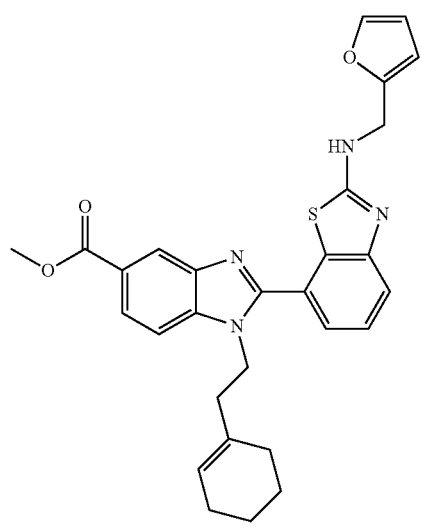
Compound 251
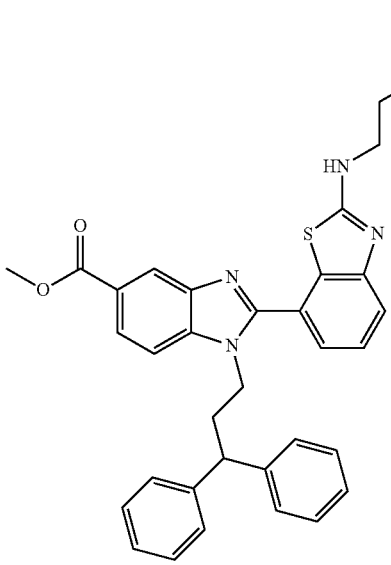
Compound 252
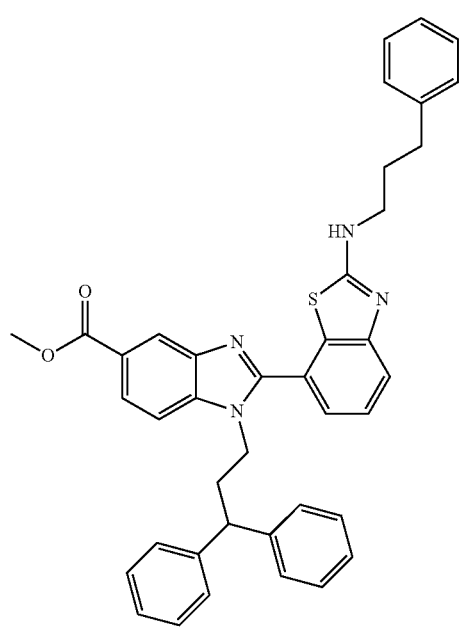
Compound 253
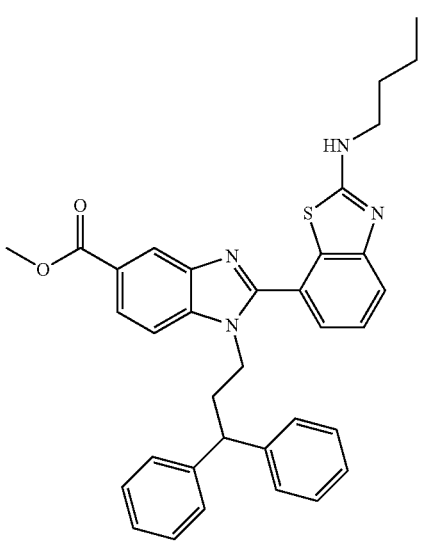

-continued
Compound 254
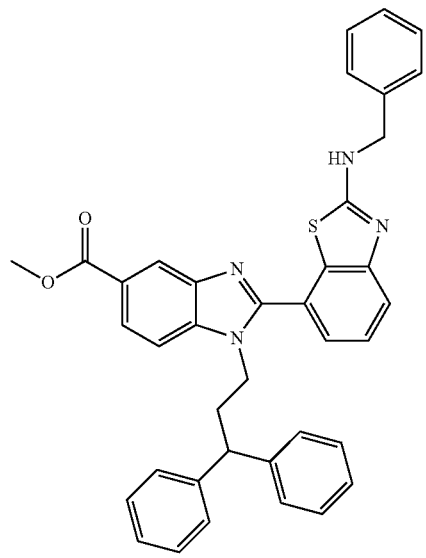
Compound 255
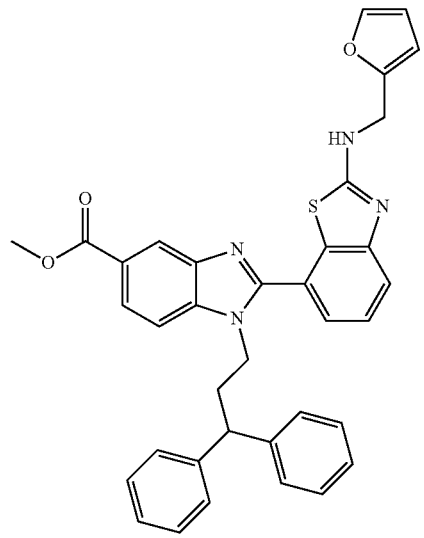
Compound 256
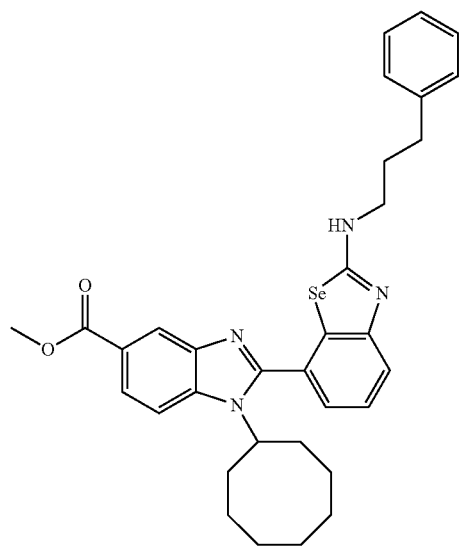
Compound 257
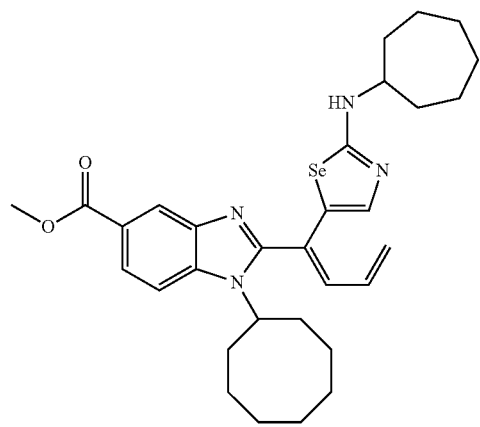

-continued
Compound 258
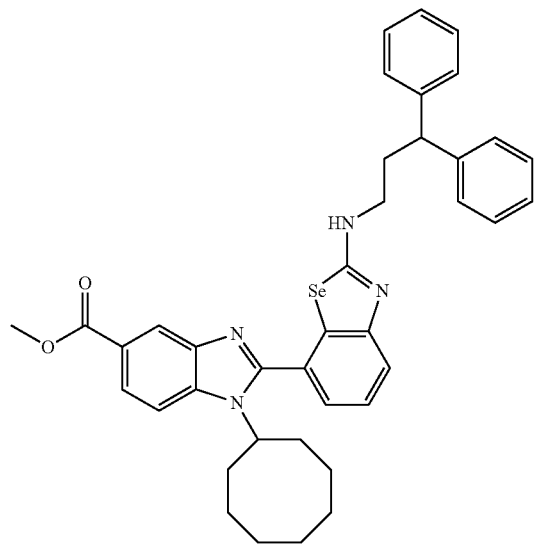
Compound 259
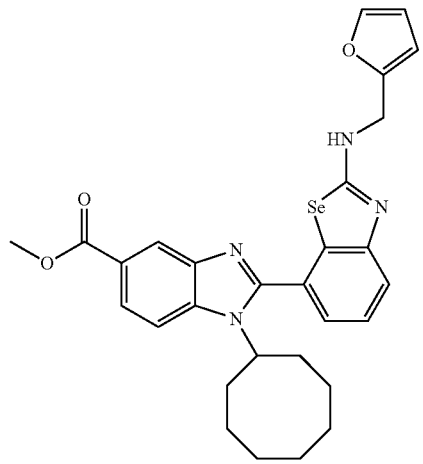
Compound 260
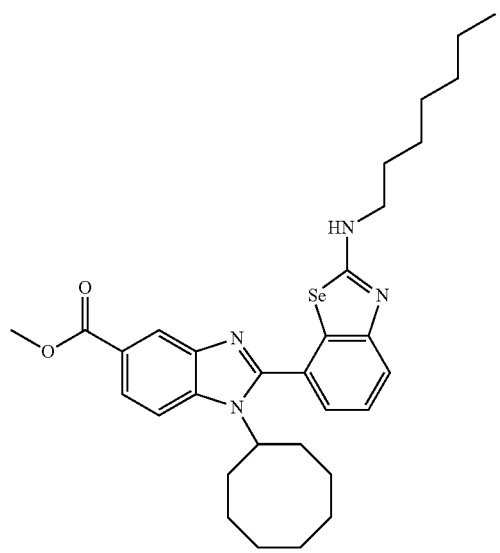
Compound 261
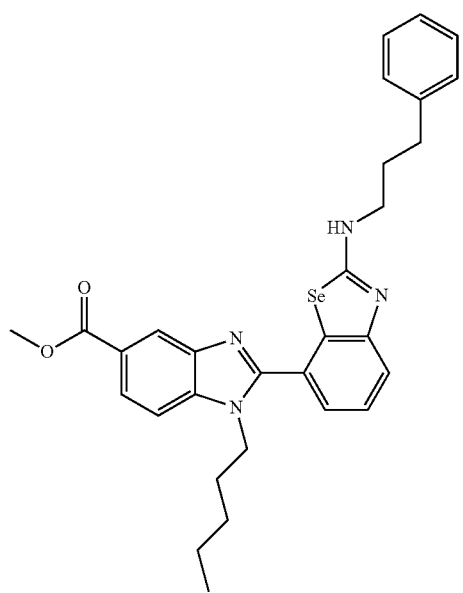

-continued
Compound 262
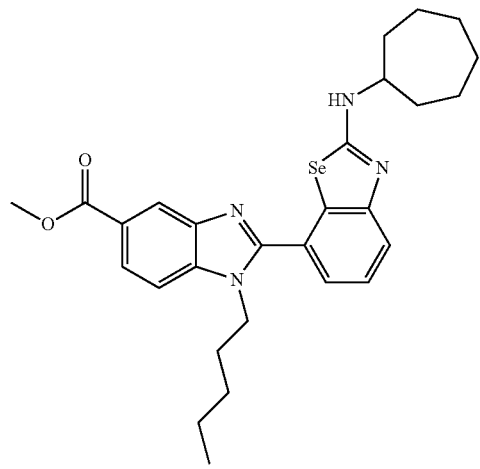
Compound 263
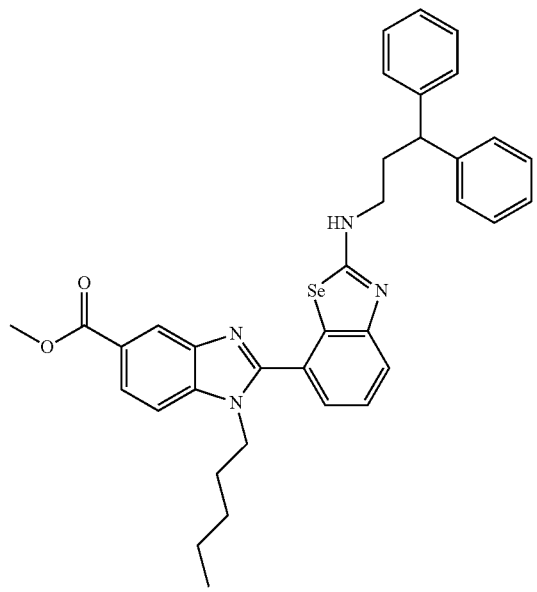
Compound 264
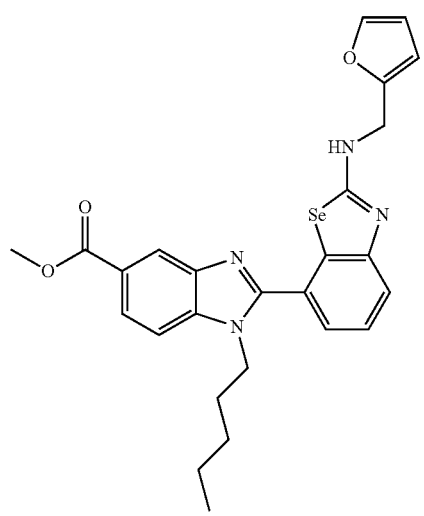
Compound 265
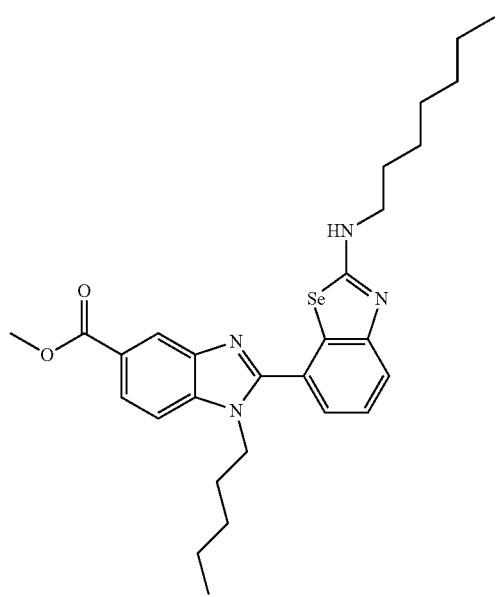

-continued
Compound 266
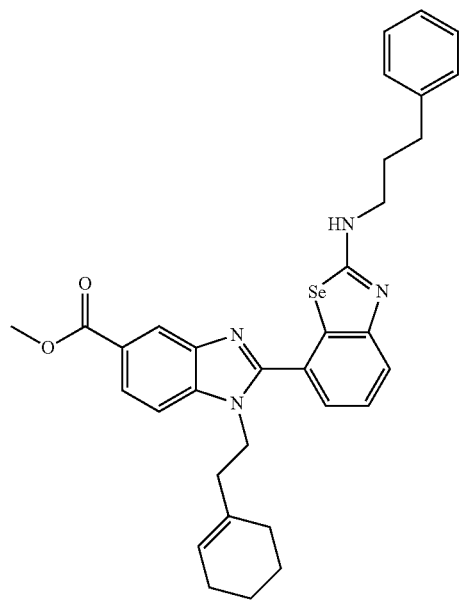
Compound 267
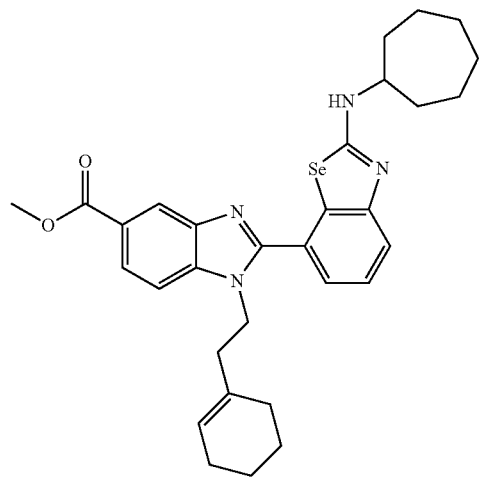
Compound 268
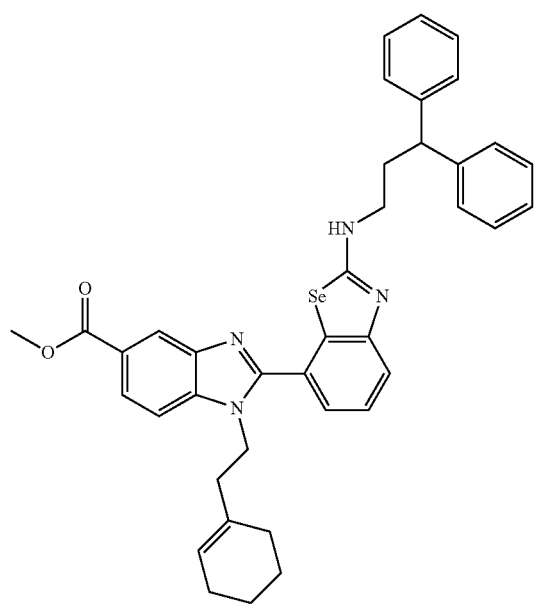
Compound 269
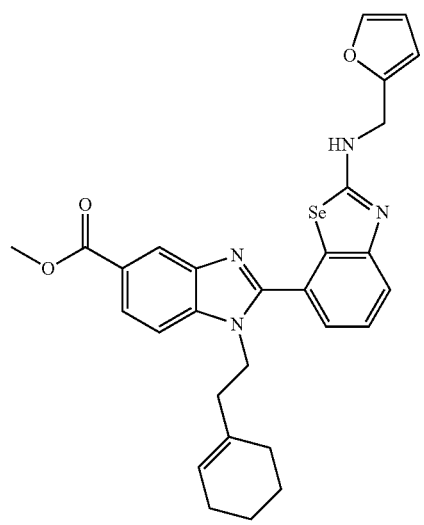

-continued
Compound 270
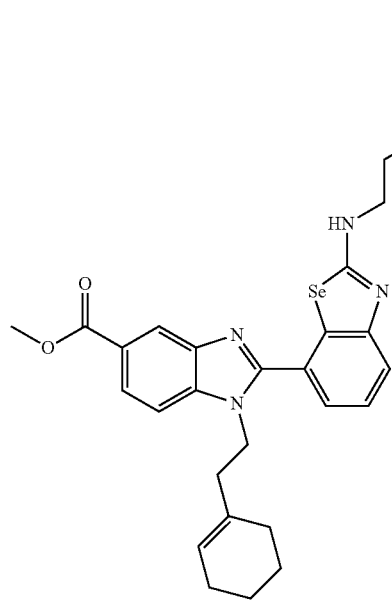
Compound 271
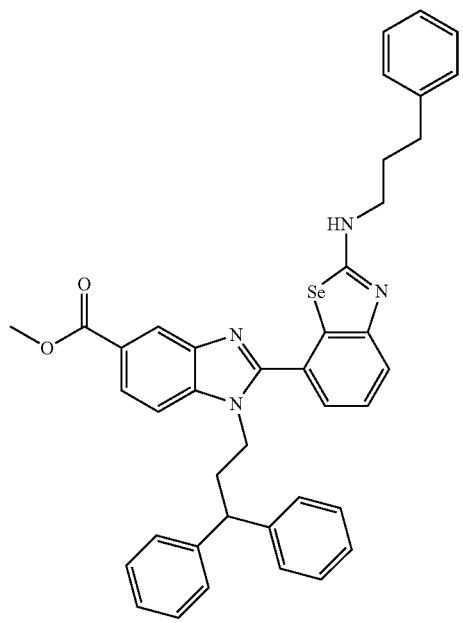
Compound 272
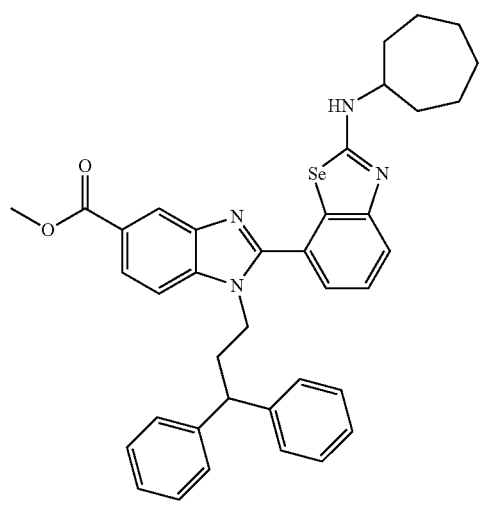
Compound 273
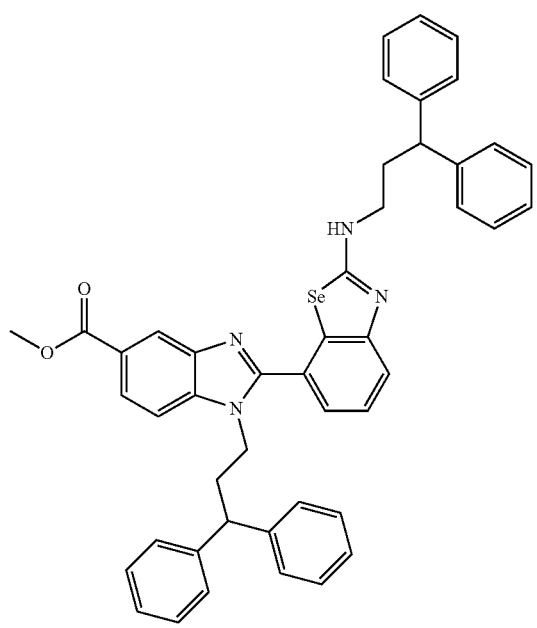

Compound 274
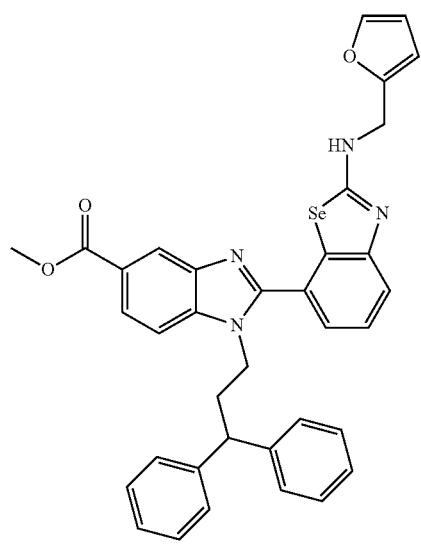
Compound 275
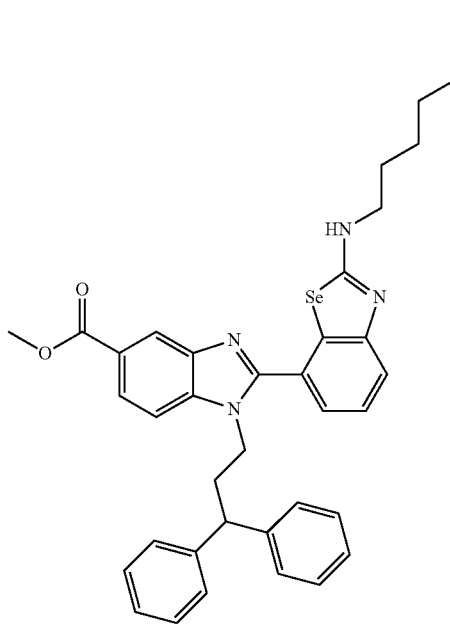
Compound 276
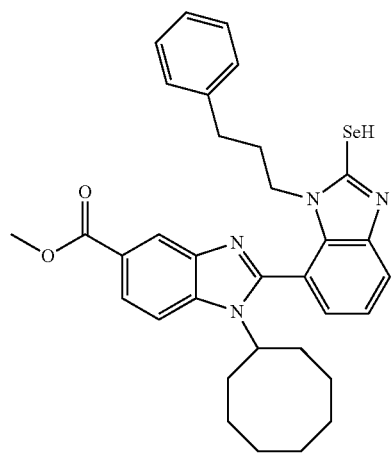
Compound 277
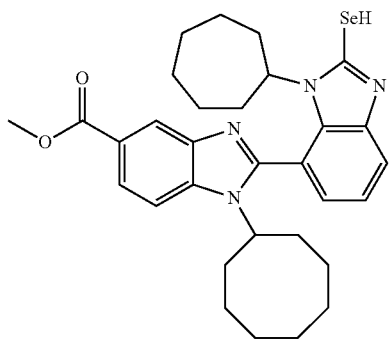
Compound 278
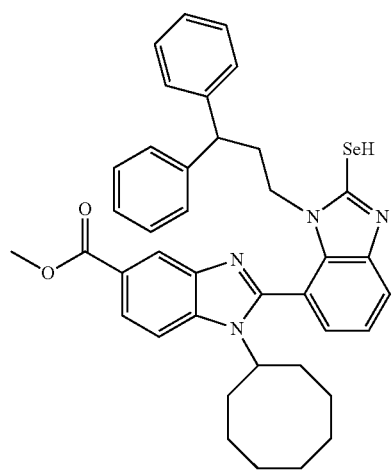
Compound 279
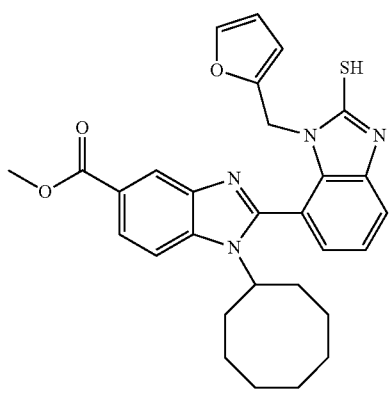

-continued
Compound 280
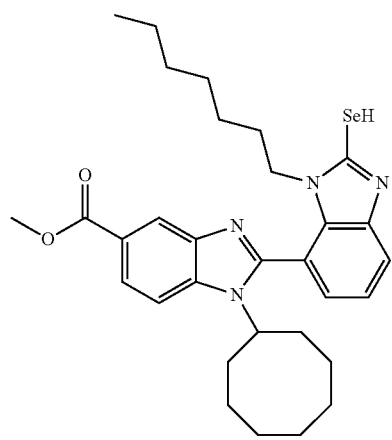
Compound 281
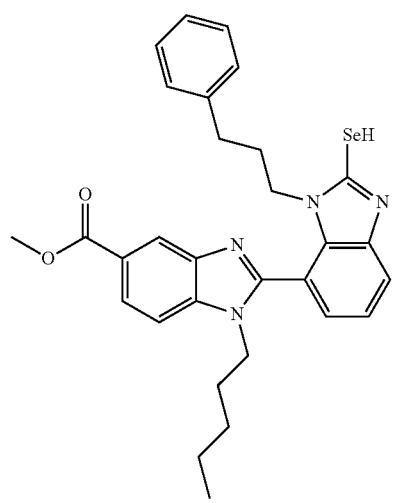
Compound 282
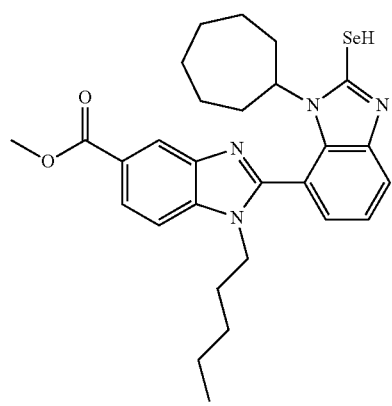
Compound 283
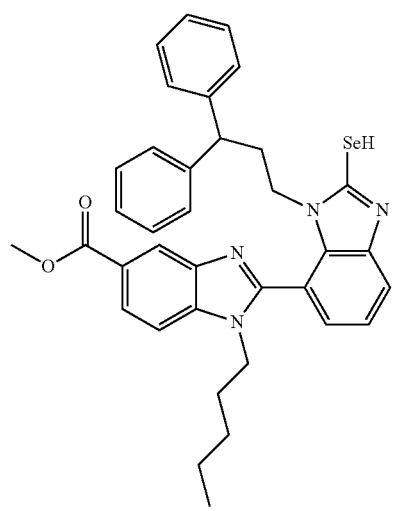
Compound 284
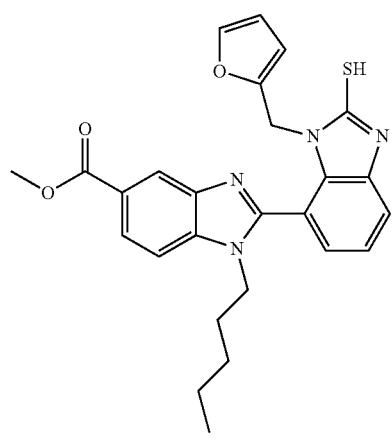
Compound 285
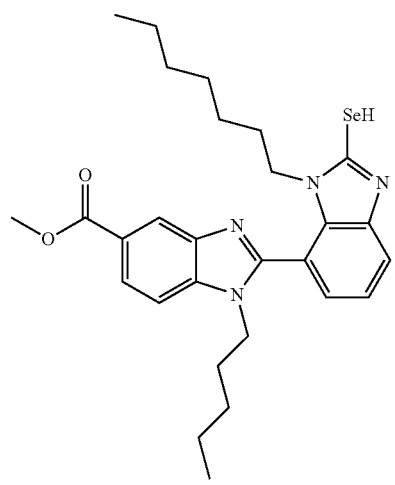

Compound 286
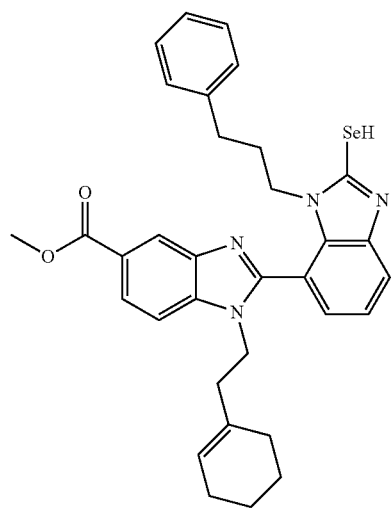
Compound 287
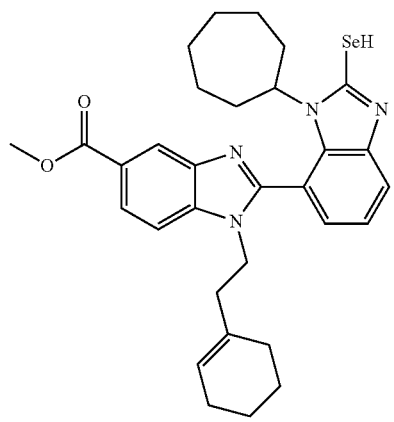
Compound 288
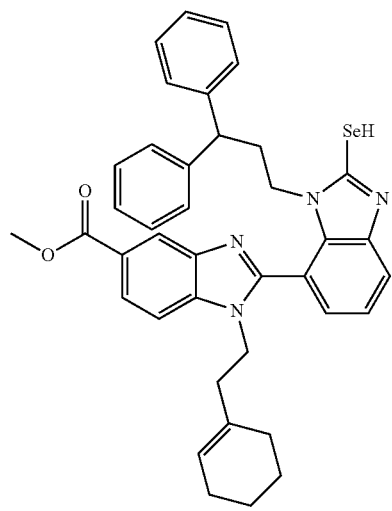
Compound 289
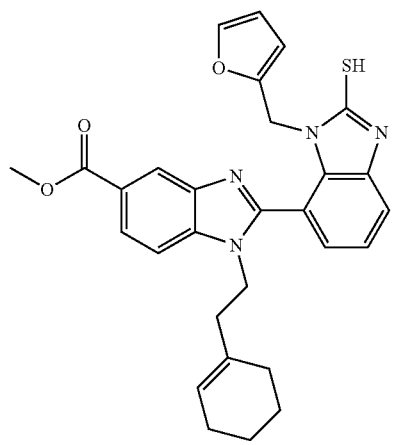
Compound 290
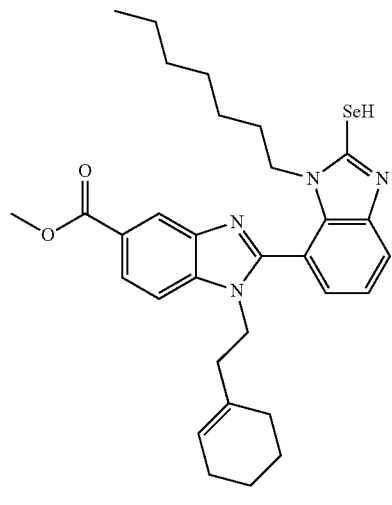
Compound 291
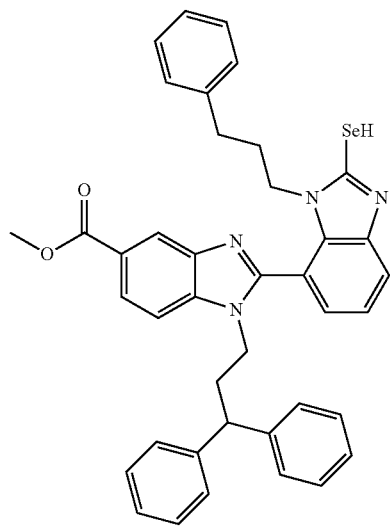

-continued
Compound 292
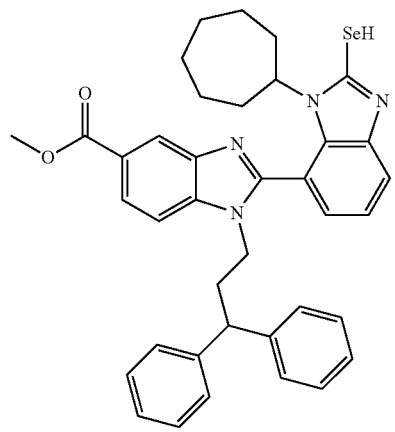
Compound 293
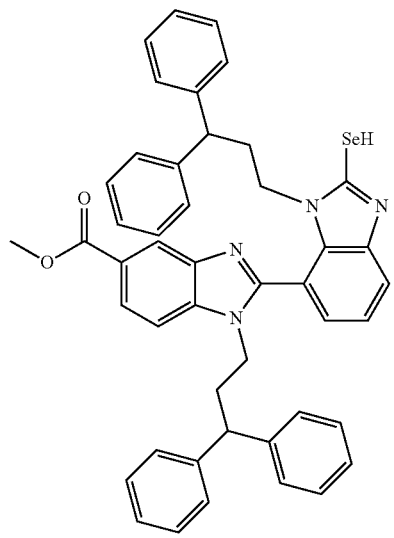
Compound 294
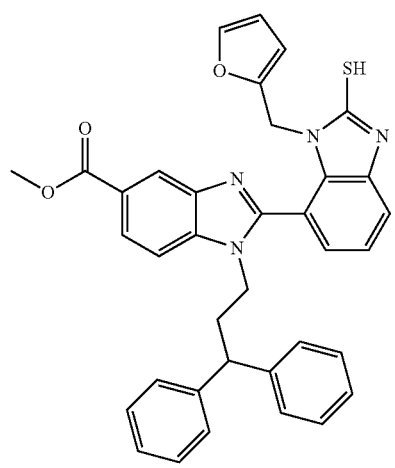
Compound 295
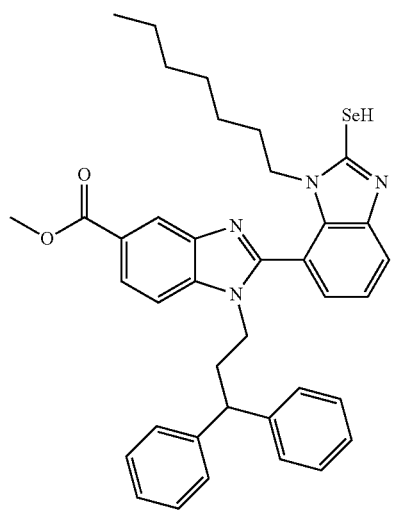
Compound 296
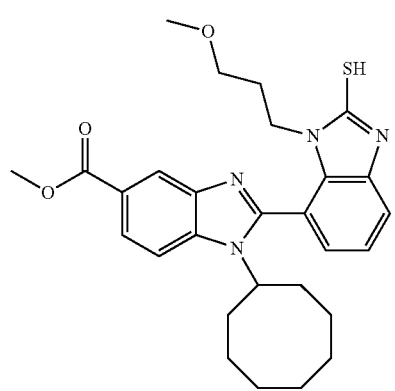
Compound 297
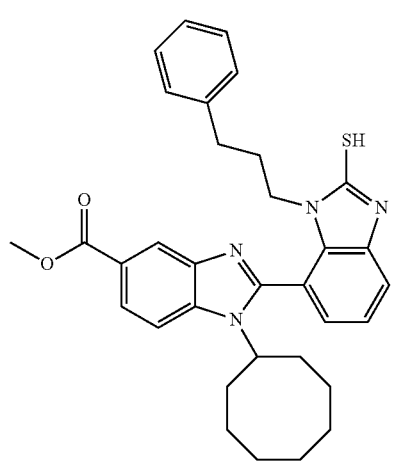

-continued
Compound 298
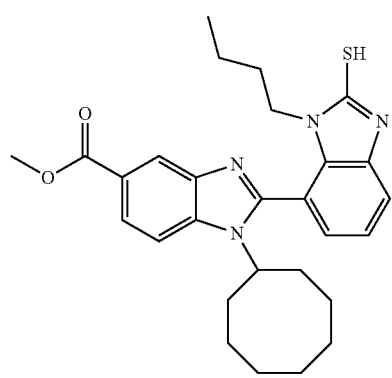
Compound 299
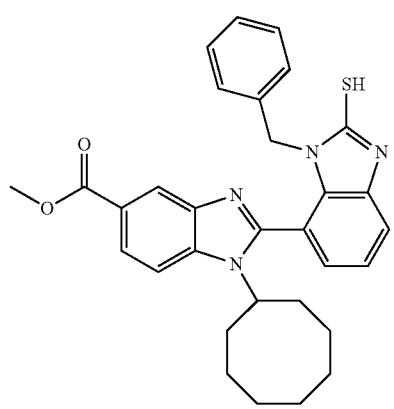
Compound 300
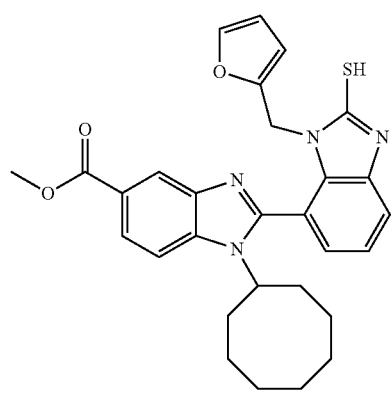
Compound 301
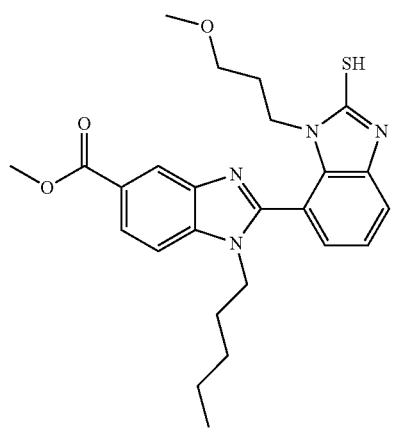
Compound 302
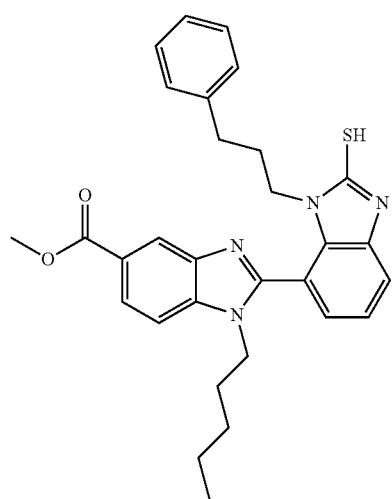
Compound 303
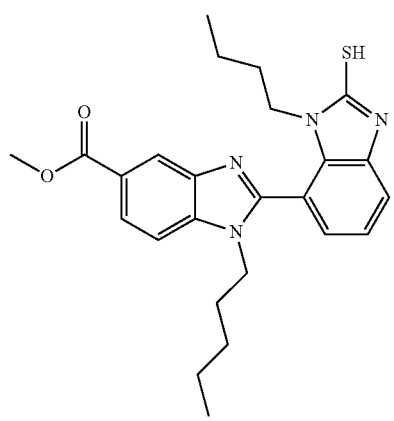

-continued
Compound 304
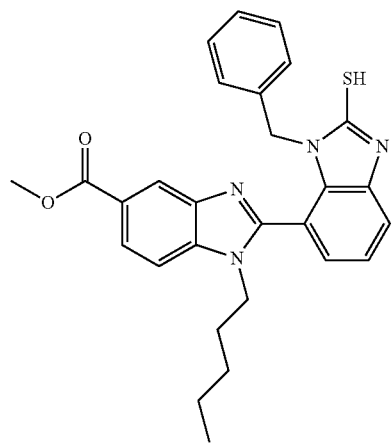
Compound 305
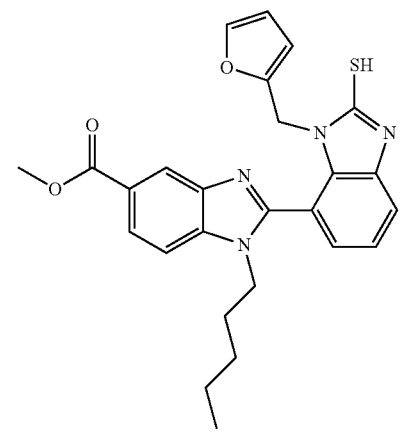
Compound 306
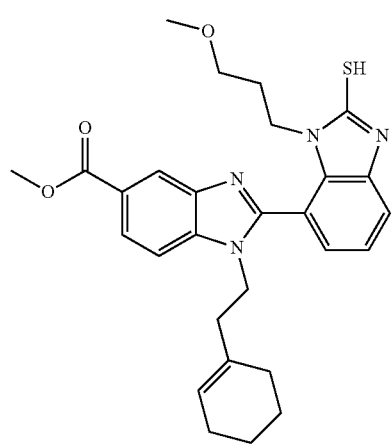
Compound 307
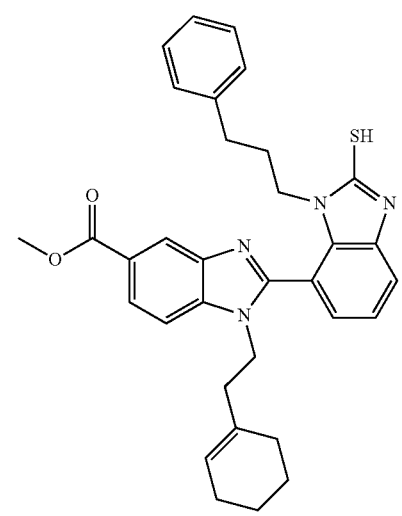
Compound 308
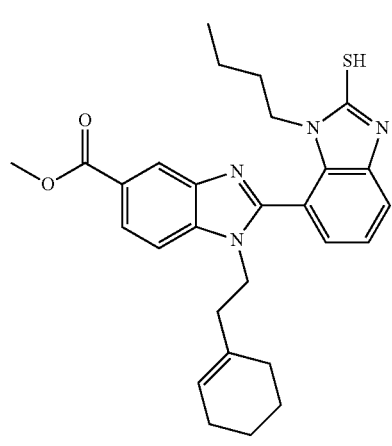
Compound 309
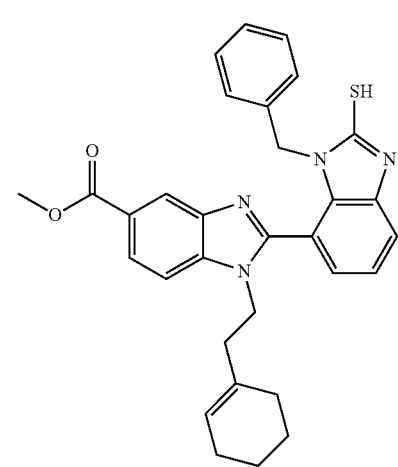

Compound 310

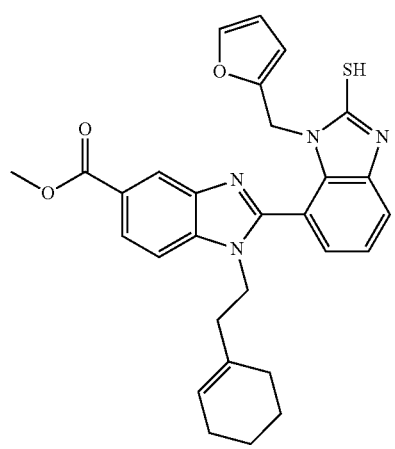

Compound 311

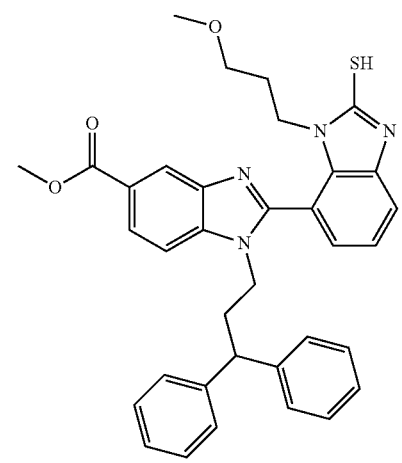

Compound 312

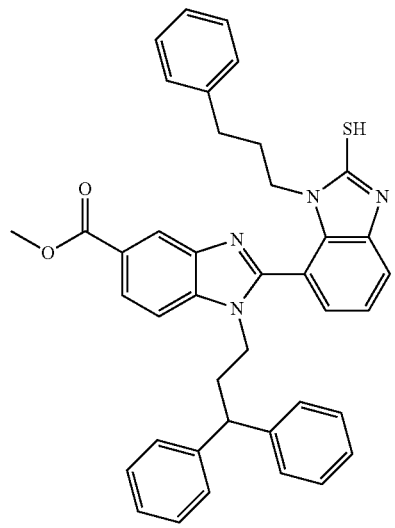

Compound 313

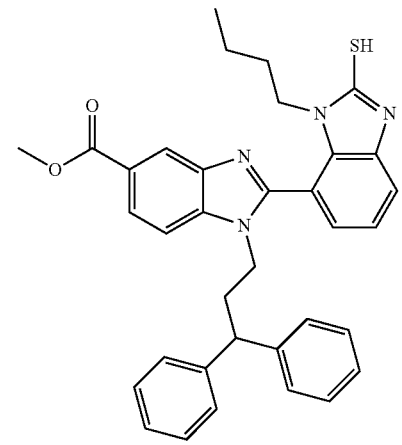

Compound 314

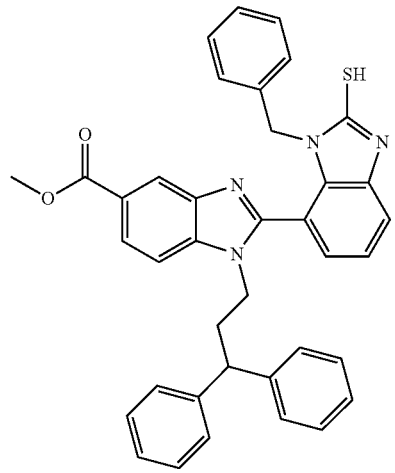

Compound 315

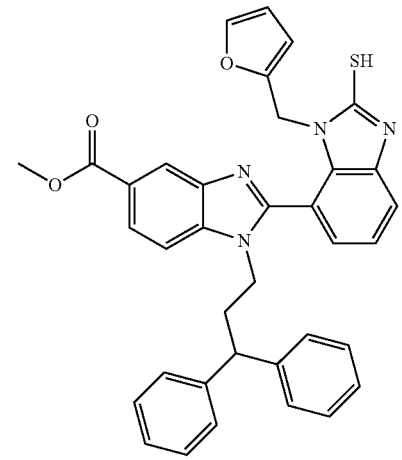

The bicyclic heteroaryl compounds described above can be prepared by methods well known in the art. Examples 1-186 below provide detailed descriptions of how Compounds 1-186 were actually prepared.

Scheme I shown below illustrates a typical synthetic route for synthesizing certain exemplary bicyclic heteroaryl compounds. $R_2$ and $R_5$ in this scheme can be those described in the Summary section above.

Scheme I

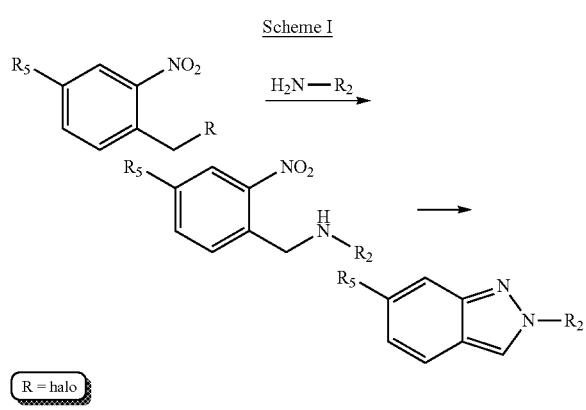

R = halo

Specifically, as shown in Scheme I above, a substituted benzene containing a nitro group and a halo group can first react with a primary amine compound to form a secondary amine compound. This compound can then undergo a ring closure reaction between the nitro group and the secondary amino group to form a bicyclic heteroaryl compound of this invention.

Scheme II below illustrates a synthetic route for synthesizing bicyclic heteroaryl compounds in which $X_1$ and $X_3$ is N, $X_2$ is C, and $R_2$ is

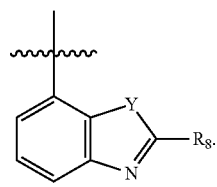

$R_1$ and $R_4$ though $R_8$ in this scheme can be those described in the Summary section above. $R_9$ can be H, alkyl, alkenyl, alkynyl, cycloalkyl, cycloalkenyl, heterocycloalkyl, heterocycloalkenyl, aryl, or heteroaryl.

Scheme II

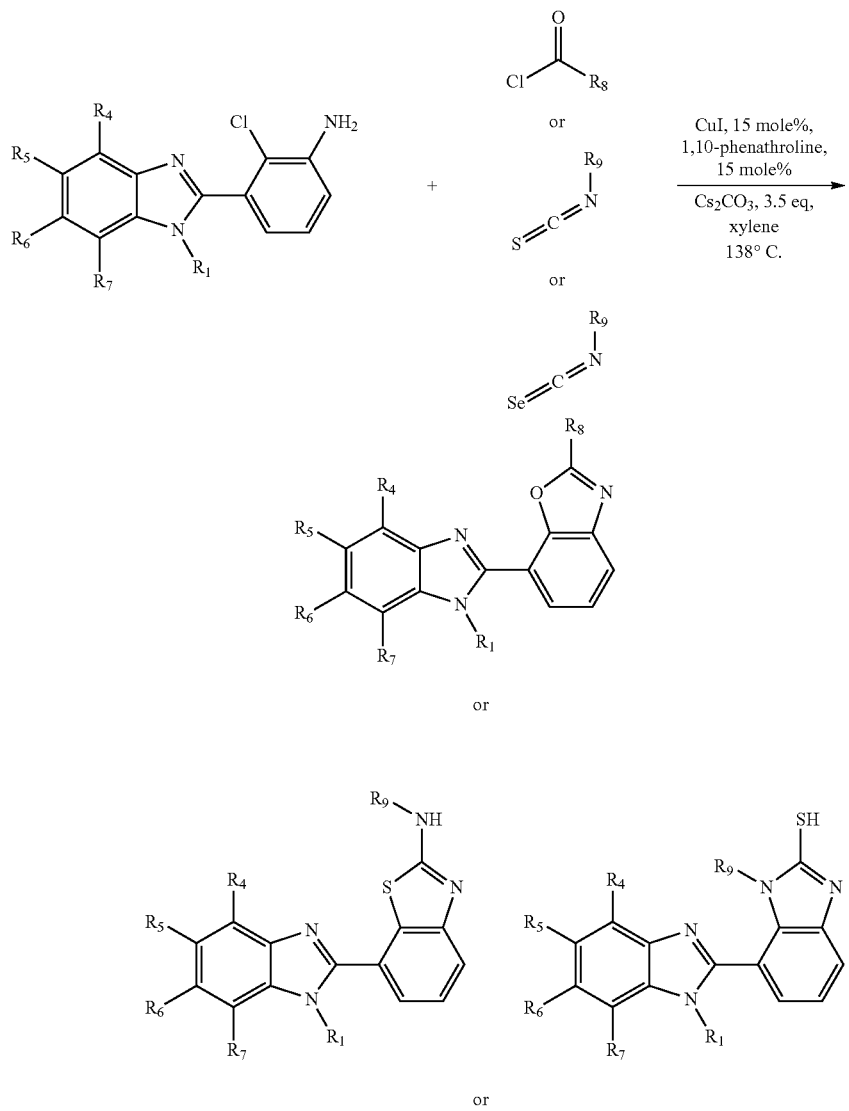

-continued

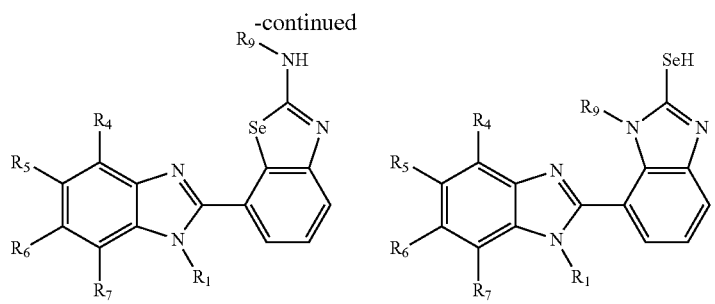

A bicyclic heteroaryl compound synthesized above can be purified by a suitable method such as column chromatography, high-pressure liquid chromatography, or recrystallization.

Other bicyclic heteroaryl compounds can be prepared using other suitable starting materials through the above synthetic routes and others known in the art such as those described in Chen et al., *J. Comb. Chem.*, 2009 (11), 1038-1046. The methods described above may also additionally include steps, either before or after the steps described specifically herein, to add or remove suitable protecting groups in order to ultimately allow synthesis of the bicyclic heteroaryl compounds. In addition, various synthetic steps may be performed in an alternate sequence or order to give the desired compounds. Synthetic chemistry transformations and protecting group methodologies (protection and deprotection) useful in synthesizing applicable bicyclic heteroaryl compounds are known in the art and include, for example, those described in R. Larock, *Comprehensive Organic Transformations*, VCH Publishers (1989); T. W. Greene and P. G. M. Wuts, *Protective Groups in Organic Synthesis*, $2^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The bicyclic heteroaryl compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition containing at least one bicyclic heteroaryl compound described above and a pharmaceutical acceptable carrier. Further, this invention covers a method of administering an effective amount of one or more of the bicyclic heteroaryl compounds to a patient having cancer. "An effective amount" refers to the amount of an active bicyclic heteroaryl compound that is required to confer a therapeutic effect on the treated subject. Effective doses will vary, as recognized by those skilled in the art, depending on the types of diseases treated, route of administration, excipient usage, and the possibility of co-usage with other therapeutic treatment. For example, a daily dose of 5 mg/kg of compound 1 can be used reduce metastasis and a daily dose of 50 mg/kg can be used to inhibit tumor growth.

To practice the method of the present invention, a composition having one or more bicyclic heteroaryl compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active bicyclic heteroaryl compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active bicyclic heteroaryl compound. Examples of other carriers include colloidal silicon oxide, magnesium stearate, cellulose, sodium lauryl sulfate, and D&C Yellow #10.

The bicyclic heteroaryl compounds described above can be preliminarily screened for their efficacy in treating above-described diseases by in vitro and in vivo assays (see Examples 186 and 187 below) and then confirmed by clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

EXAMPLE 1

Preparation of Compound 1: methyl 2-(3,3-diphenylpropyl)-2H-indazole-6-carboxylate

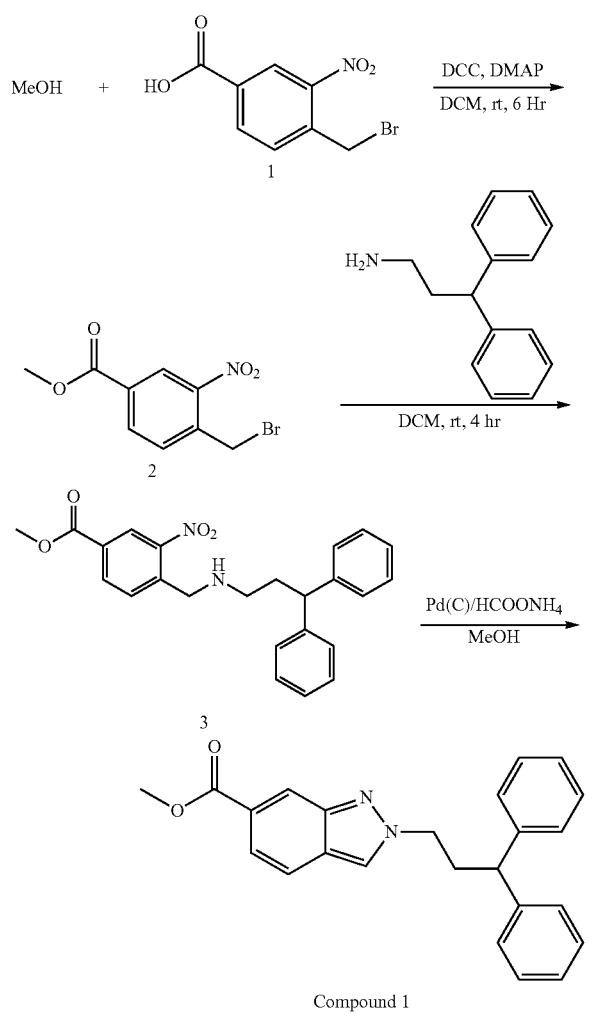

A solution of dicyclohexylcarbodiimide (DCC, 0.95 g, 4.61 mmol, 1.2 equiv) in 10 mL of dichloromethane (DCM) was added dropwise to a stirred mixture of 4-bromomethyl-3-nitro-benzoic acid 1 (1.0 g, 3.84 mmol, 1.0 equiv) and 4-dimethylaminomethyl pyridine (DMAP) (0.020 g, 0.19 mmol, 0.05 equiv) in 10 mL of dichloromethane-methanol (10%) at room temperature. The mixture was stirred for 6 hours to obtain 4-bromomethyl-3-nitro-benzoic acid methyl ester 2. Dicyclohexyl urea (DCU) thus obtained was removed by filtration and the solvent in the filtered solution was removed under vacuum. The residue was purified by column chromatography using hexane-ethyl acetate (15%) as an eluant to give ester 2 as a light yellow oil.

To a solution of ester 2 (0.91 g, 3.32 mmol, 1.0 equiv) in 10 mL of dichloromethane was added dropwise 3,3-diphenyl-propylamine (1.40 g, 6.64 mmol, 2.0 equiv). The mixture was stirred at room temperature for 8 hours. After the amine salt thus obtained was removed by filtration, the solvent in the filtered solution was removed under vacuum to give crude 4-[(3,3-diphenyl-propylamino)-methyl]-3-nitro-benzoic acid methyl ester 3. The crude product was purified by column chromatography using hexane-ethyl acetate (25%) to give ester 3 as a light brown oil.

4-[(3,3-diphenyl-propylamino)-methyl]-3-nitro-benzoic acid methyl ester 3 (0.81 g, 3.21 mmol) was dissolved in 10 ml of methanol and treated with ammonium formate (1.26 g, 20.02 mmol, 10 equiv) and palladium on carbon (162 mg, 20%). The mixture was stirred for 1 day at room temperature. After the mixture was then filtered through a small plug of Celite and washed with dichloromethane, the solvent was removed under vacuum to give a crude product. The crude product was purified by column chromatography using hexane-ethyl acetate (25%) to give compound 1, 2-(3,3-diphenyl-propyl)-2H-indazole-6-carboxylic acid methyl ester, as a white solid.

$^1$H NMR (300 MHz, CDCl$_3$) δ 8.53 (s, 1H), 7.82 (s, 1H), 7.75-7.72 (dd, J=8.7, 1.2 Hz, 1H), 7.69~7.66 (dd, J=8.7, 0.5 Hz, 1H), 7.35~7.20 (m, 10H), 4.41 (t, J=6.9 Hz, 2H), 3.97 (s, 3H), 3.88 (t, J=7.9 Hz, 1H), 2.87~2.80 (q, J=7.2 Hz, 2H).

$^{13}$C NMR (75 MHz, CDCl3) δ 167.56, 148.13, 143.25, 128.68, 127.71, 126.61, 123.65, 123.27, 121.28, 121.18, 120.07, 52.36, 52.13, 48.12, 35.94; IR (cm-1, neat): 3236, 2948, 1713, 1601, 1443, 1269.

MS (EI): m/z 370 (M$^+$). Exact mass calculated for C$_{24}$H$_{22}$N$_2$O$_2$: m/z 370.1681 Found 370.1681.

EXAMPLES 2-55

Preparation of Compounds 2-55

Compounds 2-55 were prepared in a manner similar to that described in Example 1.

EXAMPLES 56-186

Preparation of Compounds 56-186

Compounds 56-186 were prepared in a manner similar to that described in Example or that described in Chen et al., *J. Comb. Chem.*, 2009 (11), 1038-1046.

EXAMPLE 187

KIRA-ELISA Assay

This assay was performed in two microtiter plates. The first plate was used to culture an adherent cell line expressing the VEGF receptor 3 and to stimulate the receptor with a test compound. The second plate was used to capture the solubilized membrane receptor, which was then probed for phosphotyrosine content with phosphotyrosine-specific antibody.

Specifically, H928 cells (2×10$^5$) in 100 μl medium were added to each well in a flat-bottom 24-well culture plate and cultured overnight at 37° C. in 5% CO$_2$. After the supernatants were removed, the cells were serum-starved for 24 hours. A medium containing a test compound was added into each well and the cell culture was incubated for 30 minutes before it was stimulated by recombinant VEGF-C for 15 minutes. After the supernatants were removed, 100 µl of a lysis buffer were added into each well to lyse the cells and solubilize the VEGFR3. The lysis buffer included 150 mM NaCl containing 50 mM Hepes (Genentech media prep), 0.5% Triton-X 100 (Genentech media prep), 0.01% thimerosol, 30 kIU/ml aprotinin (ICN Biochemicals, Aurora, Ohio), 1 mM 4-(2-aminoethyl) benzenesulfonyl fluoride hydrochloride (AEBSF; ICN Biochemicals), and 2 mM sodium orthovanadate. The plate was then put on a plate shaker (Bellco Instruments Vineland, N.J.) and the substance in each well of the plate underwent mixing for 60 minutes at room temperature. While the cells were being solubilized, an ELISA microtiter plate (Nunc Maxisorp, Inter Med, Denmark) coated overnight at 4° C. with the affinity-purified polyclonal anti-VEGFR 3 (2.5 µg/ml in phosphate buffered saline (PBS), 100 µl/well) were decanted, tamped on a paper towel, and blocked with 150 µl/well block buffer (PBS containing 0.5% BSA and 0.01% thimerosol) for 60 minutes at room temperature with gentle agitation. The anti-VEGFR 3-coated plate was subsequently washed twice with a wash buffer (PBS containing 0.05% Tween 20 and 0.01% thimerosol). The lysate containing solubilized VEGFR 3 from the cell-culture microtiter well were transferred (85 µl/well) to the anti-VEGFR 3-coated ELISA plate and incubated for 2 hours at room temperature with gentle agitation. The unbound receptors were removed by washing with a wash buffer. 100 µl of biotinylated 4G10 (antiphosphotyrosine) diluted to 0.2 µg/ml in dilution buffer (PBS containing 0.5% BSA, 0.05% Tween 20, 5 mM EDTA, and 0.01% thimerosol) were added into each well. After incubation for 2 hours at room temperature, the plate were washed and 100 µl HRP-conjugated streptavidin (Zymed Laboratories, S. San Francisco, Calif.) diluted 1:2000 in dilution buffer will be further added. After the free avidin conjugate were washed away, 100 µl freshly prepared substrate solution (tetramethyl benzidine, TMB) was added to each well. The reaction was allowed to proceed for 10 minutes and the color development was stopped by the addition of 100 µl/well 1.0 M $H_3PO_4$. The absorbance at 450 nm and the absorbance at a reference wavelength of 650 nm ($A_{450/650}$) were measured using an ELISA reader.

The inhibition efficacy of each test compound is expressed as an inhibition percentage calculated according to the following formula: 1−[(C−A)/(B−A)]. In this formula, A is the basal amount of phosphotyrosine detected in a blank control, B is the amount of phosphotyrosine detected with VEGF-C only, and C is the amount of phosphotyrosine detected with a test compound and VEGF-C.

Among the 186 compounds already synthesized, 118 compounds (i.e., compounds 1-22, 24-30, 32, 34-39, 41-50, 52-122, and 186) were tested. Unexpectedly, Compound 2, at concentration of 1 µM, showed an inhibition percentage of about 65%; Compounds 26, 57-58, 60-61, 66-68, 70, 72-77, 79-80, 82, 86, 88, 90, 93-96, 98-99, 102-103, 105-108, 110-112, 115, 120, and 186 each showed substantially the same inhibition percentage as Compound 2; and Compounds 11, 56, 59, 62, 64-65, 81, 83-85, 87, 89, 91, 100, 113-114, 117, 119, and 121 each showed an even higher inhibition percentage than Compound 2.

EXAMPLE 188

In vivo Assay on Tumor Growth Inhibition

Compounds were tested for their efficacy in inhibiting tumor growth on murine tumor xenografts.

Murine 4T1 breast cancer cells (purchased from the American Type Culture Collection) were cultured to sub confluence in RPMI medium supplemented with 10% fetal bovine serum (GIBCO Invitrogen Corp.) at 37° C., 90% humidity and 5% $CO_2$. The $4T1^{LUC+}$ cells were established by the stable transfection of the firefly luciferase gene (pGL3-control, Promega Corporation) to 4T1 cells using LipofectAMINE PLUS Reagent (Life Technologies, Inc., Grand Island, N.Y.) for quantitative assessment of tumor burden in visceral organs. pcDNA3 vector (Invitrogen Co., Carlsbad, Calif.) was cotransfected for the selection by G418 (Sigma). The resulting $4T1^{LUC+}$ colonies were isolated and cultured independently and the best expressing lines were identified based on the level of bioluminescent activity in the presence of luciferin in living cells. Highly bioluminescent clone was selected for further studies.

Next, $4T1^{LUC+}$ cells were orthotopically implanted into the right inguinal mammary fat pads of 6 to 8-week old female BALB/c mice (1×10$^5$ cells in 100 µL PBS/mouse). After 14 days of tumor cell implantation, a single dose of 50 mg/kg body weight of a test compound or vehicle was administered intraperitoneally once daily.

The length (i.e., the biggest diameter) and width (i.e., the smallest diameter) of the tumor was measured every 3.5 days by using a Vernier caliper. The tumor volume was then calculated as follows: volume=A×B$^2$×0.52, where A is the length of the tumor and B is the width of the tumor.

Compounds 2, 56, and 91 (i.e., the acid form of Compound 56, denoted as 56-A in FIG. 1) were tested. Sorafenib (Nexavar®) and sunitinib (Sutent®), two commercial anti-cancer drugs, were used as reference compounds. Unexpectedly, Compound 56 (denoted as 56-E) inhibited tumor growth almost as effectively as Sutent and Sorafenib, as shown in FIG. 1. Also unexpectedly, mice treated with Compound 56 showed a higher survival rate than those treated with Sorafenib.

EXAMPLE 189

In vivo Assay on Inhibiting Spontaneous Metastasis

To investigate the effect of test compounds on distant spontaneous metastasis generated by the tumor cells, $4T1^{LUC+}$ cells obtained by the method described in Example 188 were implanted into the right inguinal mammary fat pads of 6-week old BALB/c mice (1×10$^5$ cells in 100 µL PBS/mouse). After 14 days of tumor cell implantation, a single dose of 50 mg/kg body weight of a test compound or vehicle was administered intraperitoneally once daily. Compounds 2, 56, and 91 were used in this assay. Sorafenib (Nexavar®) and sunitinib (Sutent®) were also used as reference compounds.

A total of 36 mice, six for each of the six groups (i.e., 5 groups treated with test compounds and 1 vehicle group), were imaged once weekly for a period of 6 weeks after tumor cell implantation via bioluminescence imaging.

In vivo bioluminescence imaging was conducted on a cryogenically cooled IVIS™ system (Xenogen Corp., Alameda, Calif.) coupled to a data-acquisition PC running Living Image version 3.1 software (Xenogen Corp.). Before imaging, animals were anesthetized in a plastic chamber filled with 2% isofluorane/air mixture and 150 mg/mL of luciferin (potassium salt, Xenogen Corp.) and normal saline was injected (i.p.) into each mouse at a dose of 150 mg/kg body weight. This dose and route of administration has been previously shown to be optimal for studies in rodents when images were acquired between 10 and 20 minutes post-luciferin administration (Contag C H et al. 1997 *Photochem Photobiol.*;

66:523-531). During image acquisition, isofluorane anesthesia was maintained using a nose cone delivery system and animal body temperature was regulated using a digitally thermostated bed integrated within the IVIS™ system (Xenogen Corp., Alameda, Calif.). A gray scale body surface image was collected in the chamber under dim illumination, followed by acquisition and overlay of the pseudocolor image representing the spatial distribution of detected photon counts emerging from active luciferase within the animal. An integration time of 1 minute was used for luminescent image acquisition.

Figure 2:
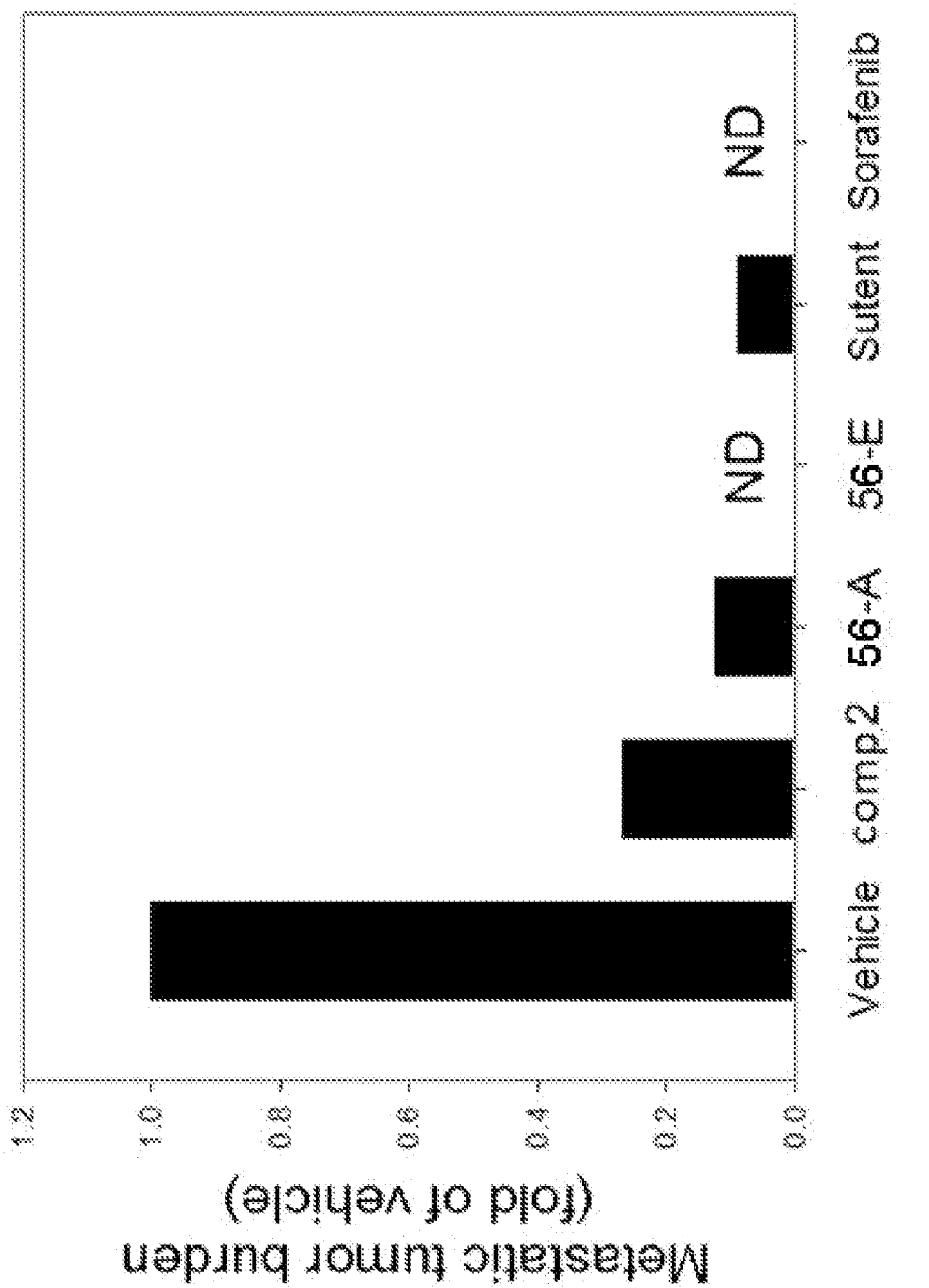
FIG. 2 illustrates the efficacy of certain compounds of this invention in inhibiting spontaneous metastasis in mice. N.D.: not detected.

The average of the in vivo bioluminescence intensities measured on the 14$^{th}$ day post tumor cell implantation but before treatment with test compounds severed as a baseline, corresponding to the metastatic tumor burden of the vehicle group, as shown in FIG. 2.

Unexpectedly, at the end of the fourth week after compound treatment (i.e., the sixth week after tumor cell implantation), the groups administered with Compound 2 (denoted as "Comp 2" in FIG. 2) and Compound 91 (denoted as "56-A") exhibited significant lower luminescent signal intensity as compared with the vehicle group while the group treated with Compound 56 (denoted as "56-E") did not exhibit any detectable luminescent signal. See FIG. 2.

The observation indicates that Compounds 2, 56, and 91 are unexpectedly comparable or superior to the commercial drugs such as Sorafenib (Nexavar®) and sunitinib (Sutent®) on the inhibition of the spontaneous metastasis generated by the tumor cells.

EXAMPLE 190

Effects on Tumor Recurrence and Survival Rate $4T1^{LUC+}$ cells obtained by the method described in Example 188 were implanted into the right inguinal mammary fat pads of 6 to 8-week old female BALB/c mice ($1 \times 10^5$ cells in 100 µL PBS/mouse). After 14 days of tumor cell implantation, a single dose of 50 mg/kg body weight of a test compound or vehicle (PBS) was administered intraperitoneally once daily for three weeks. Compounds 2, 56, and 91 were tested in this assay. Sorafenib (Nexavar®) and sunitinib (Sutent®) were also used as reference compounds.

At the end of three-week treatment, the orthotopically grown tumors were surgically removed from the six groups of mice (i.e., 5 groups each treated with a test compound and 1 vehicle group). Then each of the six groups (i.e., 5 groups each treated with a test compound and 1 vehicle group) were divided into two subgroups, one with no further drug treatment (denoted as "stop treatment" in FIG. 3) and the other with continued drug treatment for 35 days (denoted as the "sustain treatment" in FIG. 3).

Bioluminescent data were collected in a manner similar to that described in Example 189 above at the end of day 35 after tumor resection.

Figure 3:
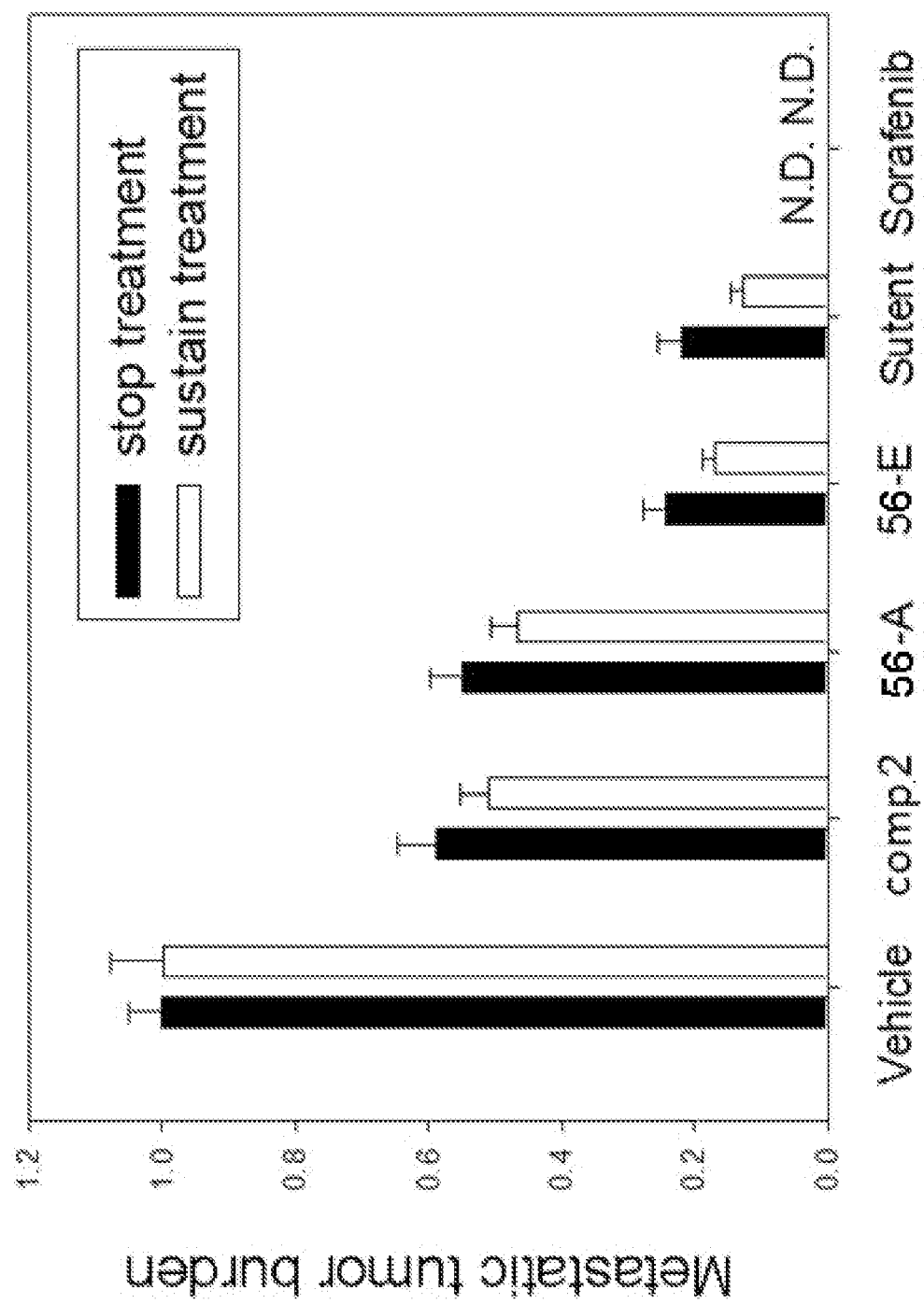
FIG. 3 illustrates the effect of certain compounds of this invention on reducing tumor recurrence in mice. N.D.: not detected.

Unexpectedly, as showed in the FIG. 3, the groups administered with Compound 2 (denoted as "Comp 2" in FIG. 3), Compound 56 (denoted as "56-E"), and Compound 91 (denoted as "56-A") after tumor resection all exhibited lower luminescent signal intensity as compared with the corresponding group without continuous treatment. This observation indicates that these compounds decrease the chance of tumor recurrence.

In addition, Compound 56 reduced tumor recurrence to a degree comparable to that of sunitinib (Sutent®).

Figure 4:
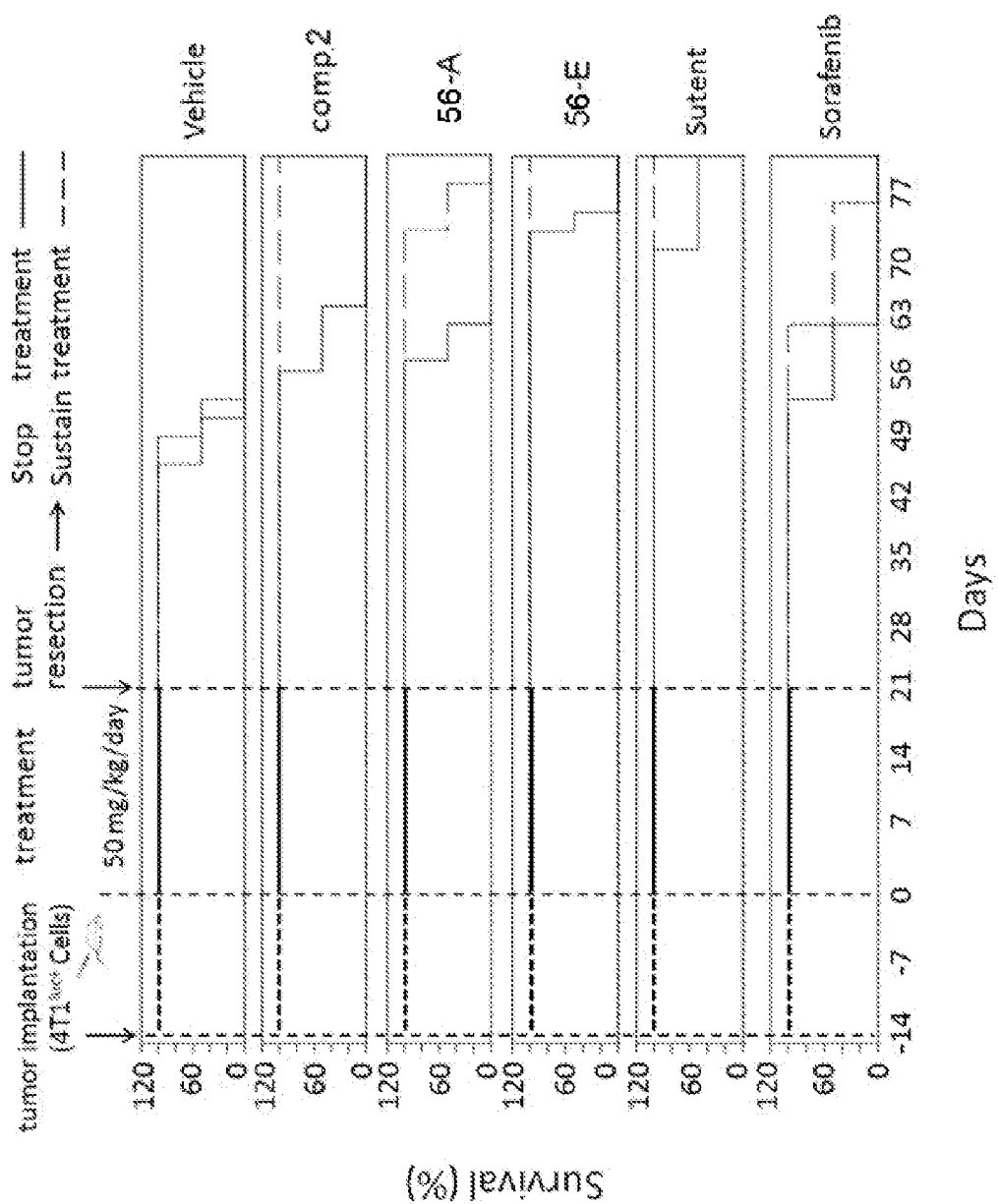
FIG. 4 illustrates the effect of certain compounds of this invention on survival rates of mice.

Also unexpectedly, as indicated by the survival curves in FIG. 4, Compounds 2, 56, and 91 increased the overall survival life span of the treated mice as compared with those in the vehicle group. In addition, the "sustain treatment" subgroup of each treated group exhibited a higher survival rate than the "stop treatment" subgroup.

EXAMPLE 191

Effects on Tumor Self-Seeding

Unlabeled parental 4T1 cells were implanted into a mammary gland of 6 to 8-week old female BALB/c mice ($1 \times 10^5$ cells in 100 µL PBS/mouse). After 14 days of tumor cell implantation, a single dose of 50 mg/kg body weight of a test compound or vehicle (PBS) was administered orally once daily for 2 days. Compound 56 was tested in this assay. Sunitinib (Sutent®) was used as a reference compound. Then $4T1^{luc+}$ cells ($1 \times 10^5$ cells in 100 µL PBS/mouse) were injected into the circulatory system of the mice by intracardiac injection. The mice were then administered orally with a single dose of 50 mg/kg body weight of a test compound or vehicle (PBS) once daily for 2 days.

Bioluminescent data were collected in a manner similar to that described in Example 189 above.

Figure 5B:
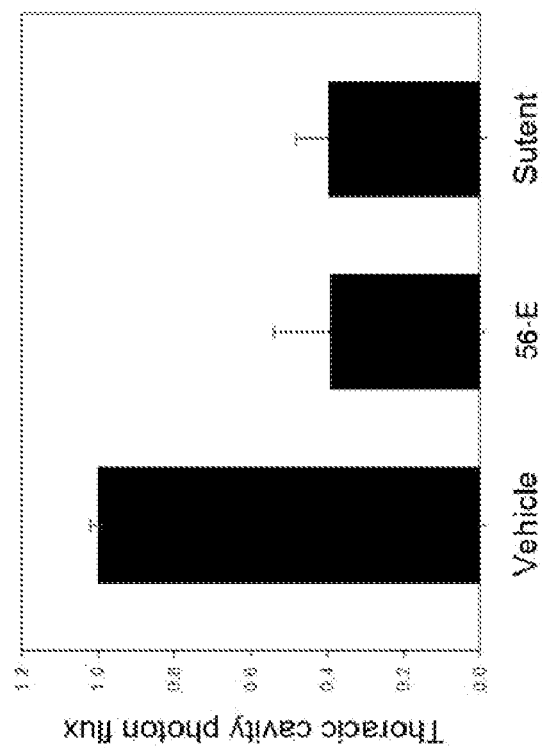
FIGS. 5A and 5B illustrate the inhibitory effect of Compound 56 on tumor self-seeding.
Figure 5A:
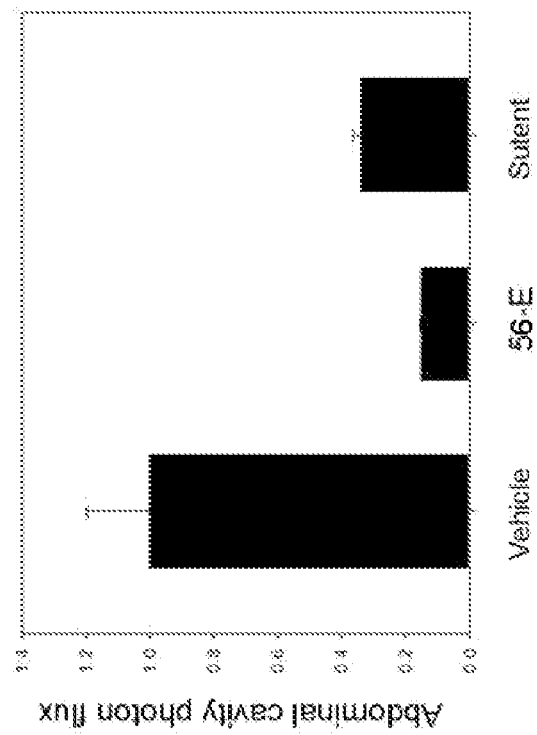

Unexpectedly, as shown in FIGS. 5A and 5B, the mice treated with Compound 56 (denoted as "56-E") and Sutent exhibited much weaker bioluminescence from the thoracic cavity at day 7 post the second 2-day drug treatment as well as much weaker bioluminescence form the abdominal cavity at day 14 post the second 2-day drug treatment as compared with the vehicle group. Even more surprisingly, the mice treated with Compound 56 (denoted as "56-E") exhibited weaker bioluminescence form the abdominal cavity at day 14 post the second 2-day drug treatment as compared with the the Sutent-treated group. These observations indicate that Compound 56 exhibited comparable or even superior ability in inhibiting tumor self-seeding to that of Sutent.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound of formula (I):

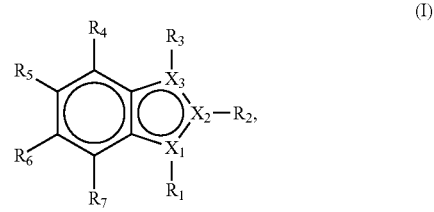

wherein
  $X_1$ is N;
  $X_2$ is C;

$X_3$ is N;

$R_1$ is alkyl or cycloalkyl;

$R_3$ is deleted $R_2$ is substituted and unsubstituted benzimidazol-4-yl, substituted and unsubstituted dihydrobenzimidazol-4-yl or substituted and unsubstituted indazol-6-yl;

$R_4$, $R_6$, and $R_7$ are H; and $R_5$ is $COOR_d$ wherein $R_d$ is H or alkyl, or a salt, a prodrug or a solvate thereof.

2. The compound of claim 1, wherein $R_2$ is substituted and unsubstituted indazol-6-yl.

3. The compound of claim 2, wherein the compound is one of the compounds as follows:

Compound 2

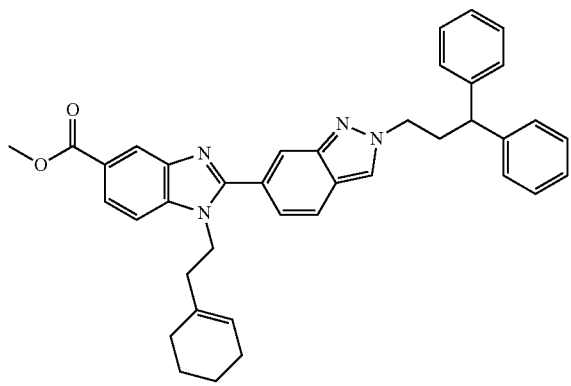

Compound 25

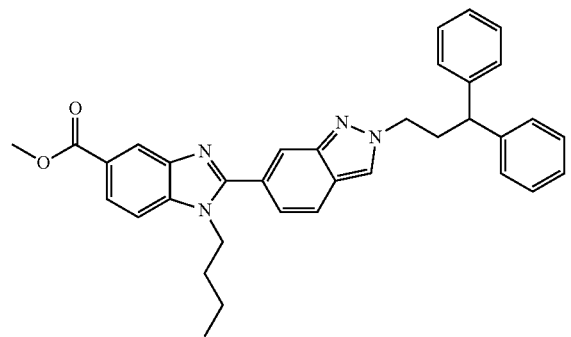

Compound 26

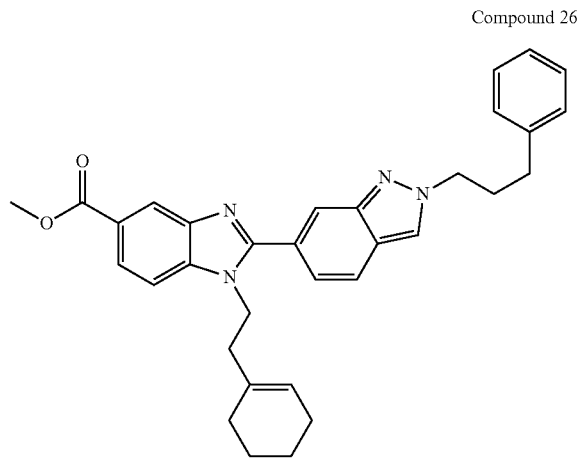

Compound 27

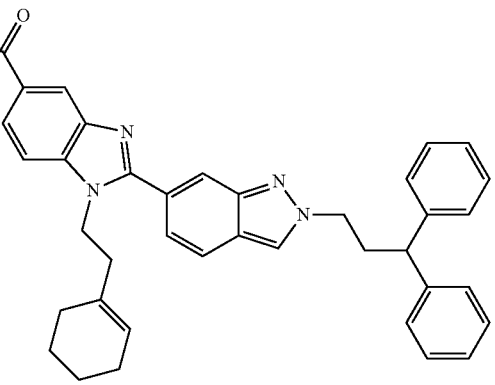

Compound 49

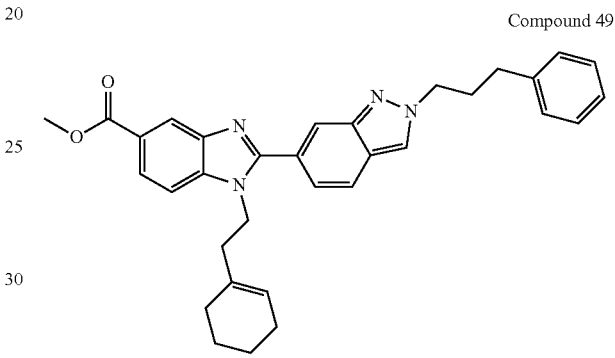

Compound 52

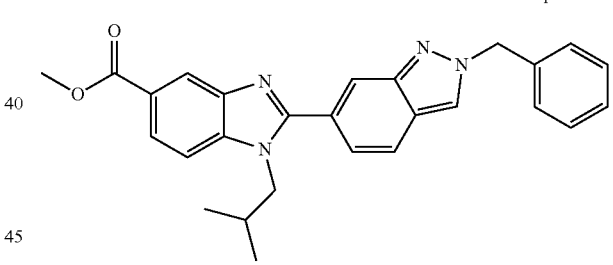

Compound 53

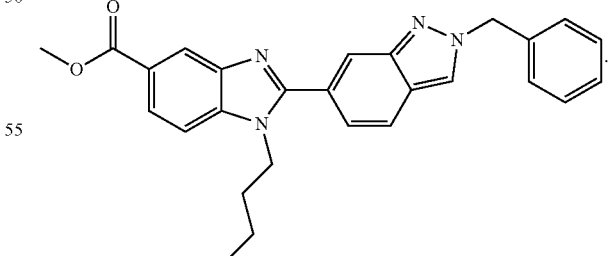

4. The compound of claim 1, wherein $R_2$ is substituted and unsubstituted benzimidazol-4-yl, or dihydrobenzimidazol-4-yl.

5. The compound of claim 4, wherein the compound is one of the compounds as follows:
Compound 56
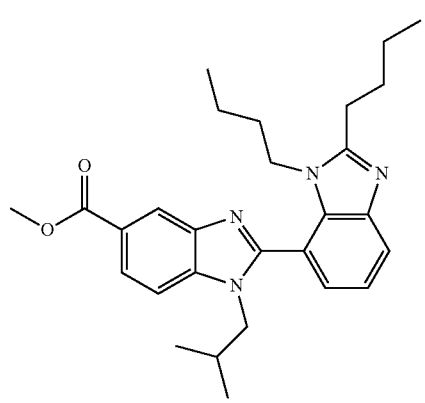
Compound 59
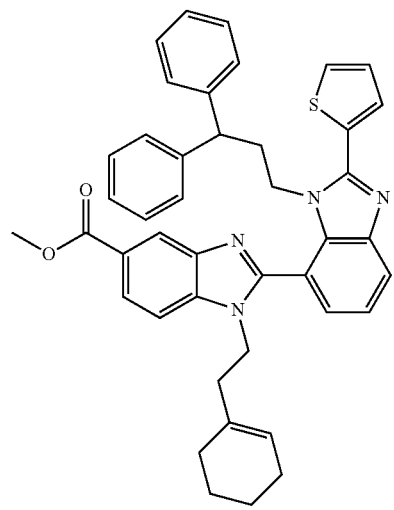
Compound 62
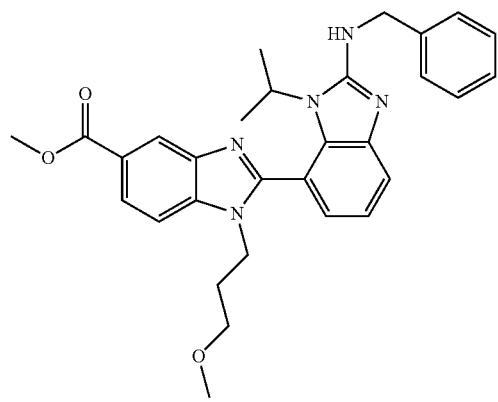
-continued
Compound 64
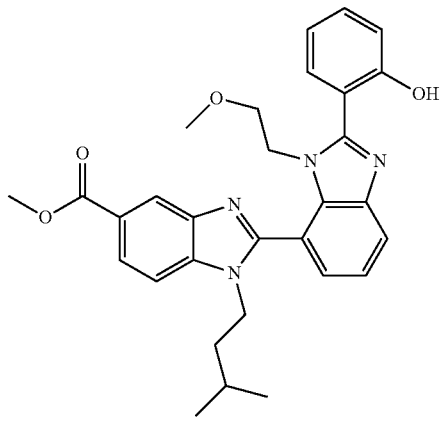
Compound 65
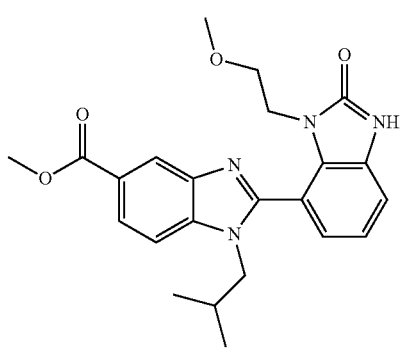
Compound 81
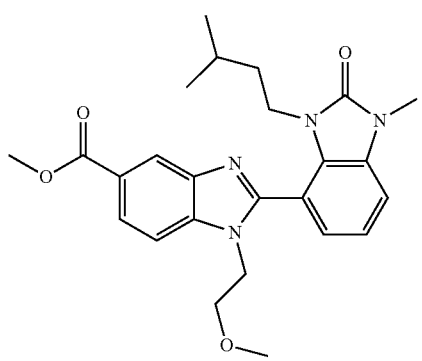
Compound 83
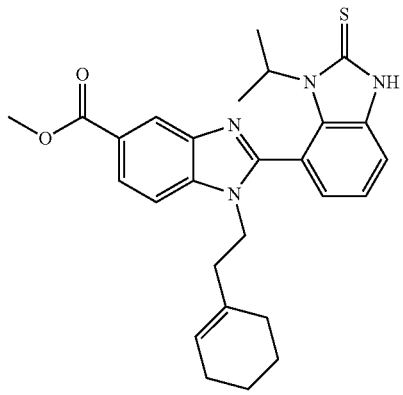

Compound 84
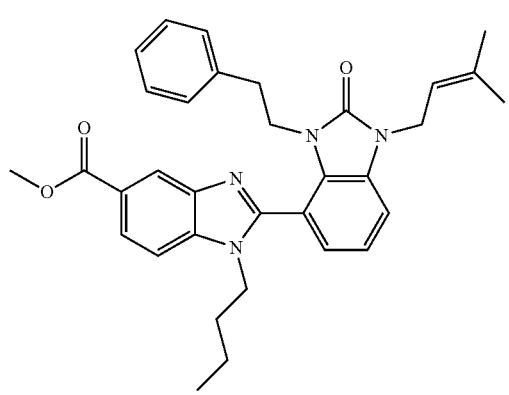
Compound 85
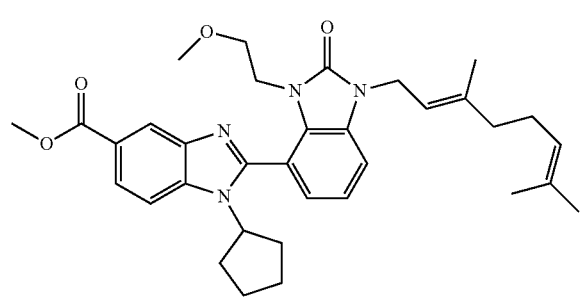
Compound 87
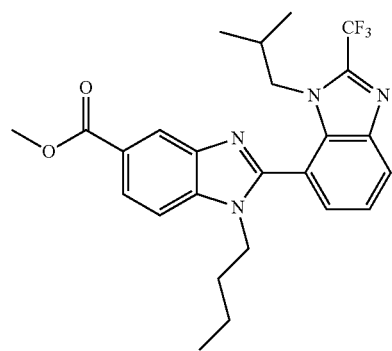
Compound 89
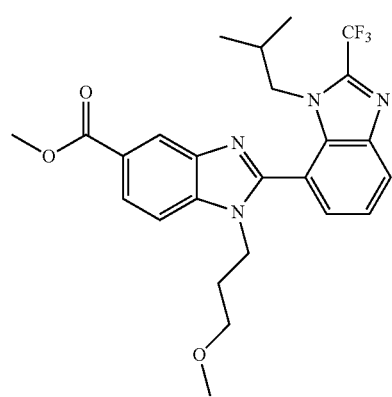
Compound 91
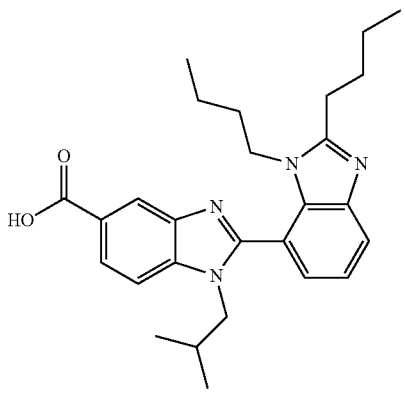
Compound 100
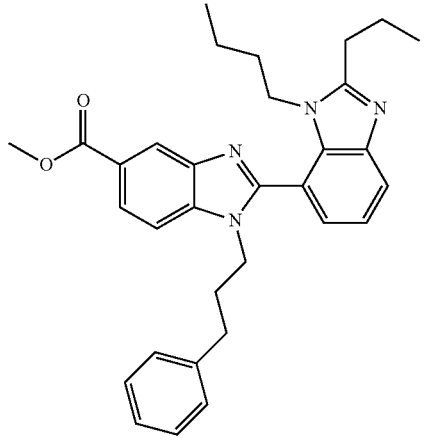
Compound 113
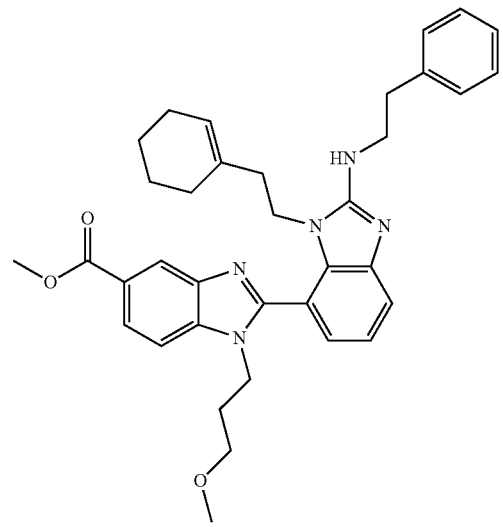

Compound 114
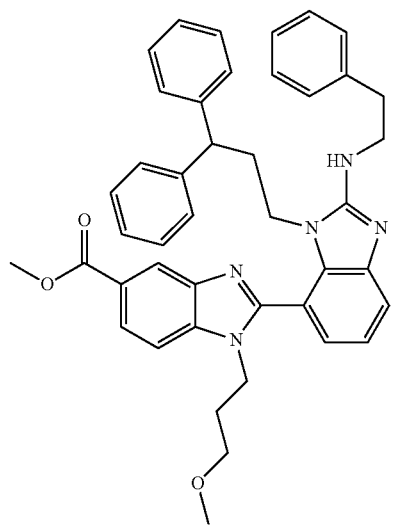
Compound 119
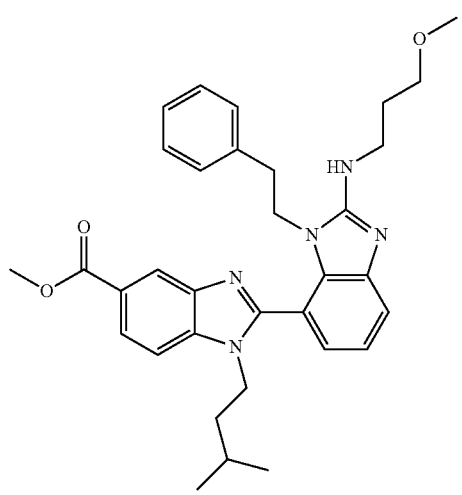
Compound 121
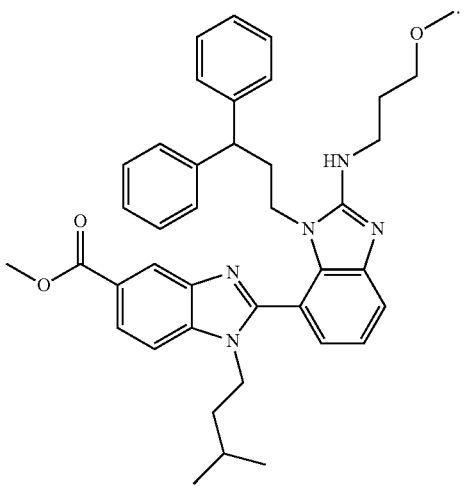
6. A pharmaceutical composition, comprising a pharmaceutically acceptable carrier and a compound of claim 1.
7. A pharmaceutical composition, comprising a pharmaceutically acceptable carrier and a compound of claim 2.
8. A pharmaceutical composition, comprising a pharmaceutically acceptable carrier and a compound of claim 4.
* * * * *